(12) United States Patent
Khairkhahan

(10) Patent No.: US 9,872,767 B2
(45) Date of Patent: Jan. 23, 2018

(54) RETRIEVABLE CARDIAC DEVICES

(71) Applicant: CardioKinetix, Inc., Menlo Park, CA (US)

(72) Inventor: Alexander Khairkhahan, Palo Alto, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 148 days.

(21) Appl. No.: 14/681,930

(22) Filed: Apr. 8, 2015

(65) Prior Publication Data

US 2015/0209144 A1    Jul. 30, 2015

Related U.S. Application Data

(62) Division of application No. 13/954,221, filed on Jul. 30, 2013, now Pat. No. 9,017,394, which is a division
(Continued)

(51) Int. Cl.
*A61M 29/00* (2006.01)
*A61F 2/24* (2006.01)
(Continued)

(52) U.S. Cl.
CPC ........ *A61F 2/2427* (2013.01); *A61B 17/0057* (2013.01); *A61B 17/12022* (2013.01); *A61B 17/12122* (2013.01); *A61B 17/12172* (2013.01); *A61B 17/3468* (2013.01); *A61B 2017/00243* (2013.01); *A61B 2017/00575* (2013.01); *A61B 2017/00579* (2013.01); *A61B 2017/00592* (2013.01); *A61B 2017/00597* (2013.01); *A61B 2017/00615* (2013.01); *A61B 2017/00632* (2013.01); *A61B 2017/00867* (2013.01); *A61B 2017/0649* (2013.01);
(Continued)

(58) Field of Classification Search
CPC .......... A61B 17/0057; A61B 17/12022; A61B 17/12172
See application file for complete search history.

(56) References Cited

U.S. PATENT DOCUMENTS

| | | |
|---|---|---|
| 3,874,388 A | 4/1975 | King et al. |
| 4,007,743 A | 2/1977 | Blake |

(Continued)

FOREIGN PATENT DOCUMENTS

| | | |
|---|---|---|
| EP | 1474032 A2 | 11/2004 |
| EP | 2068768 A | 6/2009 |

(Continued)

OTHER PUBLICATIONS

Boutillette et al.; U.S. Appl. No. 15/133,080 entitled "Devices and methods for delivering an endocardial device," filed Apr. 19, 2016.
(Continued)

*Primary Examiner* — Vy Bui

(74) *Attorney, Agent, or Firm* — Joel B. German

(57) ABSTRACT

Removable cardiac implants, applicators for inserting, repositioning and/or removing them, and methods of using them are described. In particular, removable or repositionable ventricular partitioning devices are described. Systems including removable implants and applicators for inserting and/or removing them are also described.

21 Claims, 45 Drawing Sheets

Related U.S. Application Data of application No. 13/487,684, filed on Jun. 4, 2012, now Pat. No. 8,500,790, which is a division of application No. 12/198,022, filed on Aug. 25, 2008, now Pat. No. 8,246,671.

(51) Int. Cl.
*A61B 17/00* (2006.01)
*A61B 17/12* (2006.01)
*A61B 17/34* (2006.01)
*A61B 17/064* (2006.01)

(52) U.S. Cl.
CPC .............. *A61B 2017/12054* (2013.01); *A61B 2017/12095* (2013.01); *A61F 2/2487* (2013.01); *A61F 2002/2484* (2013.01); *A61F 2250/0003* (2013.01)

(56) References Cited

U.S. PATENT DOCUMENTS

| | | |
|---|---|---|
| 4,425,908 A | 1/1984 | Simon |
| 4,453,545 A | 6/1984 | Inoue |
| 4,536,893 A | 8/1985 | Parravicini |
| 4,588,404 A | 5/1986 | Lapeyre |
| 4,619,246 A | 10/1986 | Molgaard-Nielsen et al. |
| 4,685,446 A | 8/1987 | Choy |
| 4,710,192 A | 12/1987 | Liotta et al. |
| 4,819,751 A | 4/1989 | Shimada et al. |
| 4,832,055 A | 5/1989 | Palestrant |
| 4,917,089 A | 4/1990 | Sideris |
| 4,983,165 A | 1/1991 | Loiterman |
| 5,104,399 A | 4/1992 | Lazarus |
| 5,192,301 A | 3/1993 | Kamiya et al. |
| 5,192,314 A | 3/1993 | Daskalakis |
| 5,258,000 A | 11/1993 | Gianturco |
| 5,375,612 A | 12/1994 | Cottenceau et al. |
| 5,385,156 A | 1/1995 | Oliva |
| 5,389,087 A | 2/1995 | Miraki |
| 5,425,744 A | 6/1995 | Fagan et al. |
| 5,433,727 A | 7/1995 | Sideris |
| 5,451,235 A | 9/1995 | Lock et al. |
| 5,496,277 A | 3/1996 | Termin et al. |
| 5,527,337 A | 6/1996 | Stack et al. |
| 5,527,338 A | 6/1996 | Purdy |
| 5,549,621 A | 8/1996 | Bessler et al. |
| 5,551,435 A | 9/1996 | Sramek |
| 5,578,069 A | 11/1996 | Miner, II |
| 5,634,936 A | 6/1997 | Linden et al. |
| 5,634,942 A | 6/1997 | Chevillon et al. |
| 5,647,870 A | 7/1997 | Kordis et al. |
| 5,702,343 A | 12/1997 | Alferness |
| 5,709,707 A | 1/1998 | Lock et al. |
| 5,758,664 A | 6/1998 | Campbell et al. |
| 5,791,231 A | 8/1998 | Cohn et al. |
| 5,797,849 A | 8/1998 | Vesely et al. |
| 5,797,960 A | 8/1998 | Stevens et al. |
| 5,800,457 A | 9/1998 | Gelbfish |
| 5,800,517 A | 9/1998 | Anderson et al. |
| 5,829,447 A | 11/1998 | Stevens et al. |
| 5,833,682 A | 11/1998 | Amplatz et al. |
| 5,833,698 A | 11/1998 | Hinchliffe et al. |
| 5,836,968 A | 11/1998 | Simon et al. |
| 5,843,170 A | 12/1998 | Ahn |
| 5,860,951 A | 1/1999 | Eggers et al. |
| 5,861,003 A | 1/1999 | Latson et al. |
| 5,865,730 A | 2/1999 | Fox et al. |
| 5,865,791 A | 2/1999 | Whayne et al. |
| 5,871,017 A | 2/1999 | Mayer |
| 5,875,782 A | 3/1999 | Ferrari et al. |
| 5,876,325 A | 3/1999 | Mizuno et al. |
| 5,876,449 A | 3/1999 | Starck et al. |
| 5,879,366 A | 3/1999 | Shaw et al. |
| 5,882,340 A | 3/1999 | Yoon |
| 5,910,150 A | 6/1999 | Saadat |
| 5,916,145 A | 6/1999 | Chu et al. |
| 5,924,424 A | 7/1999 | Stevens et al. |
| 5,925,062 A | 7/1999 | Purdy |
| 5,925,076 A | 7/1999 | Inoue |
| 5,928,260 A | 7/1999 | Chin et al. |
| 5,961,440 A | 10/1999 | Schweich, Jr. et al. |
| 5,961,539 A | 10/1999 | Northrup, III et al. |
| 5,984,917 A | 11/1999 | Fleischman et al. |
| 6,024,096 A | 2/2000 | Buckberg |
| 6,024,756 A | 2/2000 | Huebsch et al. |
| 6,036,720 A | 3/2000 | Abrams et al. |
| 6,045,497 A | 4/2000 | Schweich, Jr. et al. |
| 6,059,715 A | 5/2000 | Schweich, Jr. et al. |
| 6,076,013 A | 6/2000 | Brennan et al. |
| 6,077,214 A | 6/2000 | Mortier et al. |
| 6,077,218 A | 6/2000 | Alferness |
| 6,093,199 A | 7/2000 | Brown et al. |
| 6,095,968 A | 8/2000 | Snyders |
| 6,096,347 A | 8/2000 | Geddes et al. |
| 6,099,832 A | 8/2000 | Mickle et al. |
| 6,102,887 A | 8/2000 | Altman |
| 6,125,852 A | 10/2000 | Stevens et al. |
| 6,132,438 A | 10/2000 | Fleischman et al. |
| 6,142,973 A | 11/2000 | Carleton et al. |
| 6,152,144 A | 11/2000 | Lesh et al. |
| 6,155,968 A | 12/2000 | Wilk |
| 6,156,027 A | 12/2000 | West |
| 6,161,543 A | 12/2000 | Cox et al. |
| 6,193,731 B1 | 2/2001 | Oppelt et al. |
| 6,221,092 B1 | 4/2001 | Koike et al. |
| 6,221,104 B1 | 4/2001 | Buckberg et al. |
| 6,230,714 B1 | 5/2001 | Alferness et al. |
| 6,231,561 B1 | 5/2001 | Frazier et al. |
| 6,258,021 B1 | 7/2001 | Wilk |
| 6,267,772 B1 | 7/2001 | Mulhauser et al. |
| 6,290,674 B1 | 9/2001 | Roue et al. |
| 6,296,656 B1 | 10/2001 | Bolduc et al. |
| 6,312,446 B1 | 11/2001 | Huebsch et al. |
| 6,328,727 B1 | 12/2001 | Frazier et al. |
| 6,334,864 B1 | 1/2002 | Amplatz et al. |
| 6,343,605 B1 | 2/2002 | Lafontaine |
| 6,348,068 B1 | 2/2002 | Campbell et al. |
| 6,355,052 B1 | 3/2002 | Neuss et al. |
| 6,360,749 B1 | 3/2002 | Jayaraman |
| 6,364,896 B1 | 4/2002 | Addis |
| 6,387,042 B1 | 5/2002 | Herrero |
| 6,406,420 B1 | 6/2002 | McCarthy et al. |
| 6,419,669 B1 | 7/2002 | Frazier et al. |
| 6,436,088 B2 | 8/2002 | Frazier et al. |
| 6,450,171 B1 | 9/2002 | Buckberg et al. |
| 6,482,146 B1 | 11/2002 | Alferness et al. |
| 6,482,228 B1 | 11/2002 | Norred |
| 6,506,204 B2 | 1/2003 | Mazzocchi |
| 6,508,756 B1 | 1/2003 | Kung et al. |
| 6,511,496 B1 | 1/2003 | Huter et al. |
| 6,537,198 B1 | 3/2003 | Vidlund et al. |
| 6,551,303 B1 | 4/2003 | Van Tassel et al. |
| 6,572,643 B1 | 6/2003 | Gharibadeh |
| 6,586,414 B2 | 7/2003 | Haque et al. |
| 6,592,608 B2 | 7/2003 | Fisher et al. |
| 6,613,013 B2 | 9/2003 | Haarala et al. |
| 6,622,730 B2 | 9/2003 | Ekvall et al. |
| 6,645,199 B1 | 11/2003 | Jenkins et al. |
| 6,652,555 B1 | 11/2003 | Van Tassel et al. |
| 6,681,773 B2 | 1/2004 | Murphy et al. |
| 6,685,627 B2 | 2/2004 | Jayaraman |
| 6,702,763 B2 | 3/2004 | Murphy et al. |
| 6,730,108 B2 | 5/2004 | Van Tassel et al. |
| 6,776,754 B1 | 8/2004 | Wilk |
| 6,852,076 B2 | 2/2005 | Nikolic et al. |
| 6,887,192 B1 | 5/2005 | Whayne et al. |
| 6,951,534 B2 | 10/2005 | Girard et al. |
| 6,959,711 B2 | 11/2005 | Murphy et al. |
| 6,994,093 B2 | 2/2006 | Murphy et al. |
| 7,144,363 B2 | 12/2006 | Pai et al. |
| 7,172,551 B2 | 2/2007 | Leasure |
| 7,175,660 B2 | 2/2007 | Cartledge et al. |
| 7,279,007 B2 | 10/2007 | Nikolic et al. |
| 7,303,526 B2 | 12/2007 | Sharkey et al. |

(56) References Cited

U.S. PATENT DOCUMENTS

| | | | |
|---|---|---|---|
| 7,320,665 B2 | 1/2008 | Vijay | |
| 7,399,271 B2 | 7/2008 | Khairkhahan et al. | |
| 7,485,088 B2 | 2/2009 | Murphy et al. | |
| 7,530,998 B1 | 5/2009 | Starkey | |
| 7,569,062 B1 | 8/2009 | Kuehn et al. | |
| 7,582,051 B2 * | 9/2009 | Khairkhahan | A61B 17/12022 600/16 |
| 7,674,222 B2 | 3/2010 | Nikolic et al. | |
| 7,758,491 B2 | 7/2010 | Buckner et al. | |
| 7,762,943 B2 | 7/2010 | Khairkhahan | |
| 7,824,325 B2 | 11/2010 | Dubi | |
| 7,862,500 B2 | 1/2011 | Sharkey et al. | |
| 7,887,477 B2 | 2/2011 | Sharkey et al. | |
| 7,897,086 B2 | 3/2011 | Khairkhahan et al. | |
| 7,938,767 B2 | 5/2011 | Evans et al. | |
| 7,976,455 B2 | 7/2011 | Khairkhahan | |
| 7,993,258 B2 | 8/2011 | Feld et al. | |
| 8,192,478 B2 | 6/2012 | Khairkhahan et al. | |
| 8,246,671 B2 | 8/2012 | Khairkhahan et al. | |
| 8,257,428 B2 | 9/2012 | Khairkhahan et al. | |
| 8,377,114 B2 | 2/2013 | Khairkhahan et al. | |
| 8,382,653 B2 | 2/2013 | Dubi et al. | |
| 8,388,672 B2 | 3/2013 | Khairkhahan et al. | |
| 8,398,537 B2 | 3/2013 | Khairkhahan et al. | |
| 8,500,790 B2 | 8/2013 | Khairkhahan | |
| 8,500,795 B2 * | 8/2013 | Khairkhahan | A61B 17/0057 600/16 |
| 8,529,430 B2 | 9/2013 | Nikolic et al. | |
| 8,657,873 B2 | 2/2014 | Khairkhahan et al. | |
| 8,672,827 B2 | 3/2014 | Nikolic et al. | |
| 8,790,242 B2 | 7/2014 | Kermode et al. | |
| 8,827,892 B2 | 9/2014 | Nikolic et al. | |
| 9,017,394 B2 | 4/2015 | Khairkhahan | |
| 9,039,597 B2 | 5/2015 | Kermode et al. | |
| 9,078,660 B2 | 7/2015 | Boutillette et al. | |
| 2001/0014800 A1 | 8/2001 | Frazier et al. | |
| 2002/0019580 A1 | 2/2002 | Lau et al. | |
| 2002/0026092 A1 | 2/2002 | Buckberg et al. | |
| 2002/0028981 A1 | 3/2002 | Lau et al. | |
| 2002/0032481 A1 | 3/2002 | Gabbay | |
| 2002/0055767 A1 | 5/2002 | Forde et al. | |
| 2002/0055775 A1 | 5/2002 | Carpentier et al. | |
| 2002/0111647 A1 | 8/2002 | Khairkhahan et al. | |
| 2002/0133227 A1 | 9/2002 | Murphy et al. | |
| 2002/0161392 A1 | 10/2002 | Dubrul | |
| 2002/0161394 A1 | 10/2002 | Macoviak et al. | |
| 2002/0169359 A1 | 11/2002 | McCarthy et al. | |
| 2002/0169360 A1 | 11/2002 | Taylor et al. | |
| 2002/0183604 A1 | 12/2002 | Gowda et al. | |
| 2002/0188170 A1 | 12/2002 | Santamore et al. | |
| 2003/0045896 A1 | 3/2003 | Murphy et al. | |
| 2003/0078671 A1 | 4/2003 | Lesniak et al. | |
| 2003/0109770 A1 | 6/2003 | Sharkey et al. | |
| 2003/0120337 A1 | 6/2003 | Van Tassel et al. | |
| 2003/0135230 A1 | 7/2003 | Massey et al. | |
| 2003/0149333 A1 | 8/2003 | Alferness | |
| 2003/0149422 A1 | 8/2003 | Muller | |
| 2003/0181942 A1 | 9/2003 | Sutton et al. | |
| 2003/0220667 A1 | 11/2003 | van der Burg et al. | |
| 2004/0002626 A1 | 1/2004 | Feld et al. | |
| 2004/0034366 A1 | 2/2004 | van der Burg et al. | |
| 2004/0044361 A1 | 3/2004 | Frazier et al. | |
| 2004/0054394 A1 | 3/2004 | Lee | |
| 2004/0064014 A1 | 4/2004 | Melvin et al. | |
| 2004/0122090 A1 | 6/2004 | Lipton | |
| 2004/0127935 A1 | 7/2004 | Van Tassel et al. | |
| 2004/0133062 A1 | 7/2004 | Pai et al. | |
| 2004/0136992 A1 | 7/2004 | Burton et al. | |
| 2004/0172042 A1 | 9/2004 | Suon et al. | |
| 2004/0186511 A1 | 9/2004 | Stephens et al. | |
| 2004/0215230 A1 | 10/2004 | Frazier et al. | |
| 2004/0220610 A1 | 11/2004 | Kreidler et al. | |
| 2004/0243170 A1 | 12/2004 | Suresh et al. | |
| 2004/0260331 A1 | 12/2004 | D'Aquanni et al. | |
| 2004/0260346 A1 | 12/2004 | Overall et al. | |
| 2004/0267086 A1 | 12/2004 | Anstadt et al. | |
| 2004/0267378 A1 | 12/2004 | Gazi et al. | |
| 2005/0007031 A1 | 1/2005 | Hyder | |
| 2005/0015109 A1 | 1/2005 | Lichtenstein | |
| 2005/0038470 A1 | 2/2005 | van der Burg et al. | |
| 2005/0043708 A1 | 2/2005 | Gleeson et al. | |
| 2005/0065548 A1 | 3/2005 | Marino et al. | |
| 2005/0085826 A1 | 4/2005 | Nair et al. | |
| 2005/0096498 A1 | 5/2005 | Houser et al. | |
| 2005/0113811 A1 | 5/2005 | Houser et al. | |
| 2005/0113861 A1 | 5/2005 | Corcoran et al. | |
| 2005/0124849 A1 | 6/2005 | Barbut et al. | |
| 2005/0137690 A1 | 6/2005 | Salahieh et al. | |
| 2005/0142180 A1 | 6/2005 | Bisgaier et al. | |
| 2005/0177180 A1 | 8/2005 | Kaganov et al. | |
| 2005/0187620 A1 | 8/2005 | Pai et al. | |
| 2005/0216052 A1 | 9/2005 | Mazzocchi et al. | |
| 2005/0228434 A1 | 10/2005 | Amplatz et al. | |
| 2005/0277981 A1 | 12/2005 | Maahs et al. | |
| 2005/0277983 A1 | 12/2005 | Saadat et al. | |
| 2005/0283218 A1 | 12/2005 | Williams | |
| 2006/0019888 A1 | 1/2006 | Zhou | |
| 2006/0025800 A1 | 2/2006 | Suresh | |
| 2006/0030881 A1 | 2/2006 | Sharkey et al. | |
| 2006/0063970 A1 | 3/2006 | Raman et al. | |
| 2006/0069430 A9 | 3/2006 | Rahdert et al. | |
| 2006/0079736 A1 | 4/2006 | Chin et al. | |
| 2006/0116692 A1 | 6/2006 | Ward | |
| 2006/0136043 A1 | 6/2006 | Cully et al. | |
| 2006/0199995 A1 | 9/2006 | Vijay | |
| 2006/0229491 A1 | 10/2006 | Sharkey et al. | |
| 2006/0259124 A1 | 11/2006 | Matsuoka et al. | |
| 2006/0276684 A1 | 12/2006 | Speziali | |
| 2007/0129753 A1 | 6/2007 | Quinn et al. | |
| 2007/0135889 A1 | 6/2007 | Moore et al. | |
| 2007/0162048 A1 | 7/2007 | Quinn et al. | |
| 2007/0213578 A1 | 9/2007 | Khairkhahan et al. | |
| 2008/0015717 A1 | 1/2008 | Griffin et al. | |
| 2008/0045778 A1 | 2/2008 | Lichtenstein et al. | |
| 2008/0228205 A1 | 9/2008 | Sharkey et al. | |
| 2009/0112050 A1 | 4/2009 | Farnan et al. | |
| 2010/0030256 A1 | 2/2010 | Dubrul et al. | |
| 2010/0274227 A1 | 10/2010 | Khairkhahan et al. | |
| 2011/0092761 A1 | 4/2011 | Almog et al. | |
| 2011/0178362 A1 | 7/2011 | Evans et al. | |
| 2011/0264204 A1 | 10/2011 | Khairkhahan | |
| 2013/0090677 A1 | 4/2013 | Evans et al. | |
| 2013/0165735 A1 | 6/2013 | Khairkhahan et al. | |
| 2013/0270735 A1 | 10/2013 | Alexander | |
| 2013/0274595 A1 | 10/2013 | Kermode et al. | |
| 2014/0180271 A1 | 6/2014 | Johnson et al. | |
| 2014/0343356 A1 | 11/2014 | Nikolic et al. | |
| 2015/0265405 A1 | 9/2015 | Boutillette et al. | |

FOREIGN PATENT DOCUMENTS

| | | |
|---|---|---|
| EP | 2244661 B1 | 3/2012 |
| EP | 2082690 B1 | 6/2012 |
| JP | H08257031 A | 10/1996 |
| JP | 2001520910 A | 11/2001 |
| JP | 2003512128 A | 4/2003 |
| JP | 2003512129 A | 4/2003 |
| JP | 2005324019 | 11/2005 |
| JP | 2008514291 A | 5/2008 |
| WO | WO 96/37859 | 11/1996 |
| WO | WO 98/03213 A1 | 1/1998 |
| WO | WO 00/27292 A1 | 5/2000 |
| WO | WO 00/42919 A1 | 7/2000 |
| WO | WO 00/50639 A2 | 8/2000 |
| WO | WO 01/30266 A1 | 5/2001 |
| WO | WO 01/78625 A1 | 10/2001 |
| WO | WO 02/30335 A2 | 4/2002 |
| WO | WO 02/45710 A1 | 6/2002 |
| WO | WO 02/071977 A2 | 9/2002 |
| WO | WO 02/087481 A1 | 11/2002 |
| WO | WO 03/007778 A2 | 1/2003 |
| WO | WO 03/043507 A2 | 5/2003 |
| WO | WO 03/073961 A1 | 9/2003 |
| WO | WO 03/090716 A1 | 11/2003 |

(56) References Cited

FOREIGN PATENT DOCUMENTS

| WO | WO 03/099300 A1 | 12/2003 |
|---|---|---|
| WO | WO 03/099320 A1 | 12/2003 |
| WO | WO 03/103538 A1 | 12/2003 |
| WO | WO 03/103743 A2 | 12/2003 |
| WO | WO 2004/012629 A1 | 2/2004 |
| WO | WO 2004/019866 A2 | 3/2004 |
| WO | WO 2004/066805 A2 | 8/2004 |
| WO | WO 2004/100803 A1 | 11/2004 |
| WO | WO 2005/007031 A2 | 1/2005 |
| WO | WO 2005/007873 A2 | 1/2005 |
| WO | WO 2005/041745 A2 | 5/2005 |
| WO | WO 2005/091860 A2 | 10/2005 |
| WO | WO 2005/102181 A1 | 11/2005 |
| WO | WO 2006/033107 A2 | 3/2006 |
| WO | WO 2006/055683 A2 | 5/2006 |
| WO | WO 2007/016349 A2 | 2/2007 |
| WO | WO 2007/092354 A2 | 8/2007 |
| WO | WO 2007/143560 A2 | 12/2007 |
| WO | WO 2008/010792 A1 | 1/2008 |

OTHER PUBLICATIONS

Kermode et al.; U.S. Appl. No. 15/159,715 entitled "Ventricular volume reduction," filed May 19, 2016.
Kermode et al.; U.S. Appl. No. 14/664,684 entitled "Ventricular volume reduction," filed Mar. 20, 2015.
AGA Medical Corporation. www.amplatzer.com/products. "The Muscular VSD Occluder" and "The Septal Occluder" device description. Accessed Apr. 3, 2002.
Anand et al.; Isolated myocyte contractile function is normal in postinfarct remodeled rat heart with systolic dysfunction; Circulation ; 96(11); pp. 3974-3984; Dec. 1997.
Artrip et al.; Left ventricular volume reduction surgery for heart failure: A physiologic perspective; J Thorac Cardiovasc Surg; vol. 122; No. 4; pp. 775-782; Oct. 2001.
Boersma et al.; Early thrombolytic treatment in acute myocardial infarction: reappraisal of the golden hour; Lancet: vol. 348(9030); pp. 771-775; Sep. 21, 1996.
Dang et al.; Akinetic myocardial infarcts must contain contracting myocytes: finite-element model study; Am J Physiol Heart Circ Physiol ; 288; pp. H1844-H1850; Apr. 2005.
Dang et al.; Effect of ventricular size and patch stiffness in surgical anterior ventricular restoration: a finite element model study; Ann Thorac Surg; 79; pp. 185-193; Jan. 2005.
Di Mattia, et al. Surgical treatment of left ventricular post-infarction aneurysm with endoventriculoplasty: late clinical and functioal results. European Journal of Cardio-thoracic Surgery. 15(4):413-418; Apr. 1999.
Dor, et al. Ventricular remodeling in coronary artery disease. Current Opinion in Cardiology. 12(6):533-537; Nov. 1997.
Dor, V. The treatment of refractory ischemic ventricular tachycardia by endoventricular patch plasty reconstruction of the left ventricle. Seminars in Thoracic and Cardiovascular Surgery. 9(2): 146-155; Apr. 1997.
Dor. Surgery for left ventricular aneurysm. Current Opinion in Cardiology. vol. 5; No. 6; pp. 773-780; Dec. 1990.
Gore Medical. www.goremedical.com. "Helex Septal Occluder" product description. Accessed Apr. 3, 2002.
Grossman et al.; Wall stress and patterns of hypertrophy in the human left ventricle; J Clin Invest; 56; pp. 56-64; Jul. 1975.
Guccione et al.; Finite element stress analysis of left ventricular mechanics in the beating dog heart; J Biomech; 28; pp. 1167-1177; Oct. 1995.
Guccione et al.; Mechanics of active contraction in cardiac muscle: Part II—Cylindrical models of the systolic left ventricle; J Biomech Eng; 115; pp. 82-90; Feb. 1993.
Gutberlet et al.; Myocardial viability assessment in patients with highly impaired left ventricular function: comparison of delayed enhancement, dobutamine stress MRI, end-diastolic wall thickness, and TI201-SPECT with functional recovery after revascularization; Eur Radiol; 15; pp. 872-880; May 2005.
Huisman et al.; Measurement of left ventricular wall stress; Cardiovascular Research; 14; pp. 142-153; Mar. 1980.
Jackson et al.; Extension of borderzone myocardium in postinfarction dilated cardiomyopathy; J Am Coll Cardiol; 40(6); 1160-7; and discussion; pp. 1168-1171; Sep. 2002.
James et al.; Blood Volume and Brain Natriuretic Peptide in Congestive Heart Failure: A Pilot Study; American Heart Journal; vol. 150; issue 5, pp. 984.e1-984.e6 (abstract); Dec. 6, 2005.
Januzzi, James L.; Natriuretic peptide testing: A window into the diagnosis and prognosis of heart failure; Cleveland Clinic Journal of Medicine; vol. 73; No. 2; pp. 149-152 and 155-157; Feb. 2006.
Katsumata, et al. An objective appraisal of partial left ventriculectomy for heart failure. Journal of Congestive Heart Failure and Circulator Support. 1(2): 97-106; (year of pub. sufficiently earlier than effective US filing date and any foreign priority date) 1999.
Kawata, et al. Systolic and Diastolic Function after Patch Reconstruction of Left Ventricular Aneurysms. Ann. Thorac. Surg. 5(2)9:403-407; Feb. 1995.
Priola et al.; Functional characteristics of the left ventricular inflow and outflow tracts; Circ Res; 17; pp. 123-129; Aug. 1965.
Sharkey et al.; Left ventricular apex occluder. Description of a a ventricular partitioning device; EuroInterv.; 2(1); pp. 125-127; May 2006.
U.S. Food & Drug Administration; AneuRx Stent Graft System—Instructions for use; (pre-market approval); Sep. 29, 1999; downloaded Apr. 25, 2013 (http://www.accessdata.fda.gov/cdrh_docs/pdf/P990020c.pdf).
Walker et al; Magnetic resonance imaging-based finite element stress analysis after linear repair of left ventricular aneurysm (author manuscript, 17 pgs.); J Thorac Cardiovasc Surg; 135; pp. 1094-1102 e1-2; May 2008.
Walker et al; MRI-based finite-element analysis of left ventricular aneurysm; Am J Physiol Heart Circ Physiol; 289; pp. H692-H700; Aug. 2005.
Walmsley; Anatomy of left ventricular outflow tract; British Heart Journal; 41; pp. 263-267; Mar. 1979.

* cited by examiner

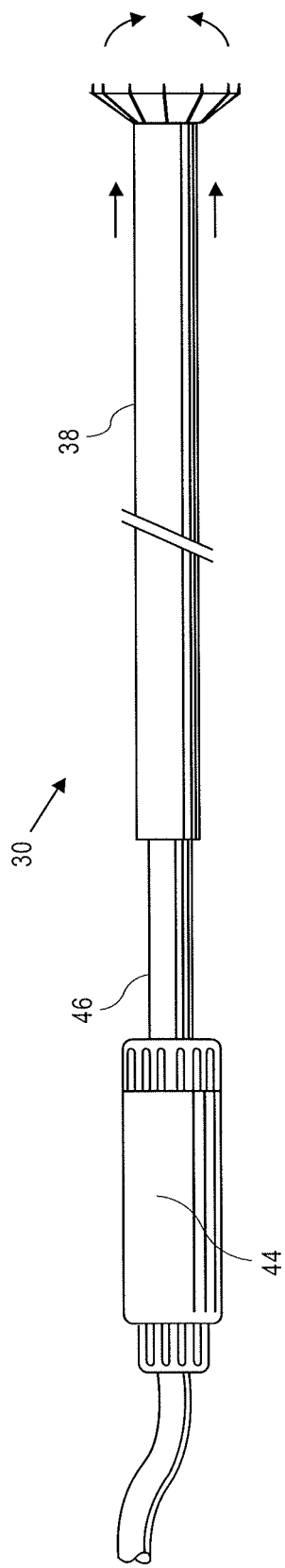
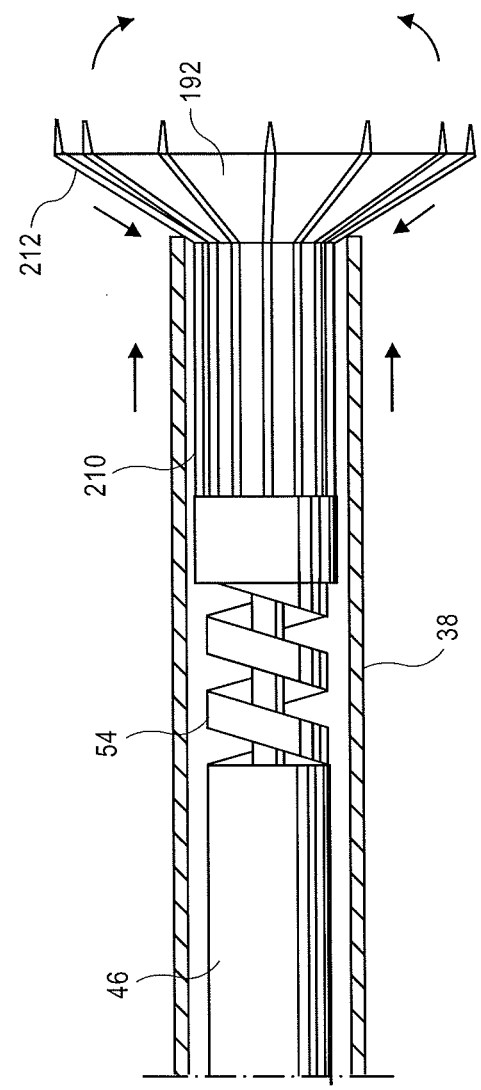
FIG. 3A
FIG. 3B

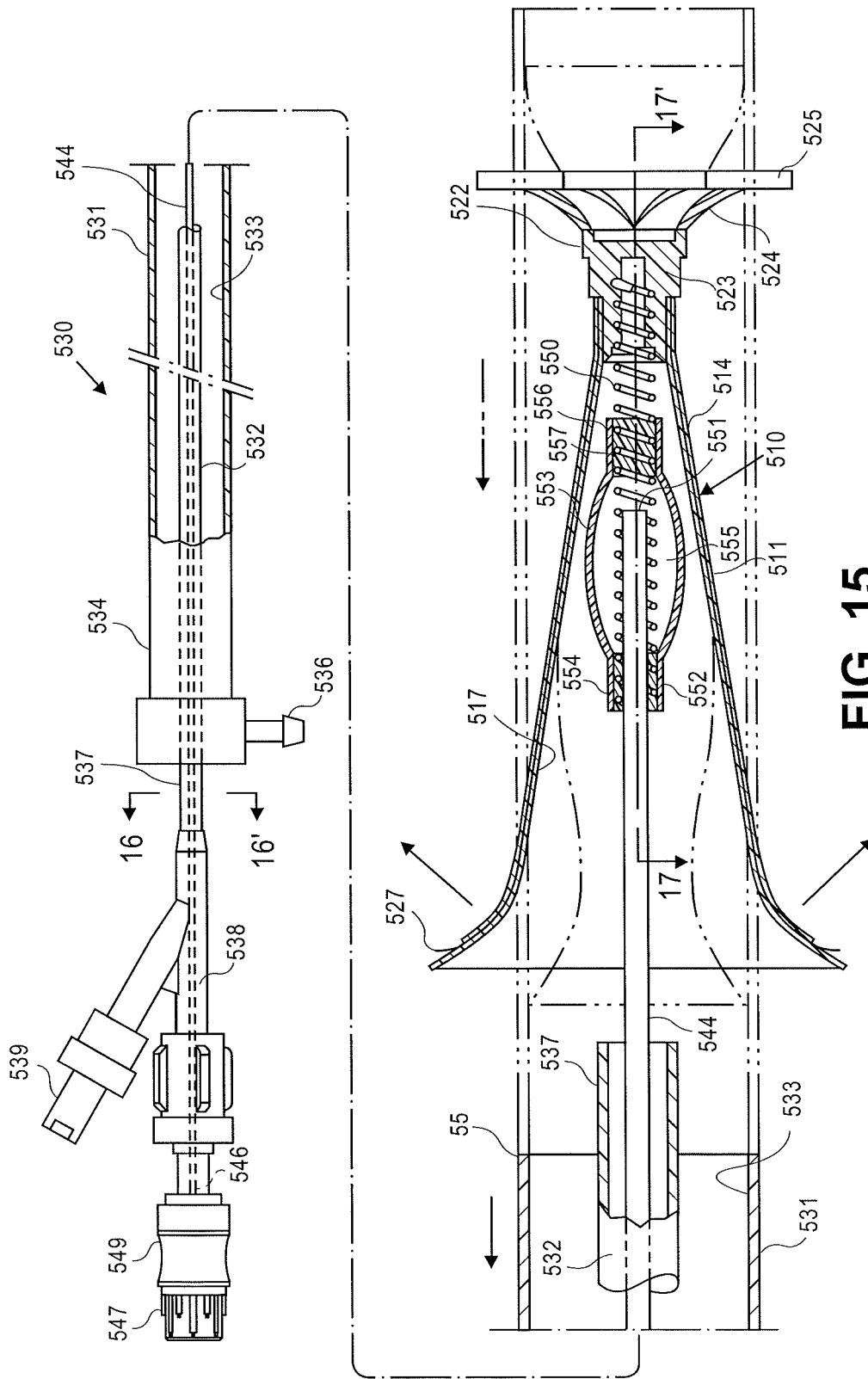

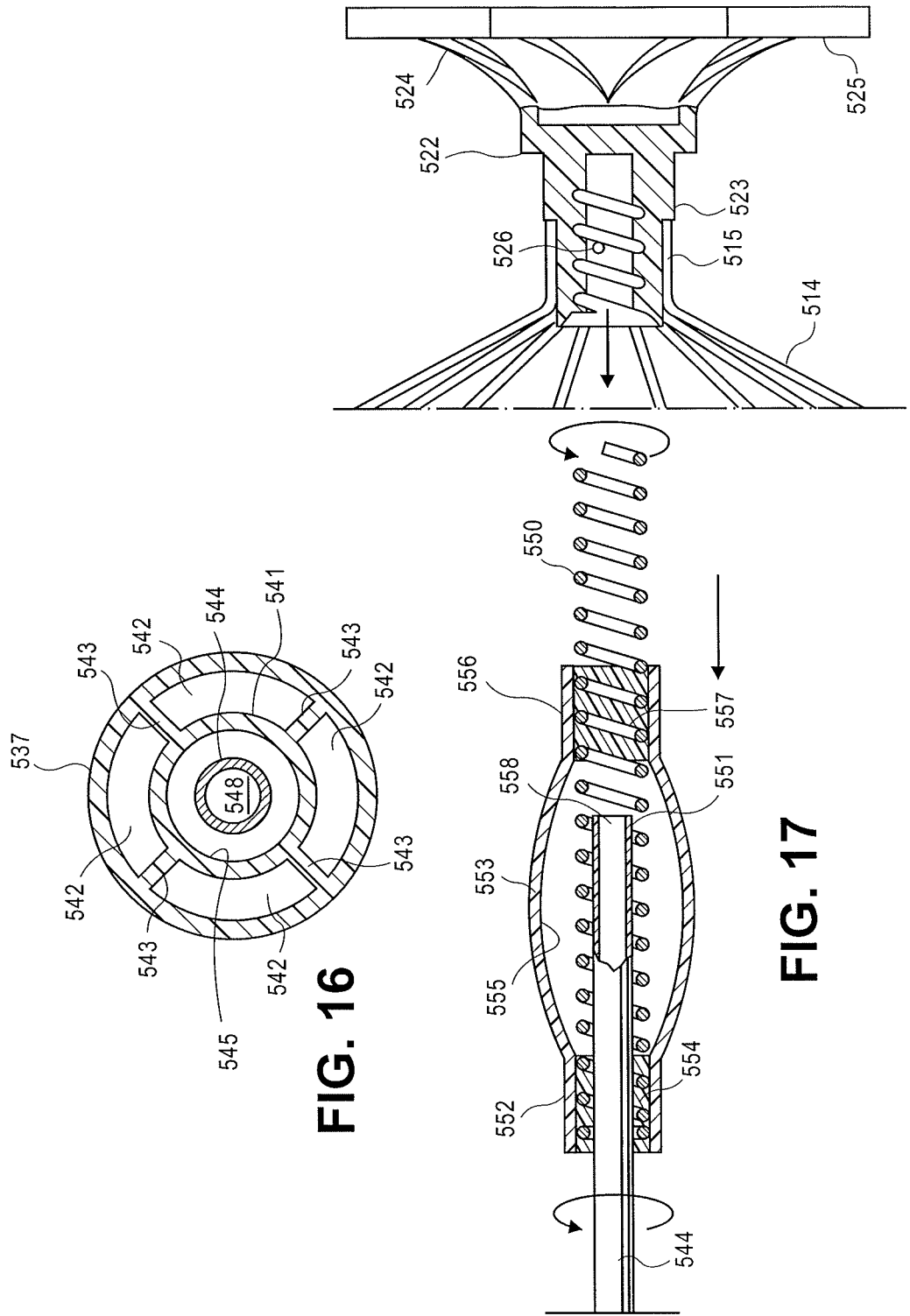

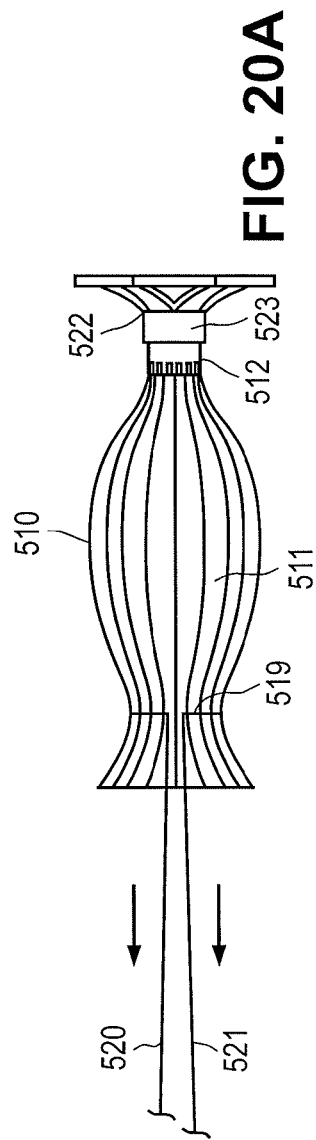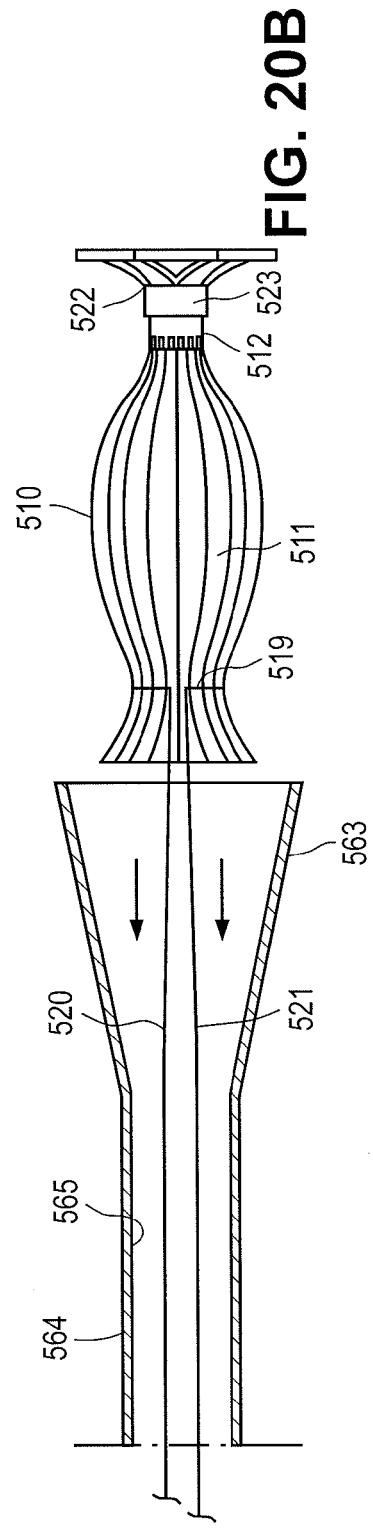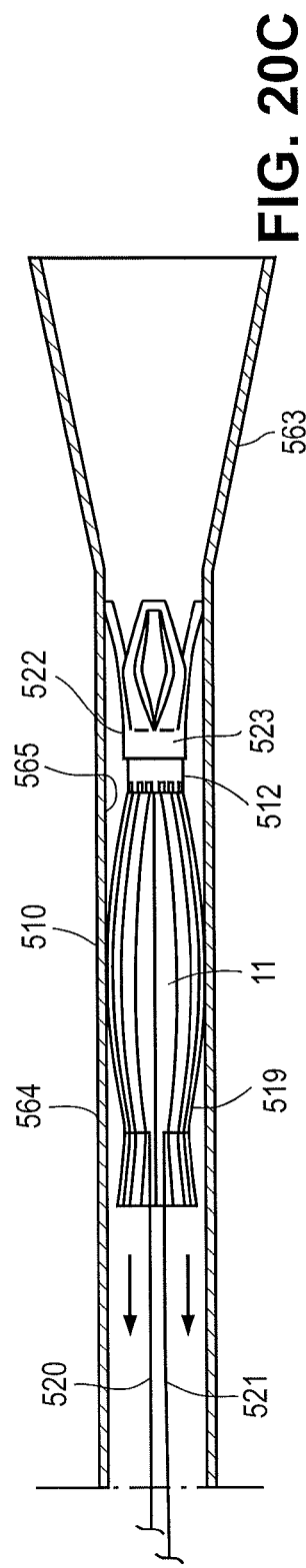

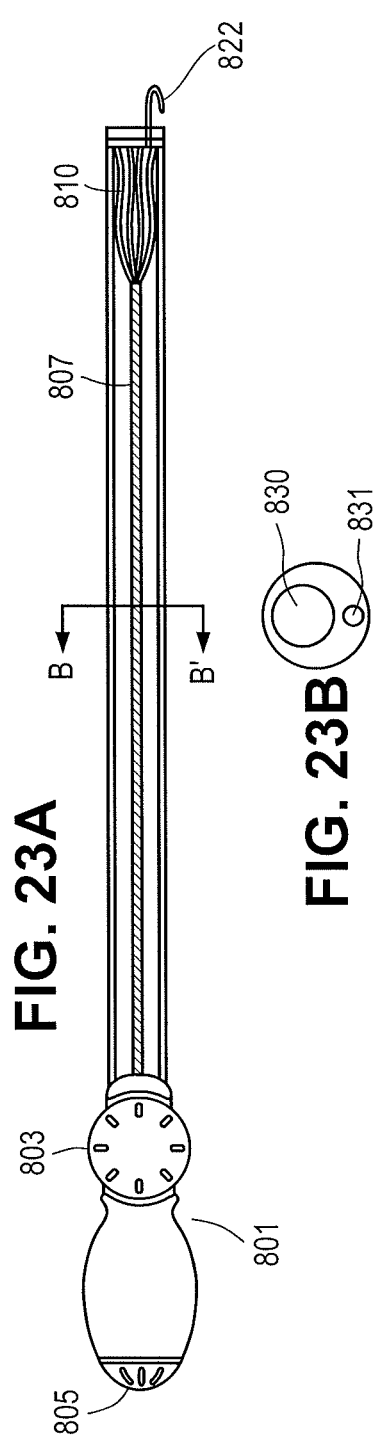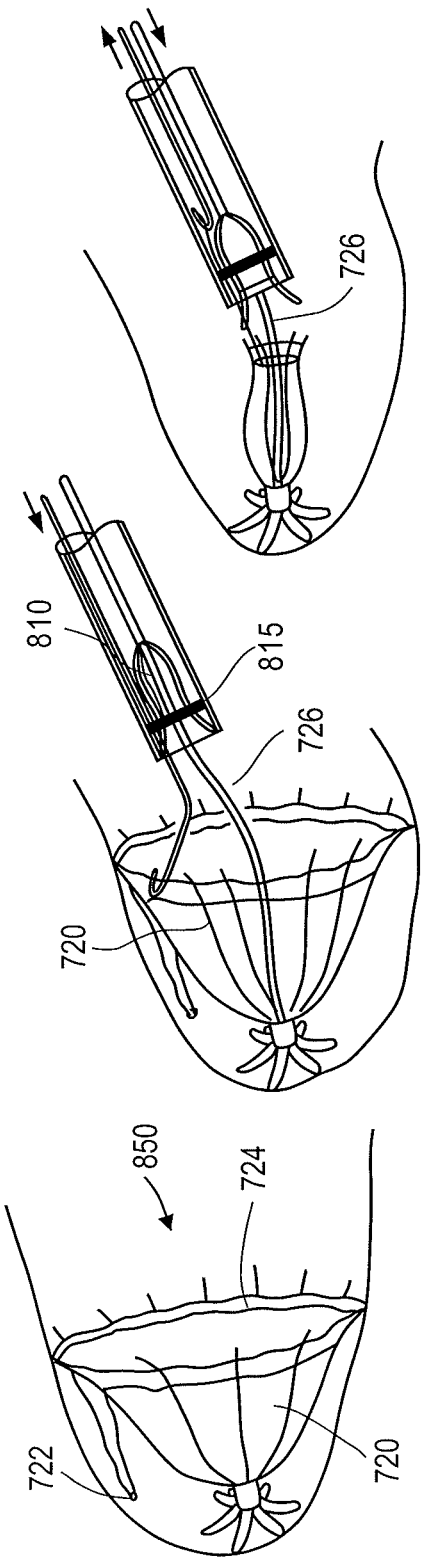
FIG. 23A
FIG. 23B
FIG. 24A
FIG. 24B
FIG. 24C

Section B – B'

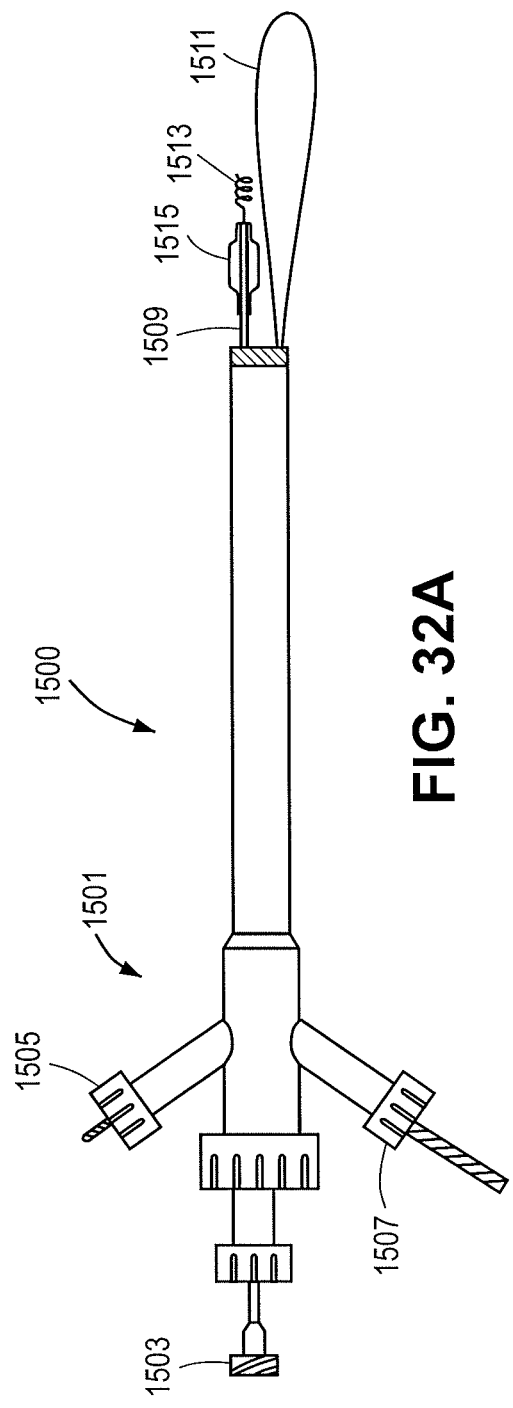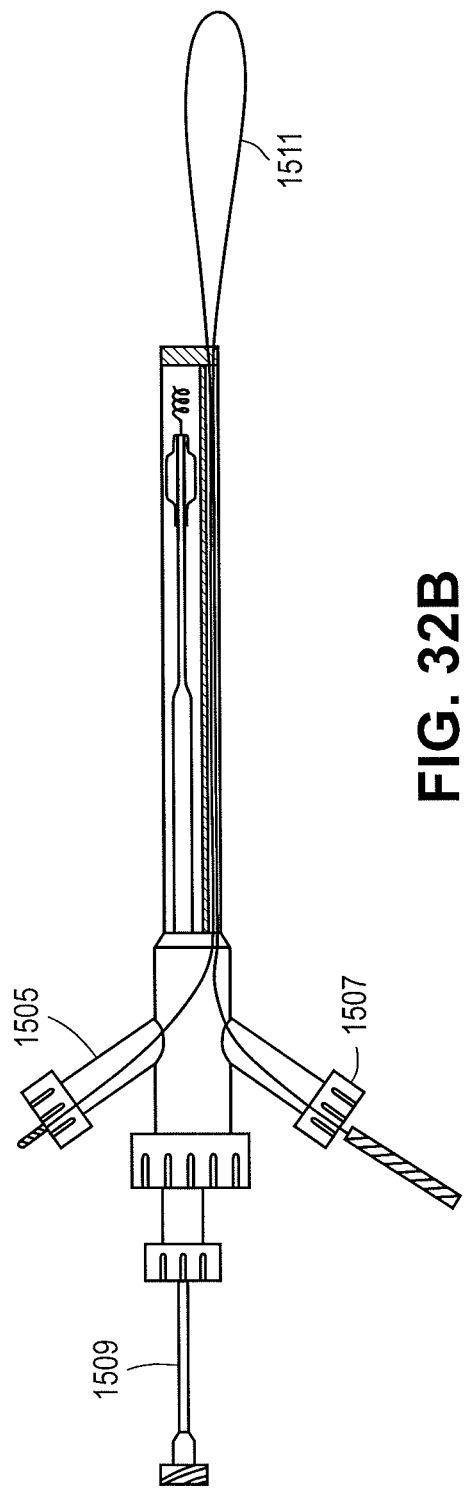
FIG. 32A
FIG. 32B

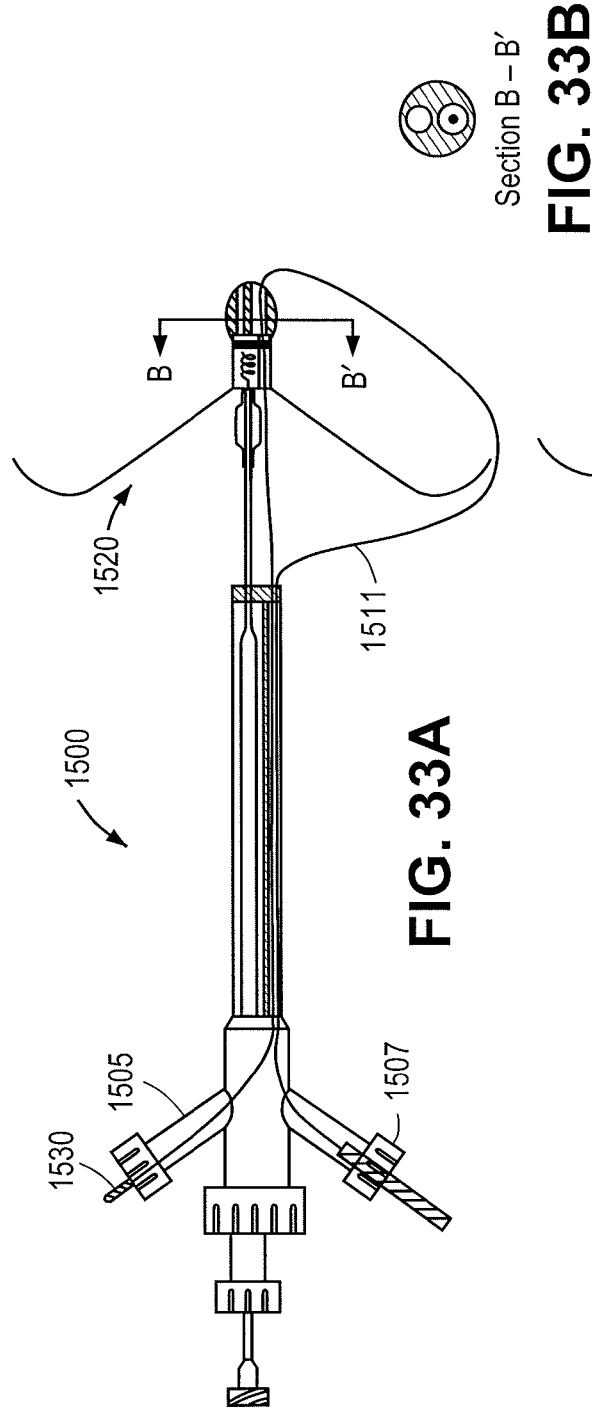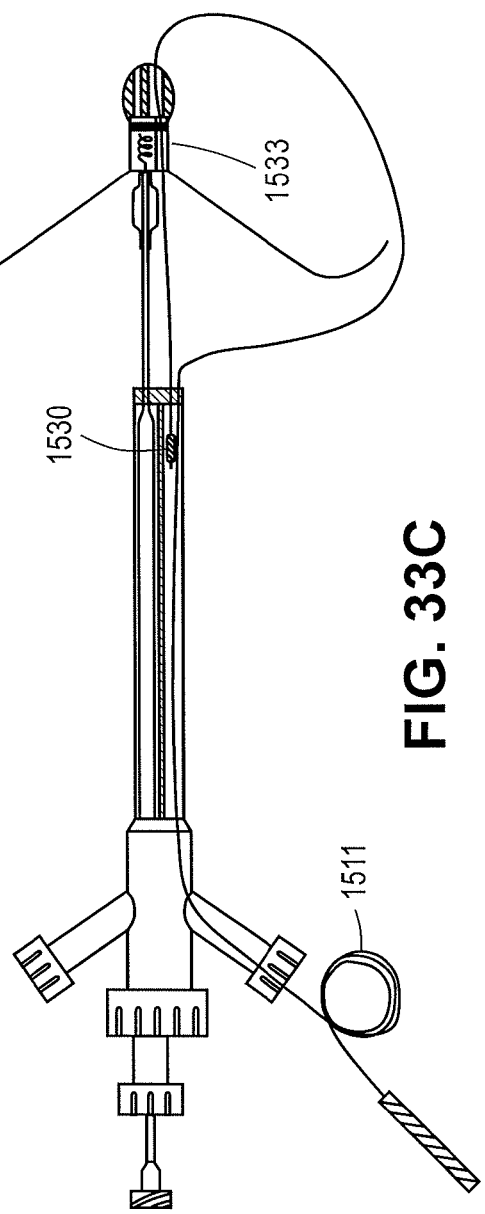
FIG. 33A
FIG. 33B
FIG. 33C

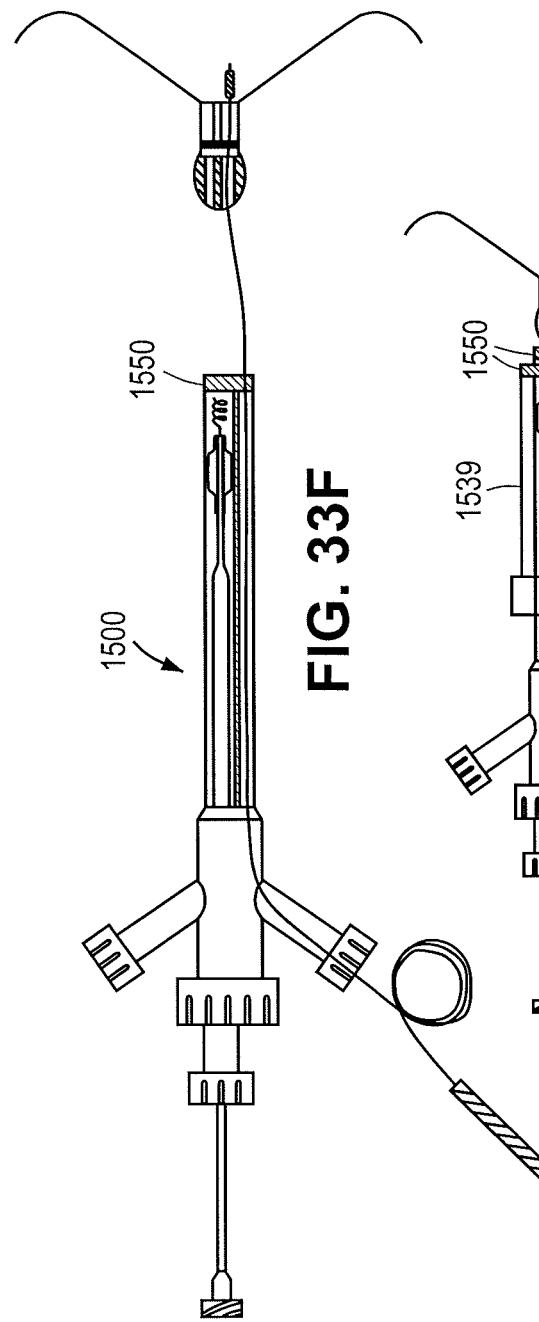

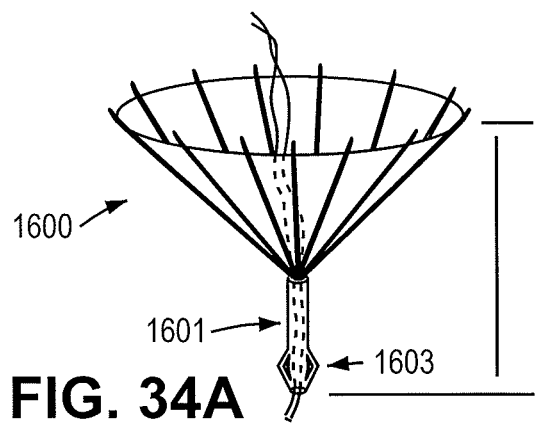
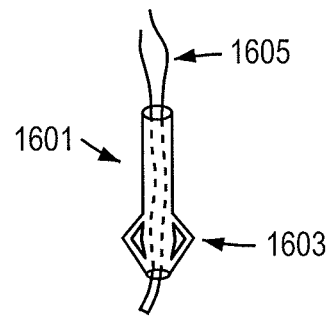
FIG. 34A    FIG. 34B
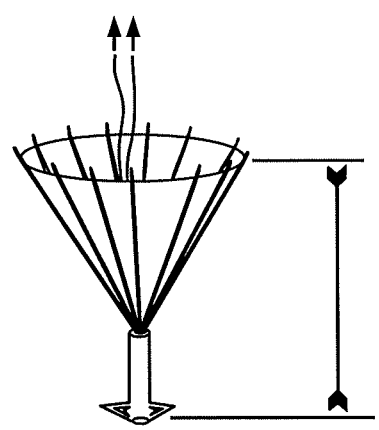
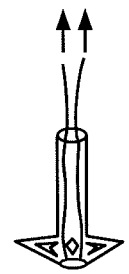
FIG. 34C    FIG. 34D
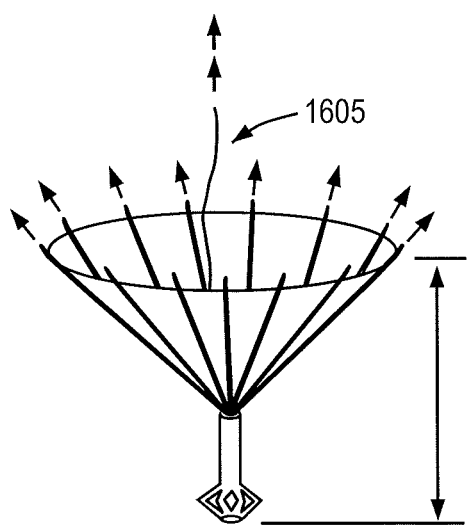
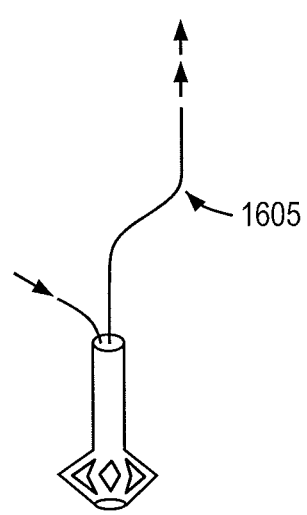
FIG. 34E    FIG. 34F

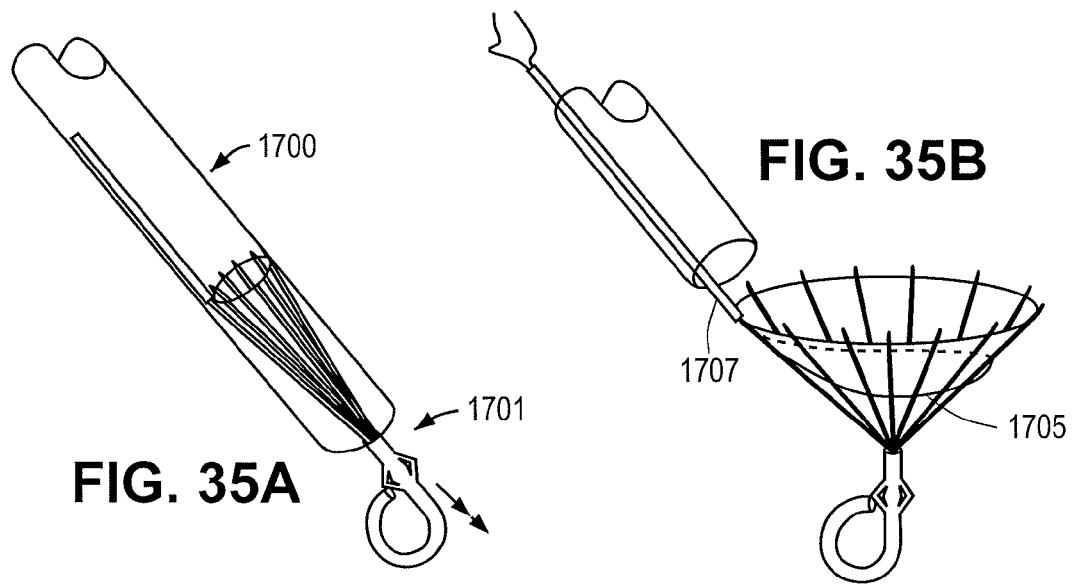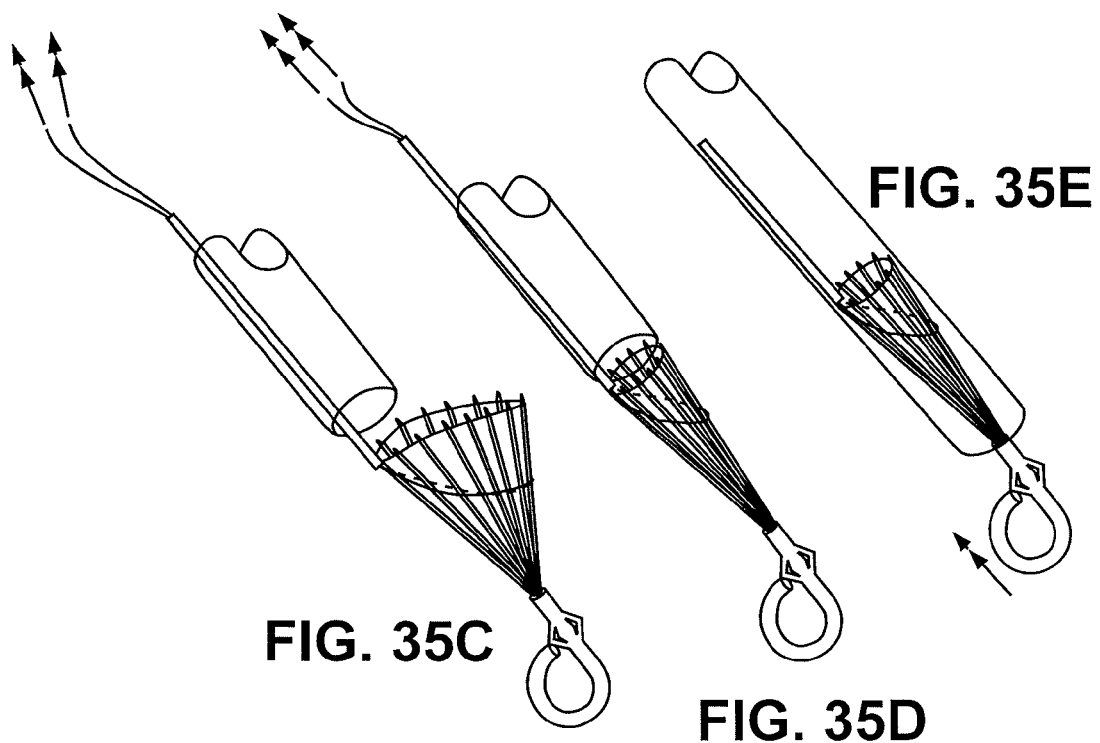

RETRIEVABLE CARDIAC DEVICES

CROSS-REFERENCE TO RELATED APPLICATIONS

This application is a divisional application of U.S. patent application Ser. No. 13/954,221, filed on Jul. 30, 2013, titled "RETRIEVABLE CARDIAC DEVICES," now U.S. Patent Application Publication No. 2013-0317537, which is a divisional of U.S. patent application Ser. No. 13/487,684, filed on Jun. 4, 2012, titled "RETRIEVABLE CARDIAC DEVICES," now U.S. Pat. No. 8,500,790, which is a divisional of U.S. patent application Ser. No. 12/198,022, filed on Aug. 25, 2008, titled "RETRIEVABLE CARDIAC DEVICES," now U.S. Pat. No. 8,246,671, each of which is incorporated herein by reference in its entirety.

This application may be related to U.S. patent application Ser. No. 10/436,959, filed on May 12, 2003, titled "SYSTEM FOR IMPROVING CARDIAC FUNCTION," which is a continuation-in-part of prior U.S. patent application Ser. No. 09/635,511, filed on Aug. 9, 2000, titled "DEVICE AND METHOD FOR TREATMENT OF HOLLOW ORGANS," which claims priority from U.S. Provisional Patent Application No. 60/147,894 filed on Aug. 9, 1999, titled "EXPANDABLE, IMPLANTABLE DEVICE AND METHOD. This application is also a continuation-in-part of U.S. patent application Ser. No. 11/151,164, filed on Jun. 10, 2005, titled "PERIPHERAL SEAL FOR A VENTRICULAR PARTITIONING DEVICE." Each of these patent applications is herein incorporated by reference in its entirety.

BACKGROUND OF THE DISCLOSURE

Described herein are systems, methods and devices for improving cardiac function, and may relate generally to the treating heart disease, particularly congestive heart failure, and more specifically, to a systems, methods, and devices for partitioning a patient's heart chamber.

Congestive heart failure annually leads to millions of hospital visits internationally. Congestive heart failure is the description given to a myriad of symptoms that can be the result of the heart's inability to meet the body's demand for blood flow. In certain pathological conditions, the ventricles of the heart become ineffective in pumping the blood, causing a back-up of pressure in the vascular system behind the ventricle.

The reduced effectiveness of the heart is usually due an enlargement of the heart. A myocardial ischemia may, for example, cause a portion of a myocardium of the heart to lose its ability to contract. Prolonged ischaemia can lead to infarction of a portion of the myocardium (heart muscle) wherein the heart muscle dies and becomes scar tissue. Once this tissue dies, it no longer functions as a muscle and cannot contribute to the pumping action of the heart. When the heart tissue is no longer pumping effectively, that portion of the myocardium is said to be hypokinetic, meaning that it is less contractile than the uncompromised myocardial tissue. As this situation worsens, the local area of compromised myocardium may in fact bulge out as the heart contracts, further decreasing the heart's ability to move blood forward. When local wall motion moves in this way, it is said to be dyskinetic, or akinetic. The dyskinetic portion of the myocardium may stretch and eventually form an aneurysmic bulge. Certain diseases may cause a global dilated myopathy, i.e., a general enlargement of the heart when this situation continues for an extended period of time.

As the heart begins to fail, distilling pressures increase, which stretches the ventricular chamber prior to contraction and greatly increases the pressure in the heart. In response, the heart tissue reforms to accommodate the chronically increased filling pressures, further increasing the work that the now comprised myocardium must perform.

Patients suffering from congestive heart failure are commonly grouped into four classes, Classes I, II, III and IV. In the early stages, Classes I and II, drug therapy is presently the most common treatment. Drug therapy typically treats the symptoms of the disease and may slow the progression of the disease, but it cannot cure the disease. Presently, the only permanent treatment for congestive heart disease is heart transplantation, but heart transplant procedures are very risky, extremely invasive and expensive and are performed on a small percentage of patients. Many patient's do not qualify for heart transplant for failure to meet any one of a number of qualifying criteria, and, furthermore, there are not enough hearts available for transplant to meet the needs of CHF patients who do qualify.

Substantial effort has been made to find alternative treatments for congestive heart disease. For example, surgical procedures have been developed to dissect and remove weakened portions of the ventricular wall in order to reduce heart volume. This procedure is highly invasive, risky and expensive and is commonly only done in conjunction with other procedures (such as heart valve replacement or coronary artery by-pass graft). Additionally, the surgical treatment is usually only offered to Class III and IV patients and, accordingly, is not an option for most patients facing ineffective drug treatment. Finally, if the procedure fails, emergency heart transplant is the only presently available option.

Mechanical assist devices have been developed as intermediate procedures for treating congestive heart disease. Such devices include left ventricular assist devices and total artificial hearts. A left ventricular assist device includes a mechanical pump for increasing blood flow from the left ventricle into the aorta. Total artificial heart devices, such as the Jarvik heart, are usually used only as temporary measures while a patient awaits a donor heart for transplant.

Other efforts to treat CHF include the use of an elastic support, such as an artificial elastic sock, placed around the heart to prevent further deleterious remodeling. Treatment of the heat by mechanical means typically requires accurate and effective placement of treatment devices. Once a treatment device is implanted, it is often difficult (if not impossible) to correct or adjust placement of a treatment device. Furthermore, removal of a treatment device may require further invasive procedures. Thus, it would be beneficial to provide device, systems and methods for removal of cardiac treatment devices that may address these problems.

Described herein are treatment devices that are configured to be removable (or repositionable), systems for removing and/or repositioning such devices, and methods of removing and/or repositioning treatment devices.

SUMMARY OF THE INVENTION

Described herein are devices and systems including removable implants, applicators for inserting, repositioning and/or removing them, and methods of removing them. The implants described herein are cardiac implants that may be inserted into a chamber of a patient's heart, particularly the left ventricle. The implant may support the heart wall. In some variations the implant is a ventricular partitioning device for partitioning the ventricle into productive and non-productive regions.

An implant typically includes a frame comprising a plurality of struts formed of a relatively elastic and biocompatible material. For example, the frame may be formed of a metal or metal alloy. The frame may be formed of a shape memory alloy such as Nitinol. The implant may also include a membrane connected to the frame. The struts of the frame may include a first end that is connected to a hub, and a second end that includes a passive anchor. A passive anchor may be configured to secure the strut to the wall of the heart. For example, the passive anchor may be a sharp tip that is configured to partially penetrate the heart wall. The implant may also include a foot or anchor (including an active anchor) at the distal end.

In general, an implant may be inserted into a heart chamber using an applicator. An applicator typically includes a proximal end which may include a handle and may also include one or more controls for operating the applicator. The applicator may also include an elongate body extending distally. The distal end of the applicator may be adapted for releasably connecting to an implant. For example, the applicator may include an implant stabilization shaft that can connect and release the implant. The applicator may include one or more collapsing elements for collapsing the implant. For example, the applicator may include a lariat or collapse wire for collapsing the struts of the implant. In some variations the applicator includes a collapse sleeve or umbrella/cone for collapsing an implant. In some variations the applicator includes one or more engagement elements for engaging a collapsing element on the implant. For example, the applicator may include a capture wire, hook or the like that may engage a strand or other collapse element (e.g., collapse sleeve) on the implant that can assist in collapsing the struts of the implant.

The implant may also be adapted for disengaging from the wall of the heart. For example, the implant may be shortenable or movable so that any anchors on the implant, such as passive anchors on the struts or an active anchor on distal end, can be disengaged prior to removing the implant. In some variations the implant includes a shortenable region on the stem and/or foot that can be shortened to separate the struts from the heart wall by shortening the length of the stem and/or foot region. Since the implant is typically concave relative to the heart wall, foreshortening the implant in this way may cause passive anchors at the ends of the struts to withdraw from the wall of the heart. In some variations the struts themselves are shortenable. For example, the passive anchors may be retracted, allowing the implant to be removed.

In general, an implant may be removed and/or repositioned after it has been implanted, as described herein. For example, an implant may be positioned at a first location in a heart chamber such as within a cardiac ventricle, the struts forming the implant may be expanded to secure the implant in position. In some variations the implant may partition the chamber (e.g., when a membrane spans the strut regions). In some variations, the implant is disengaged from the applicator prior to repositioning or removal; in other variations, the implant is not disengaged from the applicator prior to repositioning or removal. To remove the implant from the first location in the heart, the implant (e.g., the struts of the implant) is at least partially collapsed. In some variations the implant may first be disengaged from the heart wall. The implant may be collapsed by activating a collapse element on the implant, on the applicator, or both. For example, a strand connected to the struts may be tensioned (e.g., by pulling) to collapse the struts. Thereafter, the implant may be drawn to the applicator. In some variations the implant may be repositioned. In some variations, the implant is withdrawn into a protecting element in the applicator, such as a cannula or sleeve. After repositioning, the implant may be again deployed. Alternatively, the implant may be removed from the patient by withdrawing the implant and actuator from the patient.

For example, described herein is a method of deploying a ventricular partitioning device comprising advancing a ventricular partitioning device having a membrane into a patient's left ventricle chamber in a contracted configuration, expanding the partitioning device into a deployed configuration at a first left ventricle location, at least partially collapsing the partitioning device into the contracted configuration, and withdrawing the partitioning device from the first left ventricle location. The method may also include the step of repositioning the partitioning device within the left ventricle and expanding the portioning device into the deployed configuration at a second left ventricle location so that the partitioning device partitions the left ventricle chamber into a main productive portion of the left ventricular chamber and a secondary, non-productive portion of the left ventricular chamber. In some variations, the method also includes the step of removing the partitioning device from the patient.

The step of expanding the partitioning device may include expanding a frame connected to the membrane. The membrane may be a reinforced membrane.

The step of expanding the partitioning device may include allowing a frame connected to the reinforced membrane to self-expand. Also, as mentioned above, the step of withdrawing the partitioning device may comprise pulling the device into a retrieval catheter.

In any of the variations described herein, the implant (e.g., the ventricular partitioning device) may be secured or anchored to the first left ventricle location, and after repositioning, may be anchored to the second location.

The method may also include a step of disengaging the ventricular partitioning device from the left ventricle in the first location. For example, any anchors on the implant may be collapsed, withdrawn, or otherwise removed. Thereafter, or simultaneously, the step of at least partially collapsing the partitioning device into the contracted position may comprise pulling on at least one strand connected to the partitioning device. In some variations, the step of at least partially collapsing the partitioning device into the contracted position comprises drawing a collapse sheath at least partially over the partitioning device.

Also described herein are methods of deploying a ventricular partitioning device including the steps of: advancing a ventricular partitioning device having a membrane into a patient's left ventricle chamber in a contracted configuration, expanding the partitioning device into a deployed configuration at a first left ventricle location, pulling on a strand in communication with the partitioning device to at least partially collapse the partitioning device into the contracted configuration after it has been expanded, retrieving the partitioning device into a retrieval catheter; and withdrawing the partitioning device from the first left ventricle location.

The step of pulling on a strand in communication with the partitioning device may include pulling on an expansive strand extending from the periphery of the reinforced membrane. The step of pulling on the stand in communication with the partitioning device may include pulling on a retrieval wire at least partially surrounding the expanded reinforced membrane.

Also described herein are devices for partitioning a chamber of a patient's heart into a main functional portion and a secondary non-functional portion. These devices (implants) may include: a membrane having a collapsed configuration for delivery through a delivery catheter and an expanded configuration for deployment within the heart chamber so as to partition the heart chamber into a main functional portion and a secondary non-functional portion, an expandable frame formed of a plurality of struts having a distal end secured to a hub, wherein the membrane is secured to the expandable frame, a distally extending stem, and a collapse element configured to convert the partitioning component from the expanded configuration to the folded configuration.

The collapse element may be a collapse sheath, a strand extending around the periphery of the partitioning component and extending therefrom, or the like.

Also described herein are devices for partitioning a chamber of a patient's heart into a main functional portion and a secondary non-functional portion that include: a membrane having an expanded configuration and a collapsed configuration, wherein the membrane forms a recess when in the expanded configuration, an expandable frame formed of a plurality of struts having a distal end secured to a hub, wherein the reinforced membrane is secured to the expandable frame, a non-traumatic distal tip, configured to engage a region of the ventricular wall; and a strand extending at least partially around the periphery of the membrane at or near the proximal end of the expandable frame, wherein the strand is configured to be tensioned to collapse the device from the expanded configuration to the collapsed configuration.

Also described herein is a system for partitioning a chamber of a patient's heart into a main functional portion and a secondary non-functional portion, the system comprising an implant configured for deployment into a heart chamber and an elongate applicator configured to insert and retrieve the implant. For example, the implant may include a plurality of struts, wherein the struts are configured to have a collapsed delivery configuration and an expanded deployed configuration, and a strand extending between the struts, wherein the strand may be tensioned to collapse the struts. The elongate applicator configured to insert and retrieve the implant may include a control at the proximal end of the applicator for controlling release of the implant from the applicator, and an elongate body extending from the proximal end to a distal end, wherein the distal end of the elongate body is configured to relaseably secure the implant. The strand extends proximally from the implant along the elongate body of the applicator so that the strand may be manipulated from the proximal end of the applicator.

The applicator may further comprise a port at the proximal end through which the strand may pass. In some variations, the applicator includes an implant capture element at the distal end of the applicator. The implant capture element may be selected from the group consisting of: an implant capture sleeve and an implant capture umbrella.

Also described herein are methods of deploying, repositioning and/or removing an implant comprising: advancing an implant into a patient's left ventricle chamber in a contracted configuration, wherein the implant comprises a plurality of struts formed of a shape memory material, expanding the implant into a deployed configuration at a first left ventricle location, changing the temperature of the implant to at least partially collapse the implant into the contracted configuration, retrieving the implant into a retrieval catheter, and withdrawing the implant from the first left ventricle location. In some variations, the step of changing the temperature of the implant comprises exposing the implant to cooled saline.

Also described herein are systems for partitioning a patient's ventricle, comprising: an implant configured for deployment into the patient's ventricle, the implant including a plurality of struts, wherein the implant is configured to have a collapsed delivery configuration and an expanded deployed configuration, and an applicator configured to insert and retrieve the implant, comprising a control at the proximal end of the applicator for controlling release of the implant from the applicator, an elongate body extending from the proximal end to a distal end, wherein the distal end of the elongate body is configured to releasably secure the implant, and a capture wire extendable from the applicator's distal end and configured to draw the implant toward the applicator's distal end. The applicator may also include a control at the proximal end for manipulating the capture wire.

In some variations, the capture wire is configured as a lariat. In some variations, the implant includes a strand that may be tensioned to collapse the implant from the expanded configuration, and the capture wire of the implant is configured as a hook that may engage the strand. The capture wire may be connected to the implant.

In some variations, the applicator further comprises an inflatable sleeve configured to extend from the distal end of the applicator and collapse the implant. As mentioned above, the applicator may include a capture umbrella configured to extend from the distal end of the applicator and collapse the implant.

The implant may also include collapse sleeve configured to collapse the struts. Thus, an applicator may include a collapse sleeve pullwire configured to engage the collapse sleeve on the implant.

Also described herein are systems for partitioning a patient's ventricle, the system comprising: an implant configured for deployment into the patient's ventricle and an elongate applicator configured to insert and retrieve the implant. The implant may include a plurality of struts, wherein the implant is configured to have a collapsed delivery configuration and an expanded deployed configuration, and a strand extending between the struts, wherein the strand may be tensioned to collapse the struts. The elongate applicator configured to insert and retrieve the implant may include a control at the proximal end of the applicator for controlling release of the implant from the applicator, an implant stabilization shaft extending distally from the proximal end, wherein the implant stabilization shaft is configured to releasably secure to the implant, and a strand capture element extending distally from the proximal end, wherein the strand capture element is configured to engage the strand on the implant and collapse the struts of the implant.

Also described herein are devices for partitioning a patient's ventricle into a main functional portion and a secondary non-functional portion that include: a membrane having an expanded configuration and a collapsed configuration, an expandable frame formed of a plurality of struts having a distal end secured to a hub, wherein the membrane is secured to the expandable frame, a stem extending distally from the hub, and a collapse sleeve configured to axially slide from the stem and to collapse the expandable frame and membrane into a collapsed configuration. These devices may also include a passive anchor at the ends of each of the struts of the expandable frame.

In some variations the devices include a non-traumatic foot at the distal end of the device. The devices may also include an attachment mechanism for a collapse sleeve pullwire.

Also described herein are removable or repositionable implants for partitioning a chamber of a patient's heart into a main functional portion and a secondary non-functional portion, comprising: a membrane, a plurality of struts secured to a hub at a first end, wherein the membrane is secured to the plurality of struts, and the plurality of struts and membrane have a collapsed delivery configuration and an expanded deployed configuration for deployment within a heart chamber, wherein the membrane forms a recess when in the expanded configuration, wherein end of each of the plurality of struts includes a passive anchor configured to secure to the wall of the patient's heart, and a stem extending distally from the hub, wherein the stem comprises a shortenable region configured to be decreased in length and permit the passive anchors to disengage from the wall of the patient's heart.

In some variations, the implant further includes a trigger configured to shorten the shortenable region of the stem. The trigger comprises a wire or line extending distally through the stem portion.

The shortenable region may be a collapsible region, or a telescoping region. In some variations, the device includes a lock for locking the shortenable region.

Also described herein are methods of removing an implant that has been deployed at a first ventricle location, wherein the implant includes a plurality of struts each having a passive anchor at a first end and connected to a hub at a second end and a stem extending from the hub. The method may include the steps of: shortening a shortenable region of the stem to disengage the passive anchors from the heart wall, at least partially collapsing the plurality of struts, and withdrawing the implant from the first left ventricle location.

In some variations, the step of shortening the shortenable region comprises applying pulling on a wire or string to shorten the shortenable region. The method may also include the step of unlocking the implant so that the shortenable region may be shortened. The step of at least partially collapsing the implant may include pulling on a strand or collapse line to draw the struts together.

The method may also include the step of repositioning the implant within the left ventricle and expanding the struts into a deployed configuration at a second left ventricle location. In addition, the method may also include the step of removing the implant from the patient.

INCORPORATION BY REFERENCE

All publications and patent applications mentioned in this specification are herein incorporated by reference in their entirety as if each individual publication or patent application was specifically and individually indicated to be incorporated by reference.

BRIEF DESCRIPTION OF THE DRAWINGS

FIG. 3A is a side view of the system of FIG. 2A with the cardiac device further retracted.

FIG. 3B is a cross-sectional side view of a portion of FIG. 3A.

FIG. 15 is a schematic elevational view, partially in section, of a delivery system with the partitioning device shown in FIGS. 8 and 9 mounted thereon.

FIG. 16 is a transverse cross-sectional view of the delivery system shown in FIG. 15 taken along the lines 16-16'.

FIG. 17 is an elevational view, partially in section, of the hub shown in FIG. 12 being secured to the helical coil of the delivery system shown in FIG. 15.

FIG. 20A is a partial schematic view of the partitioning device shown in FIGS. 8 and 9 in a contracted configuration resulting from pulling the free ends of the expansive strand at the periphery of the reinforced membrane.

FIG. 20B is a schematic view of the contracted device shown in FIG. 20A being pulled into an expanded distal end of an applicator to facilitate withdrawal of the partitioning device.

FIG. 20C is a schematic view of the contracted device shown in FIG. 20A pulled further into the inner lumen of the receiving applicator.

FIG. 23A illustrates another variation of an applicator.

FIG. 23B shows a cross-section through a region of the applicator of FIG. 23A.

FIGS. 24A-24F illustrate a method of using the applicator similar to that shown in FIG. 23A to retrieve an implant.

FIGS. 32A and 32B show another variation of an applicator configured for retrieval of an implant.

FIG. 33A and FIG. 33C-33H illustrate operation of an applicator similar to that shown in FIGS. 32A and 32B, and FIG. 33B shows a cross-section through a region of the applicator shown in FIGS. 33A and 33C-33H.

FIGS. 34A, 34C and 34E show an implant having a shortenable stem region. FIG. 34C shows the implant of FIG. 34A in which the stem region has been shortened by tensioning an activating element. FIG. 34E shows the implant of FIGS. 34A and 34C during removal of the activating element. FIGS. 34B, 34D and 34F show a slightly enlarged view of the stem regions of the implants of FIGS. 34A, 34C and 34E, respectively.

FIGS. 35A-35E illustrate the operation of another system for deploying and removing an implant. The system includes an applicator (partially illustrated in FIGS. 35A-35E) and an implant.

DETAILED DESCRIPTION

Described herein are deployable and retrievable cardiac treatment devices or implants, systems including retrievable devices, and methods of using them. For example, any of the implants described herein may be positioned in a patient's heart (and particularly the patient's ventricle, such as the left ventricle), deployed into the heat by expanding the device, and then, either immediately or after some time period, disengaged from the heart, at least partially collapsed, and repositioned and/or removed. The implants, which may also be referred to as cardiac treatment devices, may be configured to partition the heart (e.g., into a productive and non-productive region), or to support the wall of the heart. Examples of such implants are described herein. Applicators for deploying and/or retrieving any of the implants described herein are also taught, as are systems including the applicators and the implants. Methods of using these implants are also described.

Figure 1:
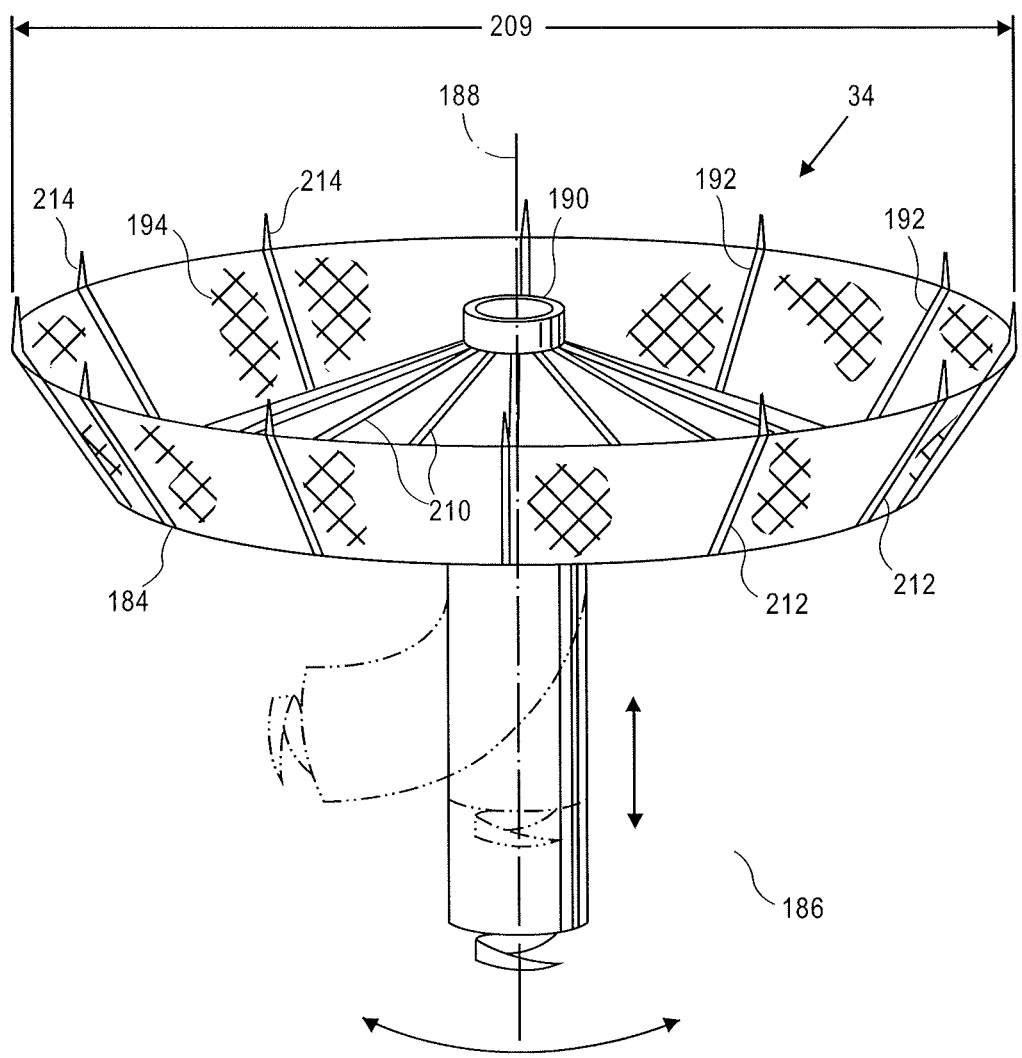
FIG. 1 is a perspective view of one variation of a cardiac treatment device including a hub, a frame, and a stem thereof.
Figure 2A:
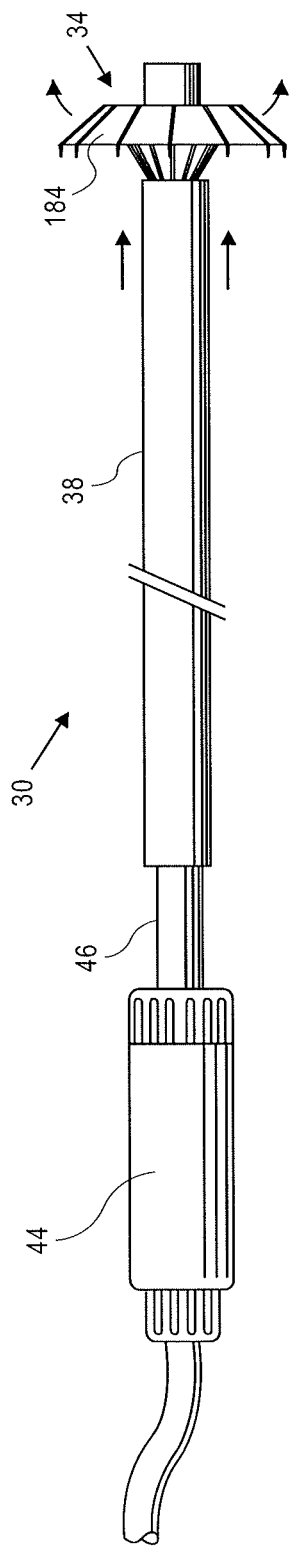
FIG. 2A is a cross-section of a system including a cardiac device with the cardiac device partially retracted into an applicator (e.g., delivery catheter).
Figure 2B:
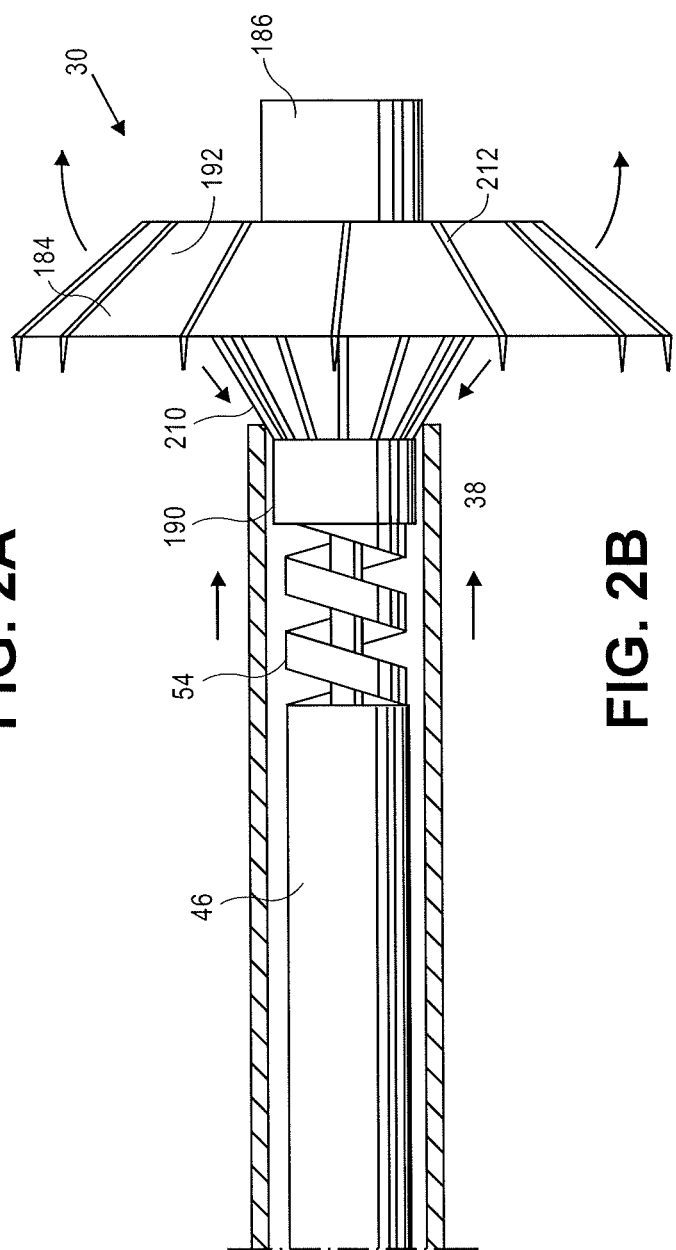
FIG. 2B is a cross-sectional side view of a portion of FIG. 2A.

FIGS. 1, 6A, 7A and 8 show variations of implants (e.g., device 34 in FIG. 1). Any of the implants described herein may also be referred to as cardiac treatment devices or treatment devices. Alternatively, these devices may be referred to as ventricular partitioning devices or partitioning devices. Such partitioning devices may be configured to partition a ventricle into function (or productive) and non-function (or non-productive) regions. FIGS. 2A-2B, and 3 illustrate this implant (cardiac device 34) in more detail. The cardiac device 34 includes a frame 184 and a stem 186, or flexible body, and has a vertical axis 188. Partitioning devices, including ventricular partitioning devices, are only one class of implants which are described herein and may be used with the device removal or repositioning systems and methods described herein. Other such devices may be support devices that do not include a membrane, or do not partition a heart chamber, but predominantly support the cardiac tissue.

Referring now to FIG. 1, the frame 184 includes a frame hub 190, a plurality of main segments 192, and a membrane 194. The hub 190 in this example is a ring-shaped body with an outer surface with a diameter of about 5 mm, an inner surface with a diameter of about 4 mm, a thickness of about 3 mm, and a pin extending off-center across the inner surface creating a smaller and a larger gap. The pin has a length of about 3.5 mm and a diameter of about 1 mm and is located in a plane. The frame 184 has a diameter 209 of approximately 75 mm, however, other embodiments may have diameters of between 10 mm and 120 mm. The entire hub 190 in this example is made of nickel titanium.

In this example, the main segments 192 include first portions, or central segments, 210, second portions, or outer segments, 212, and passive anchors 214. The first portions 210 are connected to the hub 190 at a central portion of the outer surface and extend radially from the hub 190 at an angle away from the plane of the pin to a length of about 8 mm. The second portions 212 of the segments 192 are connected to ends of the first portions 210 and further extend radially from the hub 190 but at an angle towards the plane. The second portions 212 each have a length of 5-50 mm. The passive anchors 214 are formed at an end of each of the second portions 212. The passive anchors 214 have sharp ends that point slightly radially from the hub 190. The segments 192 are made from nickel titanium, which after a prescribed thermal process, allows for the segments 192 to hold their shape as illustrated in FIG. 1. The entire frame 184, or just portions of the frame 184, may also be made of stainless steel, polymers, or biodegradable material(s).

In FIG. 1, the membrane 194 is stretched over the first 210 and second 212 portions of the segments 192 to give the frame 184 a disk like shape. The membrane 194 is made of expanded Polytetrafluoroethylene (ePTFE) and has a thickness of about 0.08 mm. Other embodiments may use a mesh membrane, or other appropriate permeable, semi-permeable, or impermeable membranes. While porous ePTFE material may be preferred, the membrane may be formed of suitable biocompatible polymeric material which includes Nylon, PET (polyethylene terephthalate) and polyesters such as Hytrel. The membrane may be foraminous in nature to facilitate tissue ingrowth after deployment within the patient's heart. The applicator (including delivery catheter and/or a guiding catheter) may be formed of suitable high strength polymeric material such as PEEK (polyetheretherketone), polycarbonate, PET, Nylon, and the like. Braided composite shafts may also be employed.

The stem 186 may be made of Polytetrafuoroethylene (PTFE) and is thus expandable and flexible. Referring again to FIG. 1, the stem 186 can be compressed or stretched by 30% of its length and can be bent from the vertical axis 188 of the device 34 by 90 degrees in any direction. The first hub 232, second hub 234, and active anchor 236 may be made of nickel titanium. In other embodiments, the hubs may be made of stainless steel.

FIG. 2A illustrates one variation of a systems including an applicator 30 and an implant 34. The implant shown is the variation described above from FIG. 1. The applicator shown in FIG. 2 includes a handle 44, a deployment member 46, which is partially within a catheter region (catheter tube 38). The proximal end of the deployment member 46 is secured to the handle 44. The handle may include one or more controls for deploying and/or retrieving an implant. For example, the handle may be formed of molded plastic and may include knobs, buttons, or other controls for operating the applicator to deploy or retrieve a device. The distal end of a portion of the applicator (e.g., the deployment member 46) may be adapted to releasably grasp the implant.

In use, the deployment member 46 may be inserted through the catheter tube 38 so that the distal end 54 of the deployment member 46 may exit the distal end of the tube 38. The deployment member 46 may connect to a cardiac implant device 34 such that a key (not visible) engages the hub 190 of the frame 184 of the implant by passing through the larger gap in the hub 190. The implant may then be secured to the deployment member, and may be deployed by manipulation of a control on the handle, e.g., by rotating the key to disengage the implant from the deployment member.

As illustrated in FIGS. 2A and 2B, the distal end 54 of the deployment member 46 may be pulled into the distal end of the catheter tube 38. As a proximal section of the frame 184 of the implant enters the catheter tube 38, it may be collapsed by the smaller diameter of the catheter opening of the applicator. For example, in the variation shown in FIG. 2, the first portions 210 of the segments 192 begin to collapse towards the stem 186 when the implant is drawn into the catheter tube. The segments 192 collapse, or fold, against a spring force that is created by the resilient nature of the nickel titanium material from which they are made. At the same time, the second portions 212 fan out radially away from the hub 190.

Figure 4A:
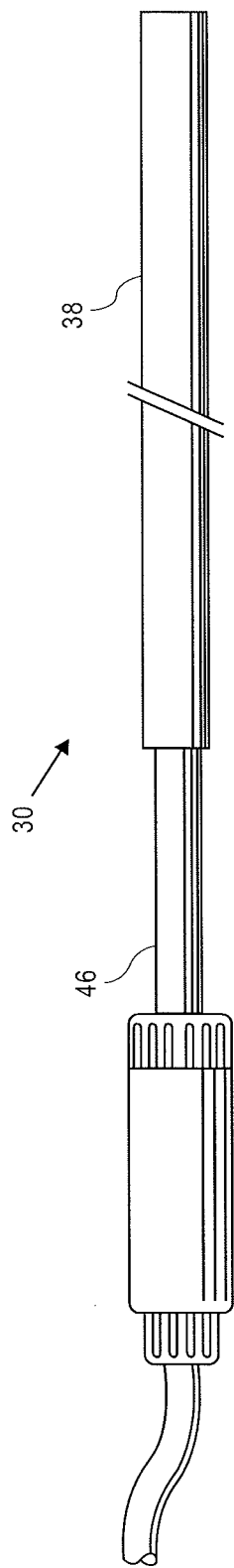
FIG. 4A is a side view of the system of FIG. 2A with the cardiac device fully retracted.
Figure 4B:
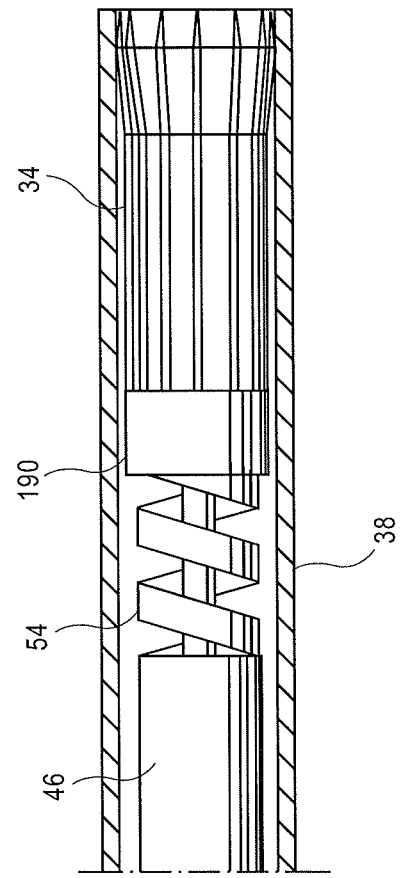
FIG. 4B is a cross-sectional side view of a portion of FIG. 4A.

FIGS. 3A and 3B show a distal section of the frame 184 and the second portions 212 of the segments 192 beginning to enter the tube 38, so that the second portions have been bent back to collapse towards the stem 186 similarly to the first portions 210. FIGS. 4A and 4B illustrate this system 30 with the cardiac implant device 34 completely contained within the catheter tube 38.

FIGS. 5A-5J illustrate a human heart 242 while the implant 34 is being deployed. The heart 242 contains a right ventricle 244 and a left ventricle 246 with papillary muscles 248 and an akinetic (e.g., damaged) portion 250 with an apex 252. The distal end of the catheter 38 has been inserted through the aorta and aortic valve into the left ventricle 246 to a selected position where the ventricular partitioning device 34 can be deployed. The catheter tube 38 is then partially pulled off of the cardiac device 34 exposing the stem 186.

Figure 5A:
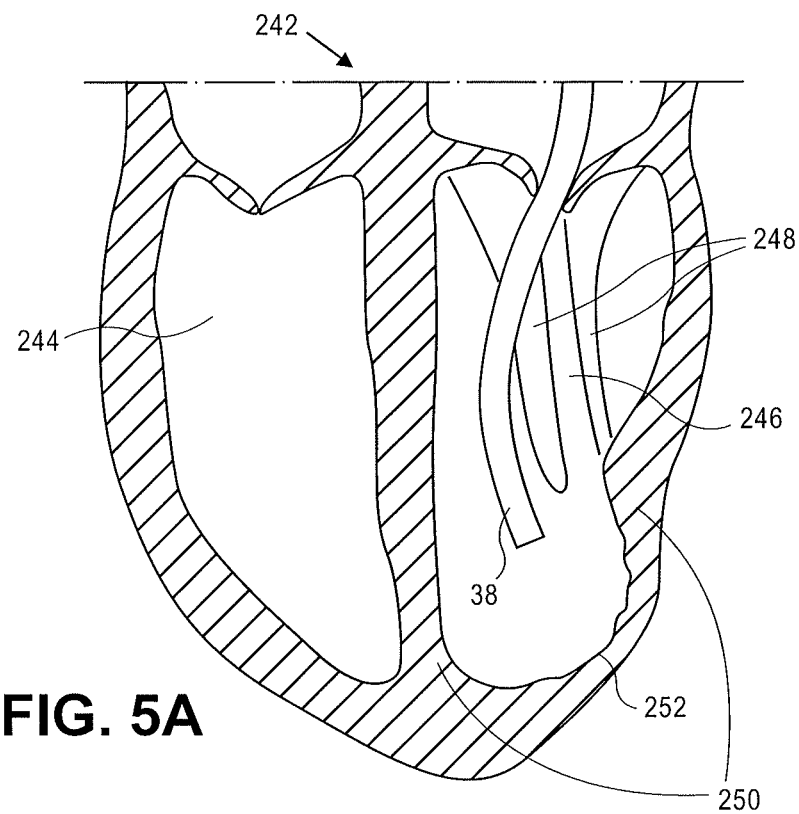
FIG. 5A is a cross-sectional side view of a human heart with a portion of an applicator inserted therein.
Figure 5B:
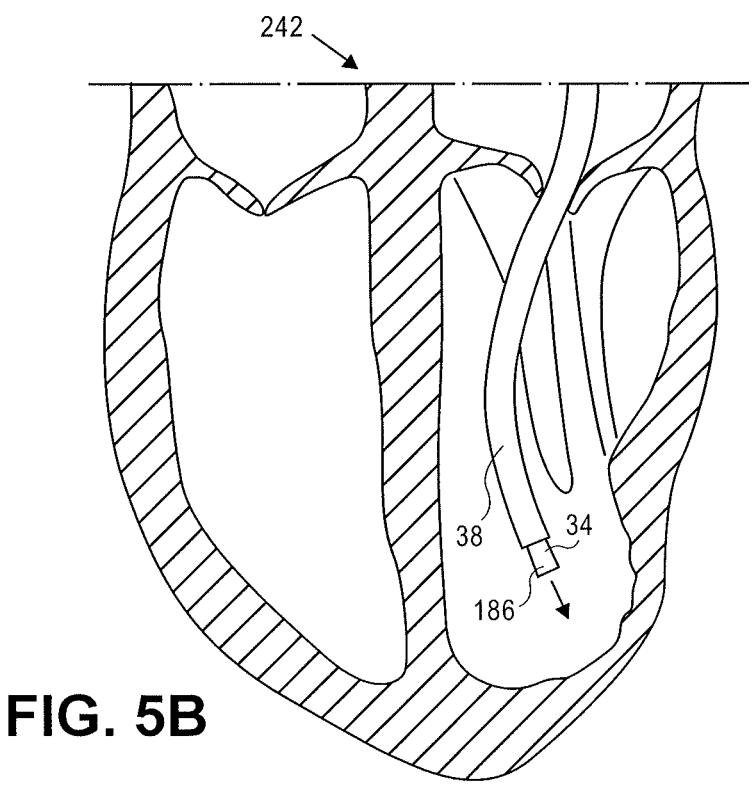
FIGS. 5B-5K are cross-sectional side views of the human heart illustrating installation (FIGS. 5B-5E), removal (FIGS. 5E-5H), and subsequent final installation (FIGS. 5I-5K) of a cardiac device.
Figure 5C:
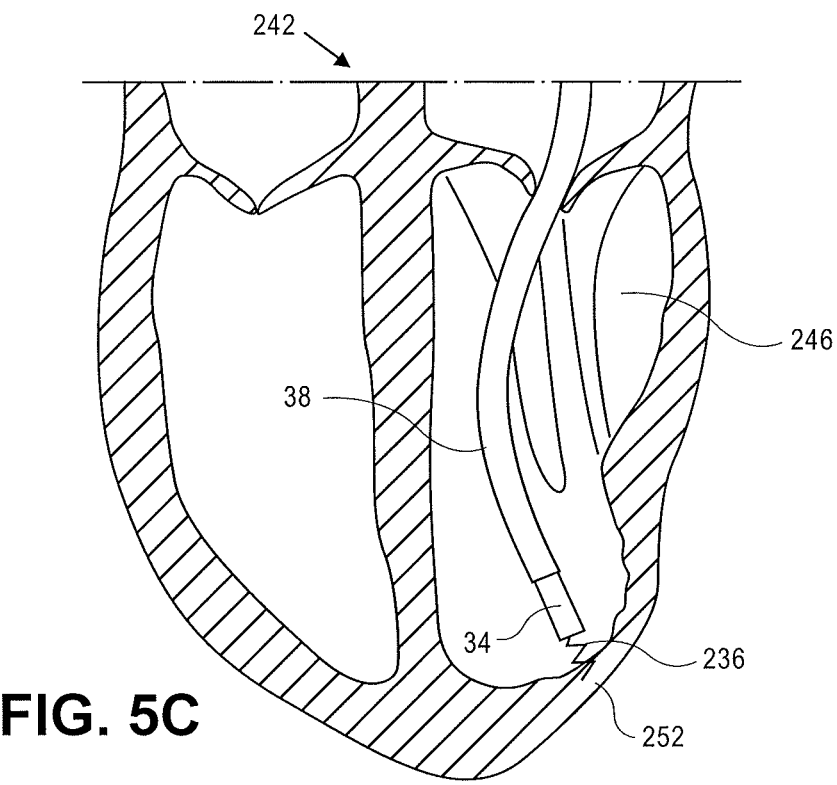
Figure 5D:
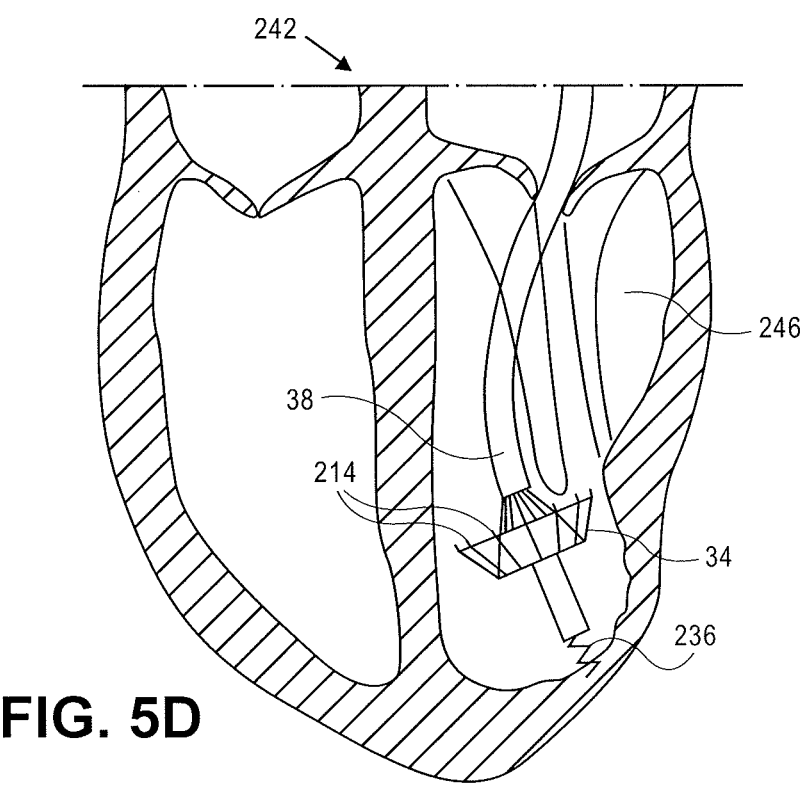
Figure 5E:
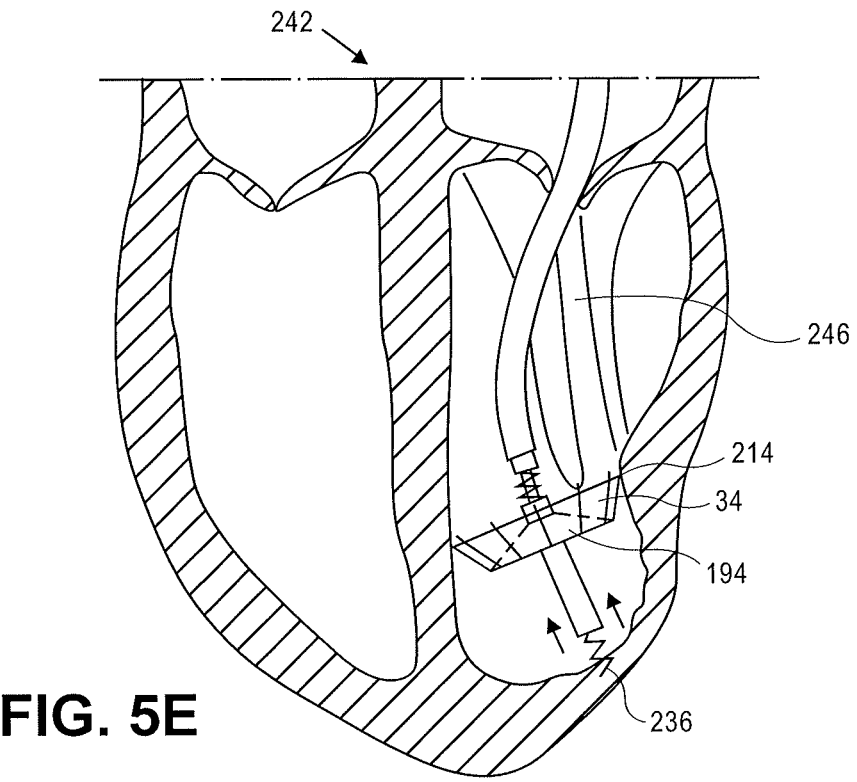

The active anchor 236 is then deployed. In the implant shown in FIGS. 1-5J, the implant includes an active anchor at the distal end. This anchor may be inserted into the tissue as illustrated in FIG. 5C. In other variations (e.g., described below), the distal end of the implant may be configured with one or more atraumatic feet that does not penetrate the tissue. In FIG. 5C, the active anchor at the distal end may be deployed into the tissue by operating (e.g., rotating) a control (e.g. an anchor knob) on the handle of the device. The active anchor 236 penetrates the myocardium of the heart 242 to secure the cardiac device 34 in the selected position at the apex 252 of the akinetic portion 250 of the left ventricle 246.

The catheter 38 is then completely removed from the distal end 54 of the deployment member 46, exposing the cardiac device 34. As the cardiac device 34 expands, due to the resilient nature of the segments 192, and the pre-set shape of the frame 184, the passive anchors 214 on the segments 192 penetrate the myocardium in a first direction. The membrane 194 seals a portion of the ventricle 246 and separates the ventricle 246 into two volumes.

If the cardiac device 34 has not been properly positioned, or if it is of the wrong size or shape for the particular heart, the device 34 may be repositioned or completely removed from the heart 242, as illustrated in FIGS. 5E-5H.

For example, in variations in which an active anchor at the distal end has been used, the implant may be removed by first releasing the active anchor. If the implant has been completely deployed, e.g., so that the applicator has been separated from the implant (which has been inserted into the tissue), then the implant may re-coupled to the applicator. For example, the distal end of a portion of the applicator, such as the deployment member 46, 54, may be connected to the implant. Thus, in FIG. 5E, the applicator has been re-coupled to the deployment member 46 of the applicator. A control (e.g., knob, etc.) on the handle may be manipulated to engage the applicator to the implant. In this variation a central portion of the implant, such as the hub, is configured to releasably engage and re-engage the applicator. In some variations an additional tether or other element may be used to grab and position the deployed implant so that it can be engaged with the applicator. Examples and illustrations of these additional elements are provided in greater detail below.

Furthermore, the device may be repositioned before disengaging from the applicator.

Figure 5F:
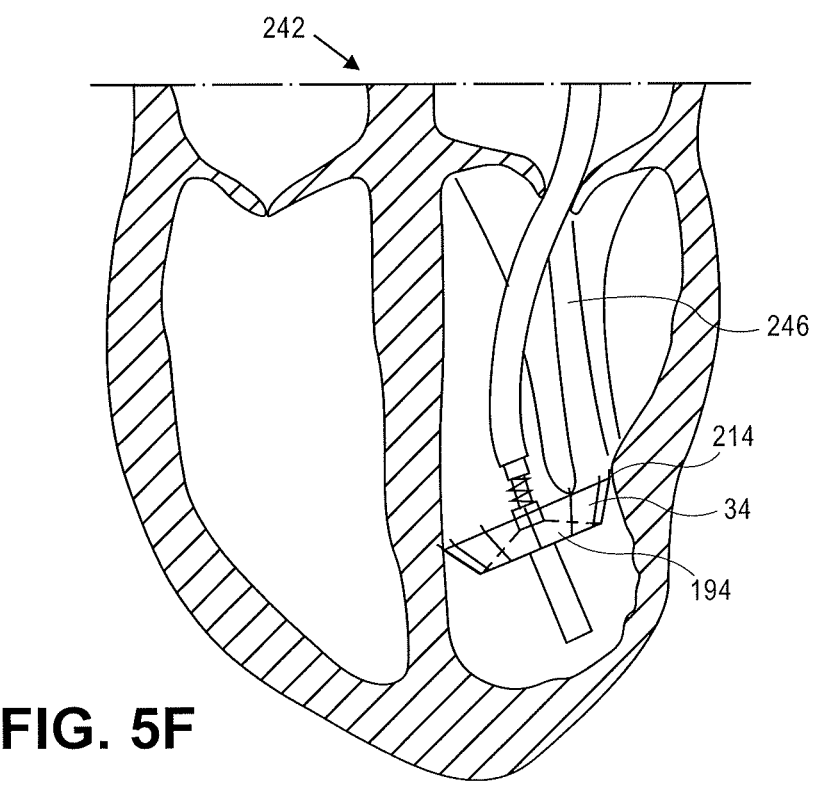
Figure 5G:
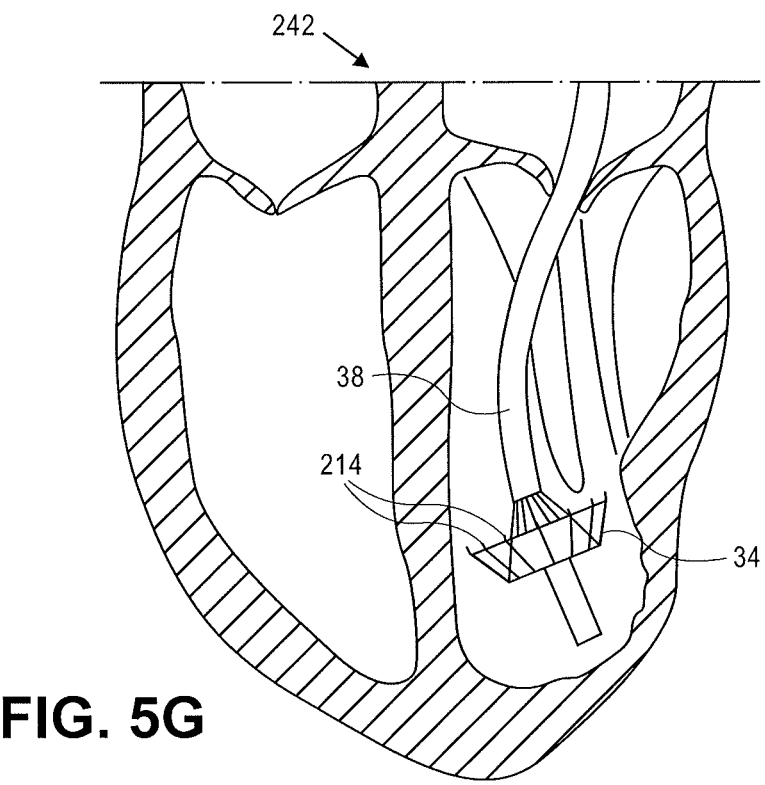
Figure 5H:
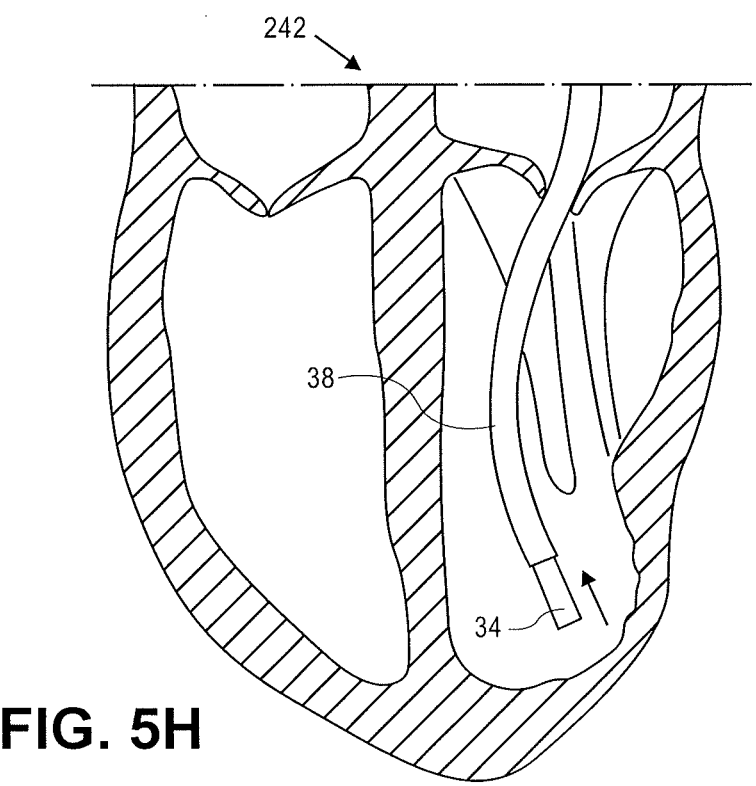

After the applicator has been engaged with the implant (or before disengaging the implant), activation of a control on the applicator (e.g., rotation of an anchor knob on the handle of the applicator) may disengage the active anchor 236 from the left ventricle 246. The distal end 54 of the deployment member 46 may be retracted into the catheter 38 to once again fold the cardiac device 34 into the position shown in FIG. 4B, from where it can again be deployed. The passive anchors 214 may be removed from the myocardium in a second direction which is approximately 180 degrees from the first direction so that minimal damage is done to the myocardium. This is illustrated in FIGS. 5F-5H.

Figure 5I:
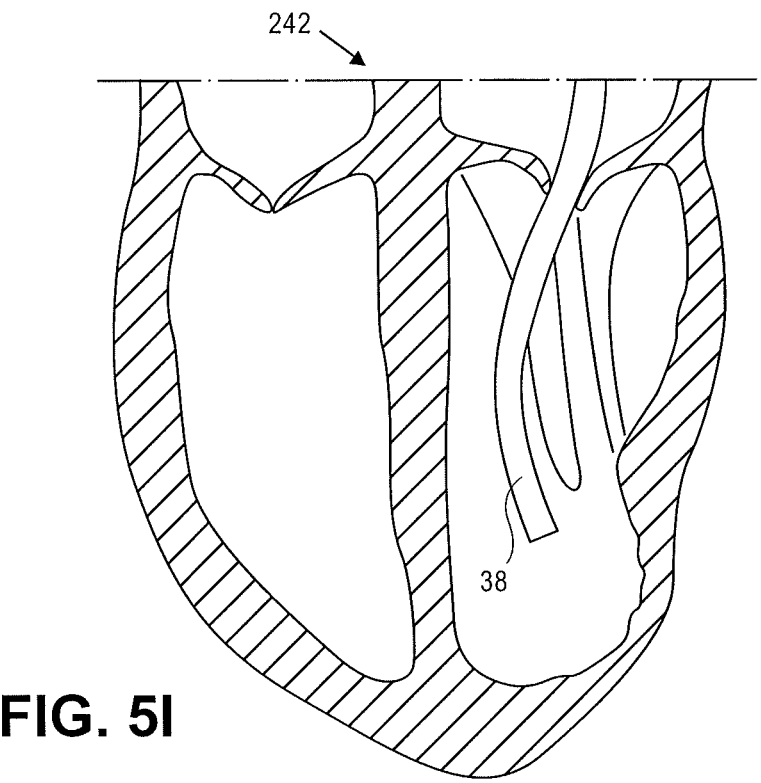
Figure 5J:
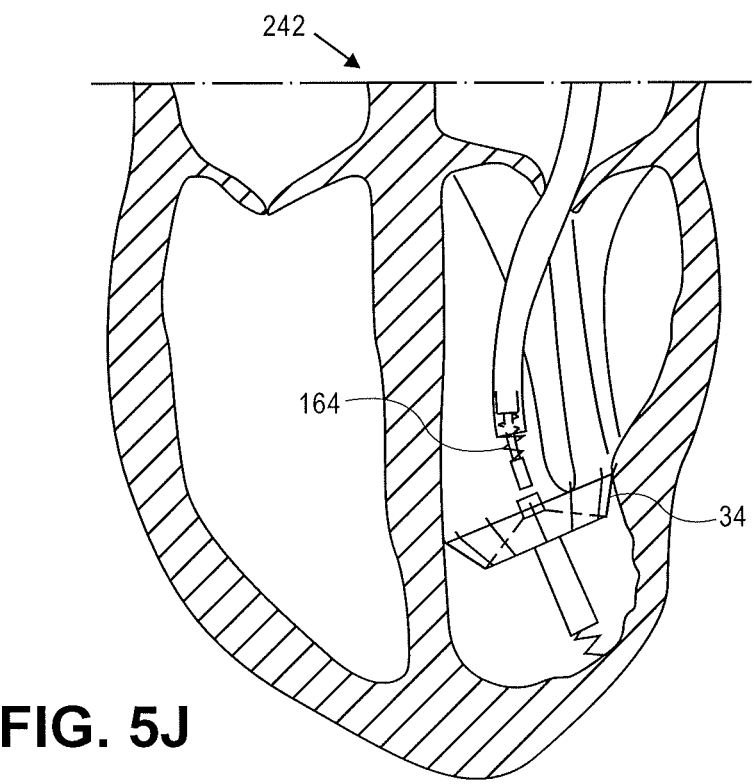
Figure 5K:
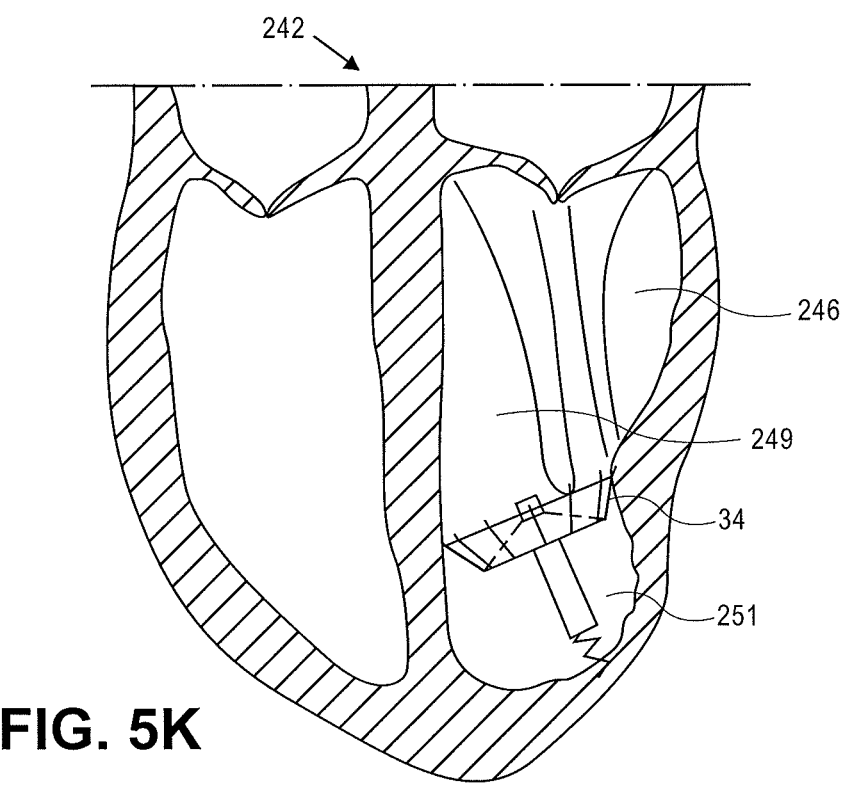

The implant 34 may then be properly re-positioned, as shown in FIG. 5I, and deployed in the new location using the applicator. Once positioned, the applicator may be activated to release the deployment member 46 as previously described. After deploying it as desired, the distal end of the applicator may be separated from the cardiac device 34 to allow removal of the deployment member 46 and removal of the applicator from the heart 242, as shown in FIG. 5J. FIG. 5K illustrates the heart 242 with the cardiac device 34 installed and the deployment mechanism 36 removed from the heart 242.

In this variation, the shape of the frame 184 allows the device 34 to be retrieved as long as the deployment member 46 is connected to the device 34. When the device 34 is retrieved, the passive anchors 214 withdraw from the myocardium in a direction that is approximately 180 degrees from, or opposite, the first direction to minimize the amount of damage done to the myocardium. The device 34 also provides support for the akinetic region 250, minimizes the bulging of the akinetic region 250, and reduces stress on the working parts of the myocardium. In general, the ePTFE membrane which may be used with the implants is biocompatible, has a non-thrombogenic surface, promotes healing, and accelerates endothelization. These membranes may be used to partition the heart, as previously described.

Figure 6A:
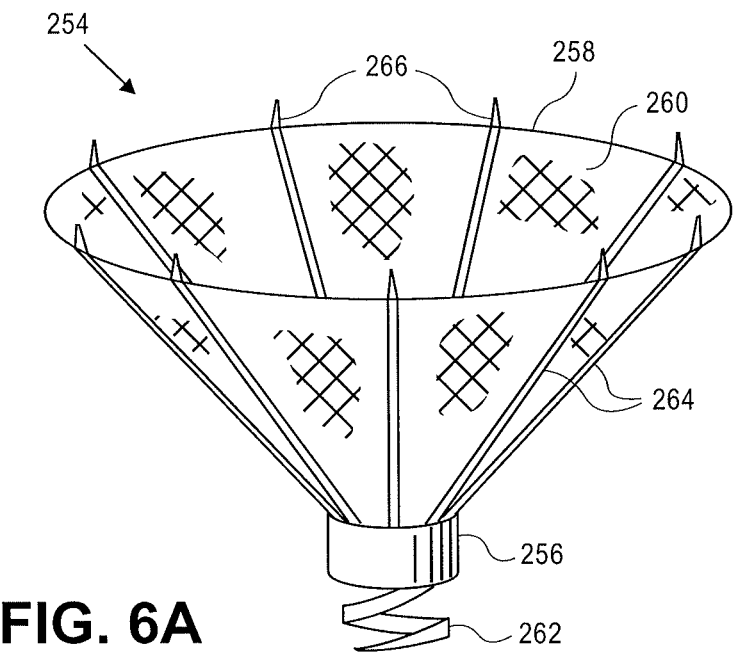
FIG. 6A is a perspective view of another variation of a cardiac device.

FIG. 6A illustrates another variation of a cardiac device 254. The cardiac device includes a hub 256, a frame 258, and a membrane 260. The hub 256 lies at a central portion of the frame 258 and an active anchor 262 is connected to the hub 256 and extends downwards therefrom. The frame 258 includes a plurality of segments 264 which extend radially and upwardly from the hub 256. A sharp passive anchor 266 lies at the end of each of the segments 264. The membrane 260 is stretched between the segments 264 to form a cone-shaped body.

Figure 6B:
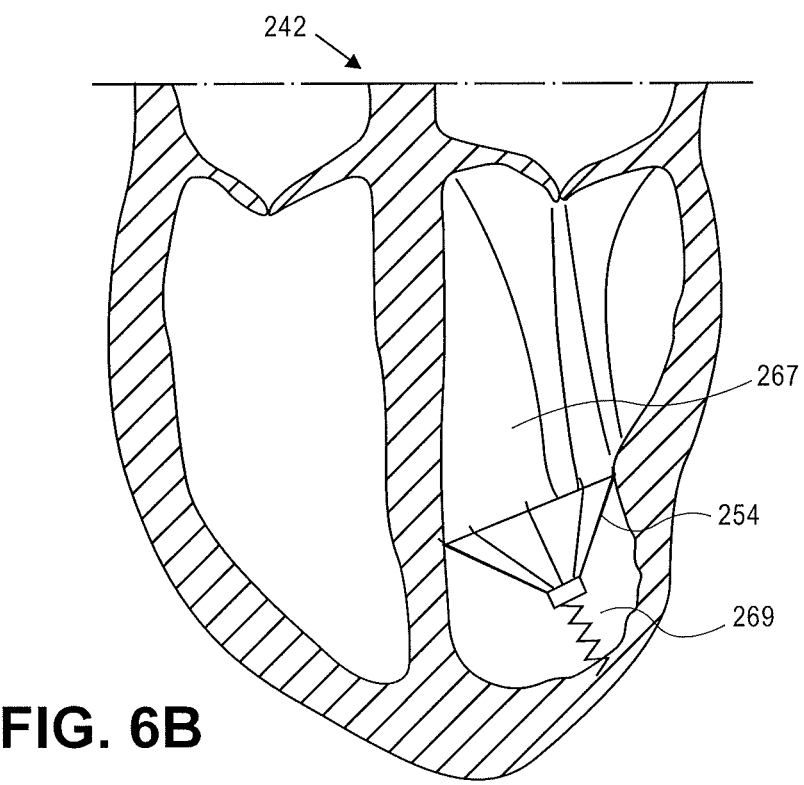
FIG. 6B is a cross-sectional side view of the human heart with the cardiac device of FIG. 6A installed.

FIG. 6B illustrates a sectional view of a human heart with the cardiac device 254 of FIG. 6A having been secured to an akinetic portion thereof.

Figure 7A:
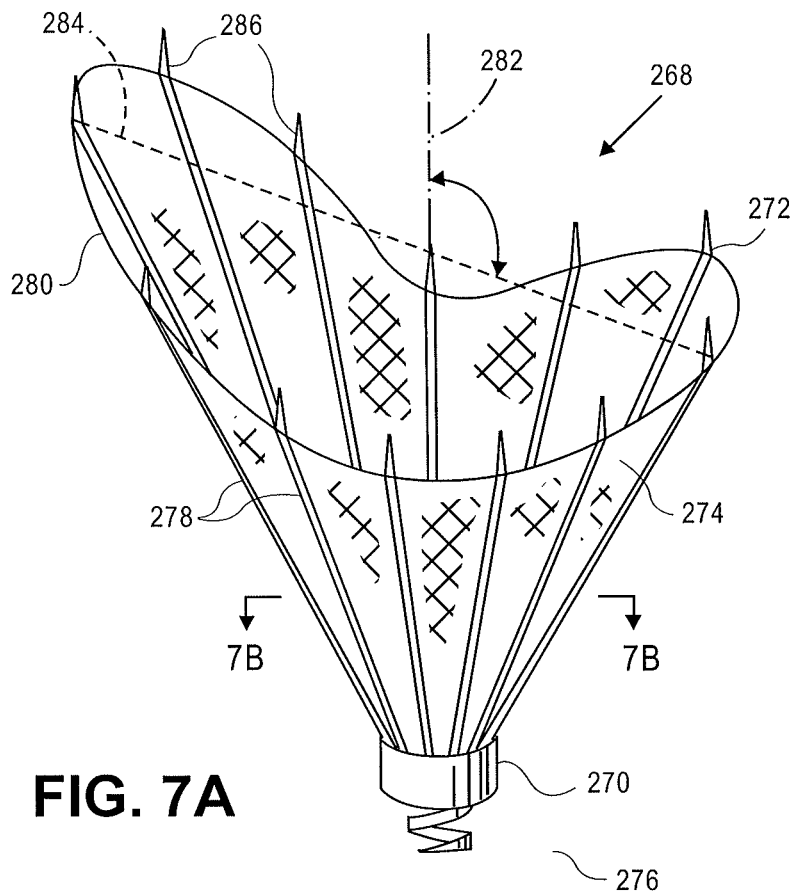
FIG. 7A is a perspective view of another variation of a cardiac device.
Figure 7B:
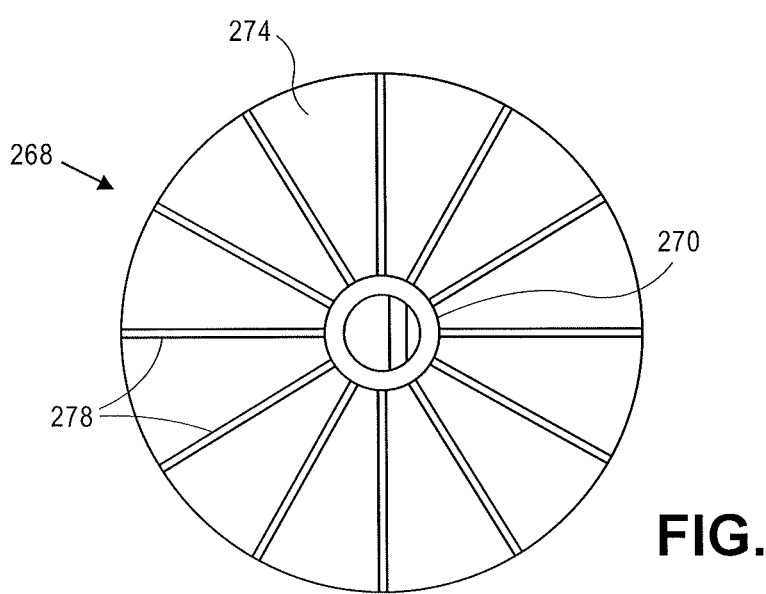
FIG. 7B is a cross-sectional top plan view of the cardiac device on 7B-7B' in FIG. 7A.

FIG. 7A and FIG. 7B illustrate another variation of a cardiac device 268. The cardiac device includes a hub 270, a frame 272, and membrane 274. The hub 270 lies at a central portion of the frame 272 and an active anchor 276 extends downwardly from the hub 270. The frame 272 includes a plurality of segments 278 which extend radially and upwardly from the hub 270. The segments 278 are of different lengths such that an outer edge 280 of the cardiac device 268 is not planar. The device 268 has a vertical axis 282 which intersects a diameter 284 across the outer edge 280 of the device 268 at an angle other than 90 degrees. A sharp passive anchor 286 lies at the end of each of the segments 278. The membrane 274 is stretched between the segments 278 to form a cone-shaped body. Referring specifically to FIG. 7B, a cross-section perpendicular to the vertical axis 282 of the device 268 is circular.

Figure 7C:
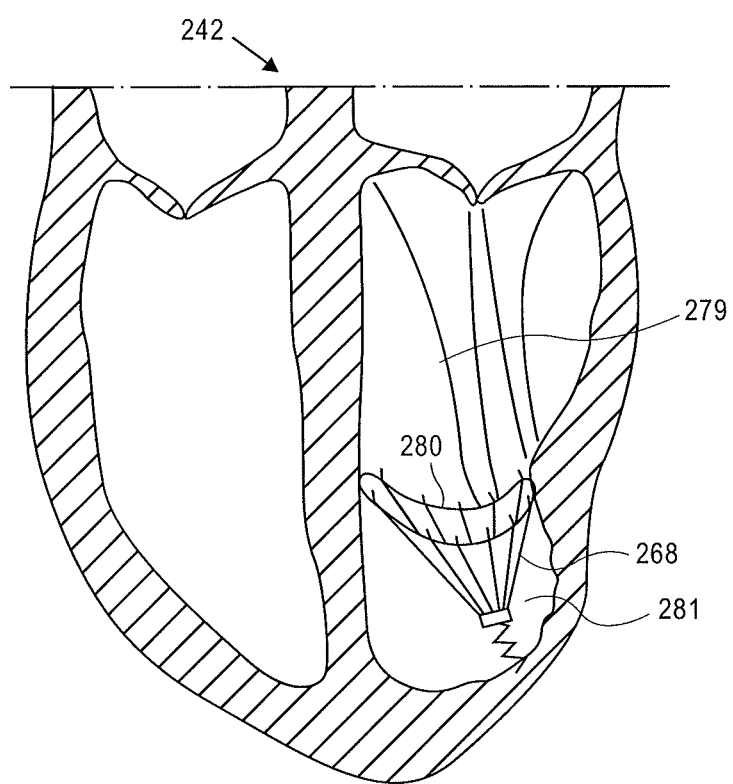
FIG. 7C is a cross-sectional side view of the human heart with the cardiac device of FIG. 7A installed.

FIG. 7C illustrates a sectional view of a human heart with the cardiac device 268 of FIG. 7A having been secured to an akinetic portion thereof. The outer edge 280 of the cardiac device 268 defines a non-planar cross-section of an inner surface of the left ventricle. The implant 268 can be sized and shaped for use on a wider variety of heart regions, including a variety of sizes and shapes of akinetic portions in left ventricles.

In some variations, the implants may include one or more collapsing elements that are configured to help collapse the implant from the expanded (deployed) configuration into the collapsed (or partially collapsed) position. For example, a sleeve or cover may be used to collapse the frame of the implant. In other variations, the implant may include a strand, wire, thread, cable, chain, etc. (which may generally be referred to as a "strand") for collapsing the device. For example, a strand may be included around the perimeter of the ribs or struts (e.g., spaced from the central hub region by any desired spacing). The strand may be a loop (e.g., joined at the ends) or it may have one or both ends free. Pulling on the strand may contract the struts, drawing them together towards the collapsed configuration.

Figure 8:
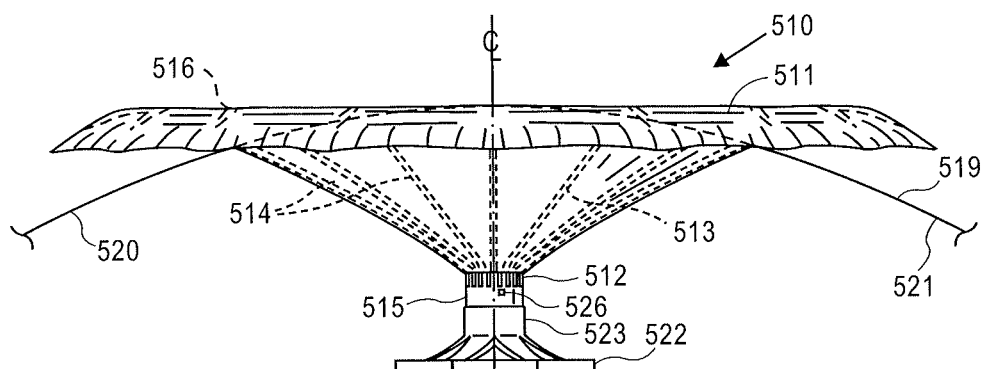
FIG. 8 is an elevational view of another variation of a partitioning device in an expanded configuration.

FIGS. 8-11 illustrate one variation of a cardiac implant device including a strand which may be used to collapse the device. In this variation, the implant (partitioning device) 10 includes a partitioning membrane 511, a hub 512, preferably centrally located on the partitioning device, and a radially expandable reinforcing frame 513 that is secured to the proximal or pressure side of the frame 513 as shown in FIG. 8. The struts 514 have distal ends 515 which are secured to the hub 512 and free proximal ends 516 which are configured to curve or flare away from a center line axis. Radial expansion of the free proximal ends 516 unfurls the membrane 511 secured to the frame 513 so that the membrane presents a pressure receiving surface 517 which defines in part the productive portion of the patient's partitioned heart chamber. The peripheral edge 518 of the membrane 511 may be serrated as shown.

The variation shown in FIGS. 8-11 also includes a continuous expansive strand 519 that extends around the periphery of the membrane 511 on the pressure side thereof. In operation, this strand may also help apply pressure to the pressure side of the flexible material of the membrane to effectively seal the periphery of the membrane against the wall of the ventricular chamber. The ends 520 and 521 of the expansive strand 519 are shown extending away from the partitioning device in FIGS. 8 and 9. As mentioned, the ends 520 and 521 may be left unattached or may be secured together, e.g. by a suitable adhesive, knot, or the like, or secured to the membrane 511 itself. While not shown in detail, the membrane 511 in this example has a proximal layer secured to the proximal faces of the struts 514 and a distal layer secured to the distal faces of the struts in a manner described in U.S. patent application Ser. No. 10/913, 608, filed on Aug. 5, 2004, herein incorporated by reference in its entirety.

Figure 10:
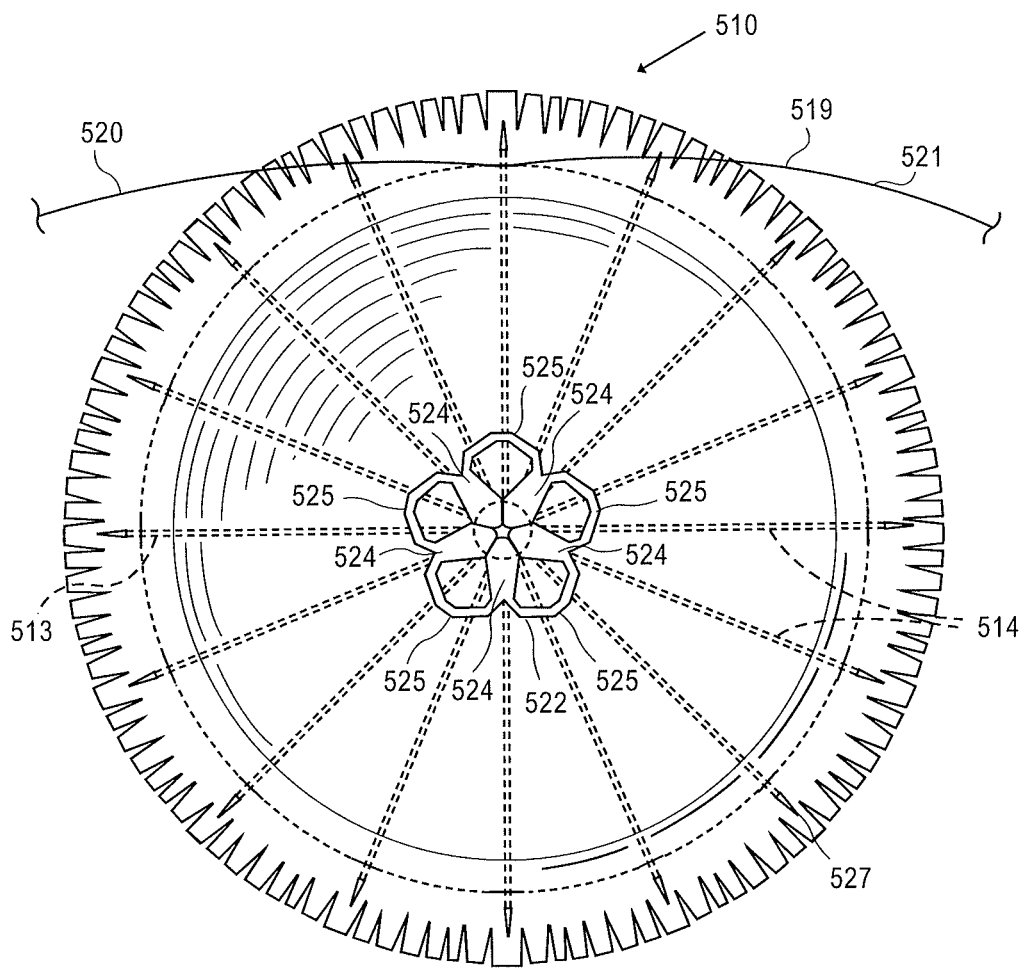
FIG. 10 is bottom view of the partitioning device shown in FIG. 8.
Figure 11:
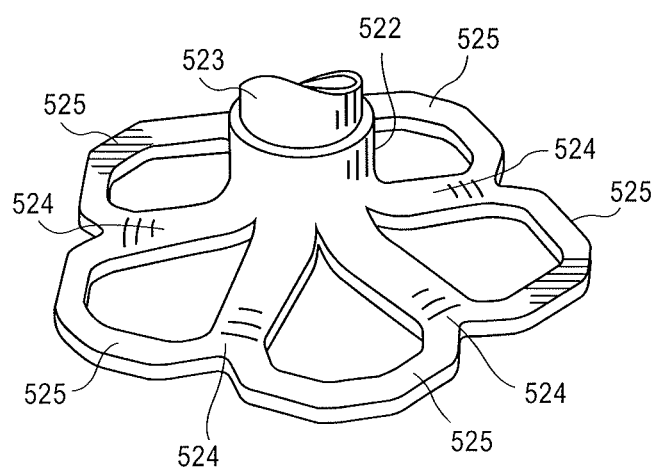
FIG. 11 is a perspective view of the non-traumatic tip of the distally extending stem of the device shown in FIG. 8.

The hub 512 shown in FIGS. 10 and 11 may be connected to a non-traumatic support component 522. The support component 522 shown in FIGS. 10 and 11 has a stem 523 a plurality of pods or feet 524 extending radially away from the center line axis and the ends of the feet 524 are secured to struts 525 which extend between adjacent feet. A plane of material (not shown) may extend between adjacent feet 524 in a web-like fashion to provide further support in addition to or in lieu of the struts 525. The inner diameter of the stem 523 is threaded to secure the partitioning device 510 to a delivery catheter as shown in FIGS. 15-17.

Figure 12:
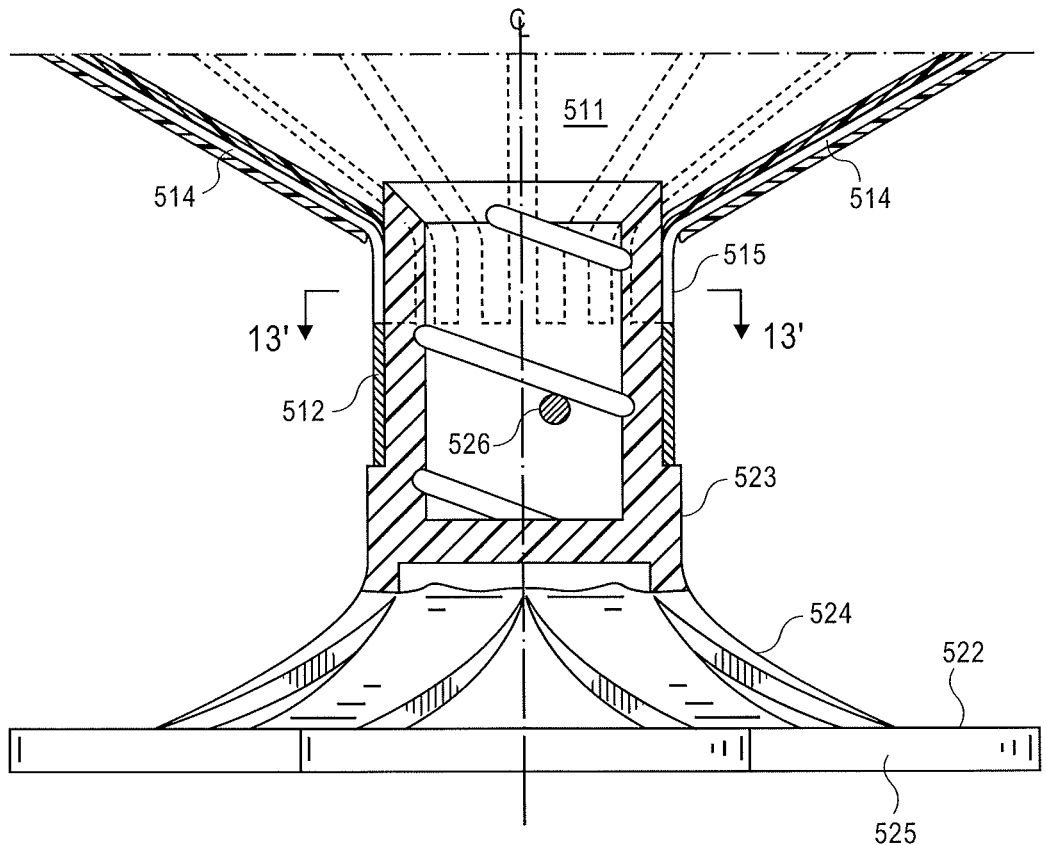
FIG. 12 is a partial cross-sectional view of the hub of the partitioning device shown in FIG. 9 taken along the lines 12-12'.
Figure 13:
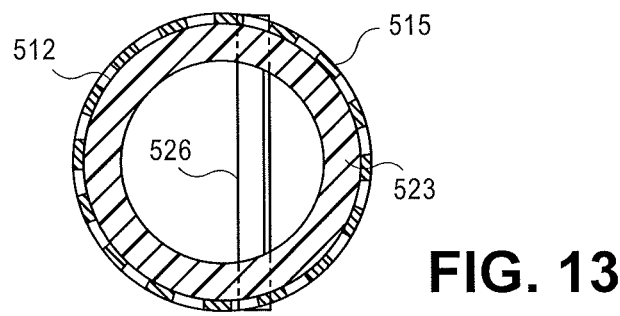
FIG. 13 is a transverse cross sectional view of the hub shown in FIG. 12 taken along the lines 13-13'.

As shown in FIG. 12, the distal ends 515 of the struts 514 are secured within the hub 512 and, as shown in FIG. 13, a transversely disposed connector bar 526 is secured within the hub which is configured to secure the hub 512 to the nontraumatic support component 522.

Figure 9:
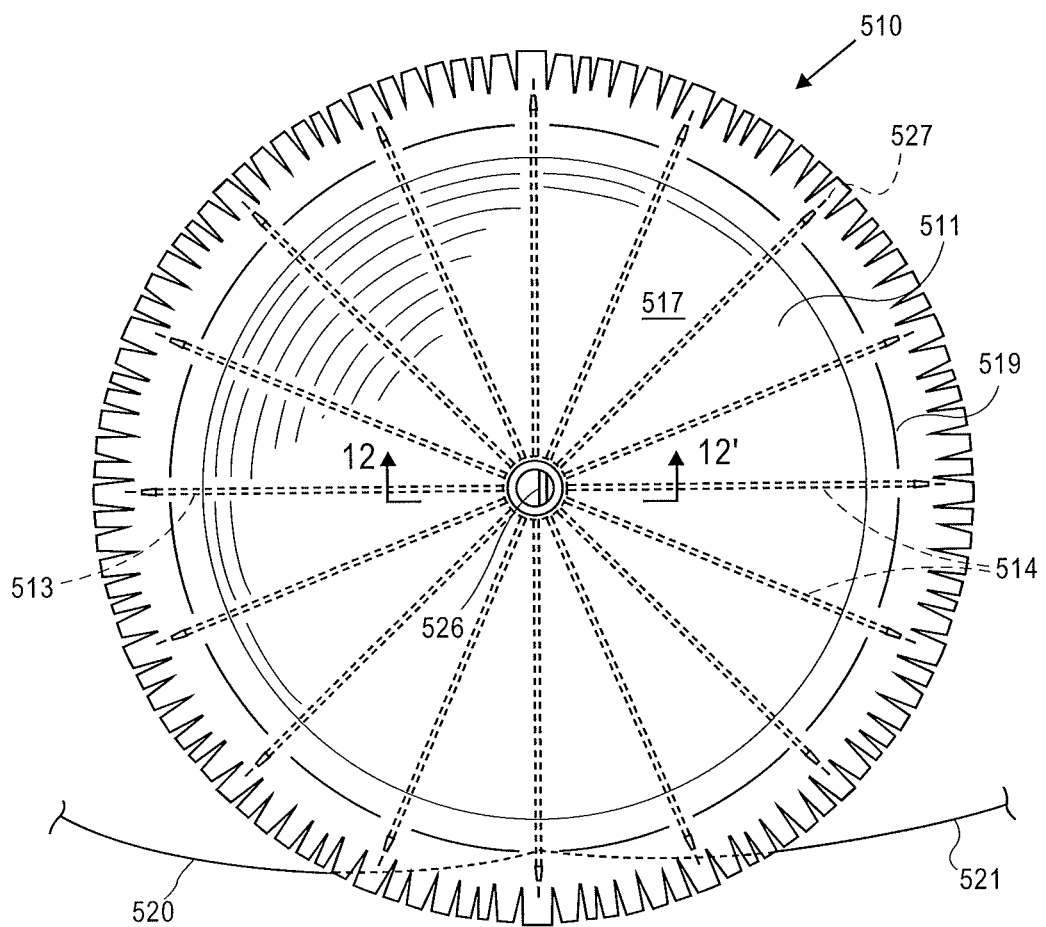
FIG. 9 is a plan view of the partitioning device shown in FIG. 8 illustrating the upper surface of the device.

In FIGS. 12 and 13, the screw thread inside stem 523 allows the partitioning device 510 to be secured to the non-traumatic support component 522 and to be released from the delivery system within the patient's heart chamber. The distal ends 515 of the reinforcing struts 514 are secured within the hub 512 in a suitable manner or they may be secured to the surface defining the inner lumen or they may be disposed within channels or bores in the wall of the hub 512. The distal end of the struts 514 are preshaped so that when the struts are not constrained, other than by the membrane 511 secured thereto (as shown in FIGS. 8 and 9), the free proximal ends 516 thereof expand to a desired angular displacement away from the centerline axis which is about 20 degrees to about 90 degrees, preferably about 30 degrees to about 60 degrees. The unconstrained diameter of the partitioning device 510 should be greater than the diameter of the heart chamber at the deployed location of the partitioning device so that an outward force is applied to the wall of the heart chamber by the partially expanded struts 514 during systole and diastole so that the resilient frame 513 augments the heart wall movement.

Figure 14:
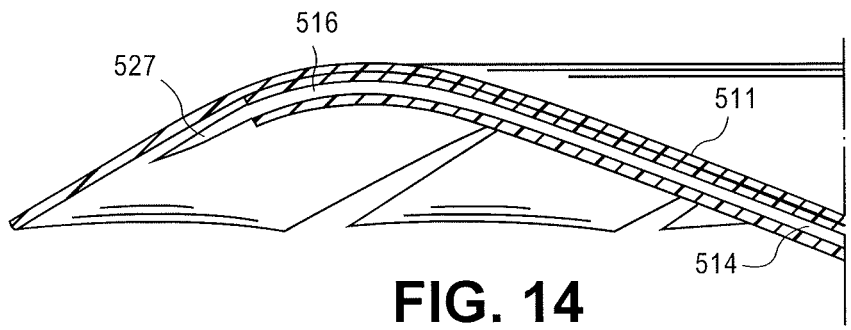
FIG. 14 is a longitudinal view, partially in section of a reinforcing strut and membrane at the periphery of the partitioning device shown in FIG. 8.

FIG. 14 illustrates the curved free proximal ends 516 of struts 514 which are provided with sharp tip elements 527 configured to engage and preferably penetrate into the wall of the heart chamber and hold the partitioning device 510 in a deployed position within the patient's heart chamber so as to partition the ventricular chamber into a productive portion and a non-productive portion.

FIGS. 15-17 illustrate one variation of an applicator (delivery system) 530 that may be used for delivering the partitioning device 510 shown in FIGS. 8 and 9 into a patient's heart chamber and deploying the partitioning device to partition the heart chamber as shown in FIGS. 18A-18E. The applicator system 530 includes a guide catheter 531 and a delivery catheter 532.

The guide catheter 531 has an inner lumen 533 extending between the proximal end 534 and distal end 535. A hemostatic valve (not shown) may be provided at the proximal end 534 of the guide catheter 531 to seal about the outer shaft 537 of the delivery catheter 532. A flush port 536 on the proximal end 534 of guide catheter 531 is in fluid communication with the inner lumen 533.

The delivery catheter 532 in this variation includes an outer shaft 537 with an adapter 538 on the proximal end thereof having a proximal injection port 539 which is in fluid communication with the interior of the outer shaft 537. As shown in more detail in FIG. 16, the outer shaft 537 has an inner shaft 541 which is disposed within the interior thereof and is secured to the inner surface of the outer shaft 537 by webs 543 which extend along a substantial length of the inner shaft. The injection port 539 is in fluid communication with the passageways 542 between the inner and outer shafts 541 and 537 respectively and defined in part by the webs 542. A torque shaft 544, which is preferably formed of hypotubing (e.g. formed of stainless steel or superelastic NiTi), is disposed within the inner lumen 545 of the inner shaft 541 and has a proximal end 546 secured within the adapter 538. Balloon inflation port 547 is in fluid communication with the inner lumen 548 of the torque shaft 544. Torque shaft 544 is rotatably disposed within the inner lumen 545 of the inner shaft 541 and is secured to rotating knob 549. A helical coil screw 550 is secured to the distal end 551 of the torque shaft 544 and rotation of the torque knob 549 on the proximal end 546 of the torque shaft 544 rotates the screw 550 to facilitate deployment of a partitioning device 510. The proximal end 552 of inflatable balloon 553 is sealingly secured by adhesive 554) about the torque shaft 544 proximal to the distal end 551 of the torque shaft. The balloon 553 has an interior 555 in fluid communication with the inner lumen 548 of the torque shaft 544. Inflation fluid may be delivered to the balloon interior 555 through port 547 which is in fluid communication with the inner lumen 548 of the torque shaft 544. The distal end 556 of the balloon 553 is sealingly secured by adhesive 557 to the helical screw 550. The proximal and distal ends 552 and 556 of the balloon 553 are blocked by the adhesive masses 554 and 557 to prevent the loss of inflation fluid delivered to the interior 555 of the balloon 553. Delivery of inflation fluid through a fluid discharge port 558 in the distal end 551 of the torque shaft 544 inflates the balloon 553 which in turn applies pressure to the proximal surface of the partitioning component 510 (or device) to facilitate securing the partitioning component 510 to the wall 559 of heart chamber 560 as shown in FIGS. 18A-18E discussed below.

Figure 18A:
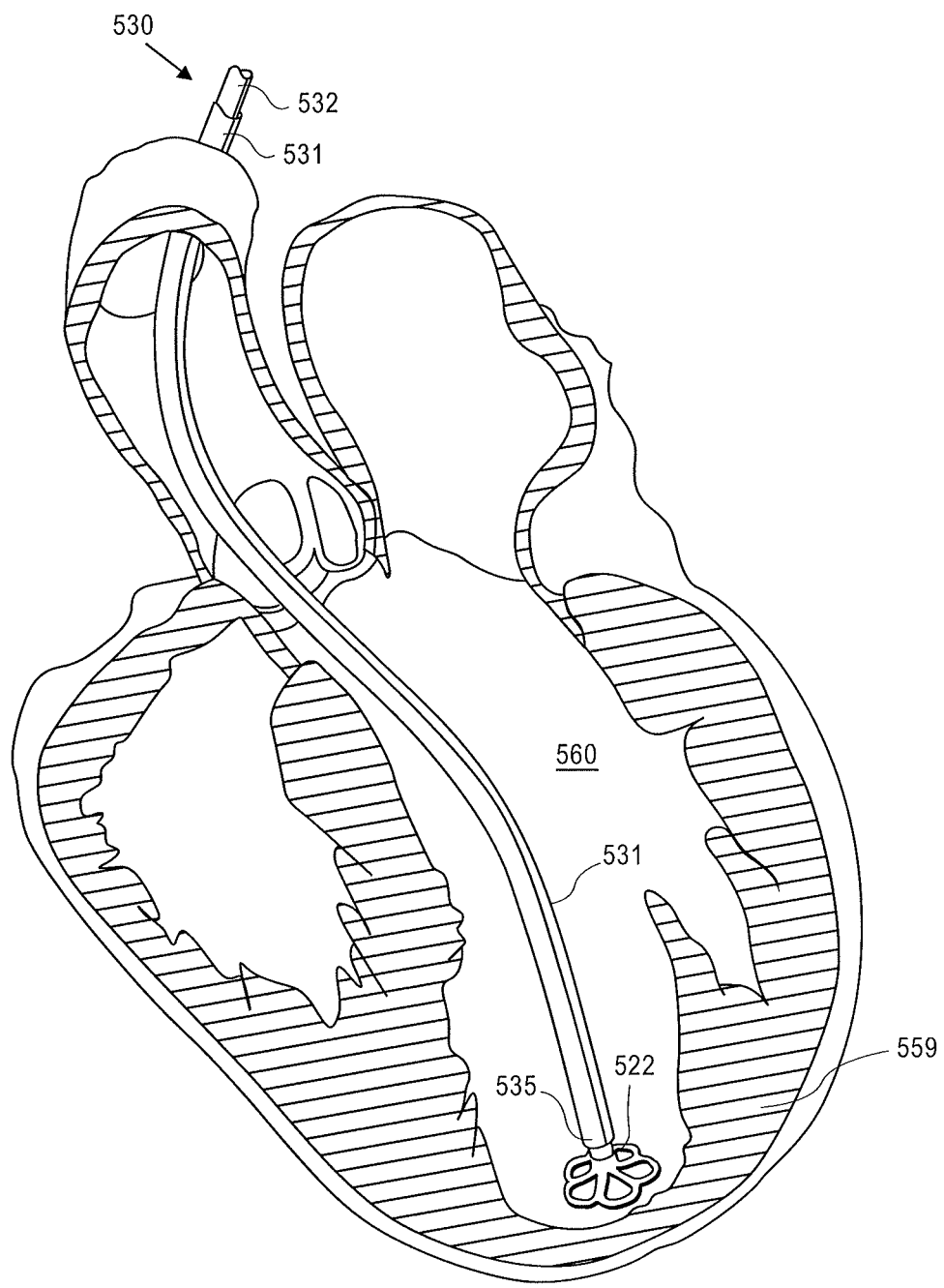
FIGS. 18A-18E are schematic views of a patient's left ventricular chamber illustrating the deployment of the partitioning device shown in FIGS. 8 and 9 with the applicator shown in FIG. 15 to partition a patient's heart chamber (left ventricle) into a primary productive portion and a secondary, non-productive portion.

As shown in FIG. 18A, the partitioning component 510 is delivered through a delivery system 530 which includes a guide catheter 531 and a delivery catheter 532. The partitioning component 510 is collapsed in a first, delivery configuration which has small enough transverse dimensions to be slidably advanced through the inner lumen 533 of the guide catheter 531. Preferably, the guide catheter 531 has been previously percutaneously introduced and advanced through the patient's vasculature, such as the femoral artery, in a conventional manner to the desired heart chamber 560. The delivery catheter 532 with the partitioning component 510 attached is advanced through the inner lumen 533 of the guide catheter 531 until the partitioning component 510 is ready for deployment from the distal end of the guide catheter 531 into the patient's heart chamber 560 to be partitioned.

Figure 18B:
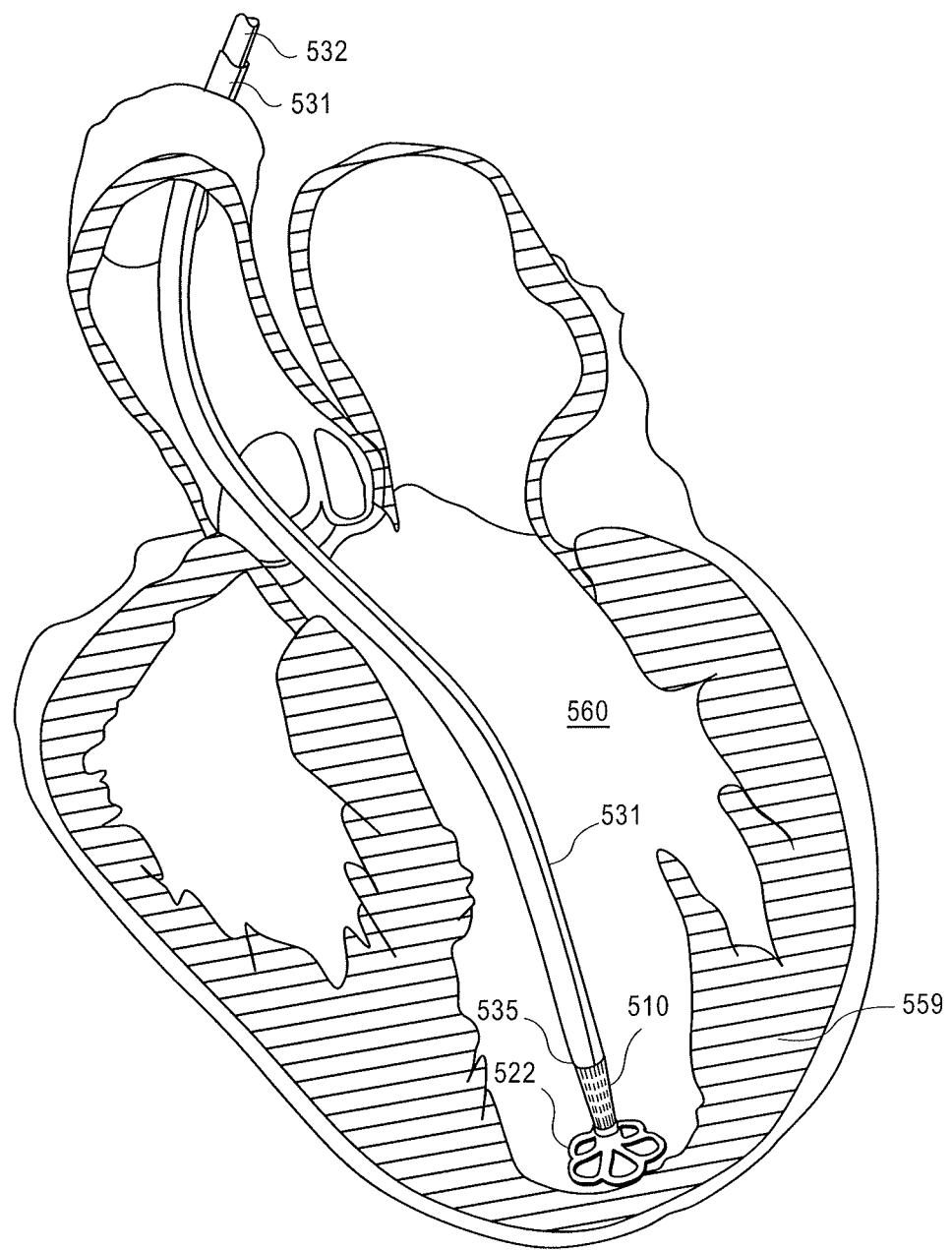
Figure 18C:
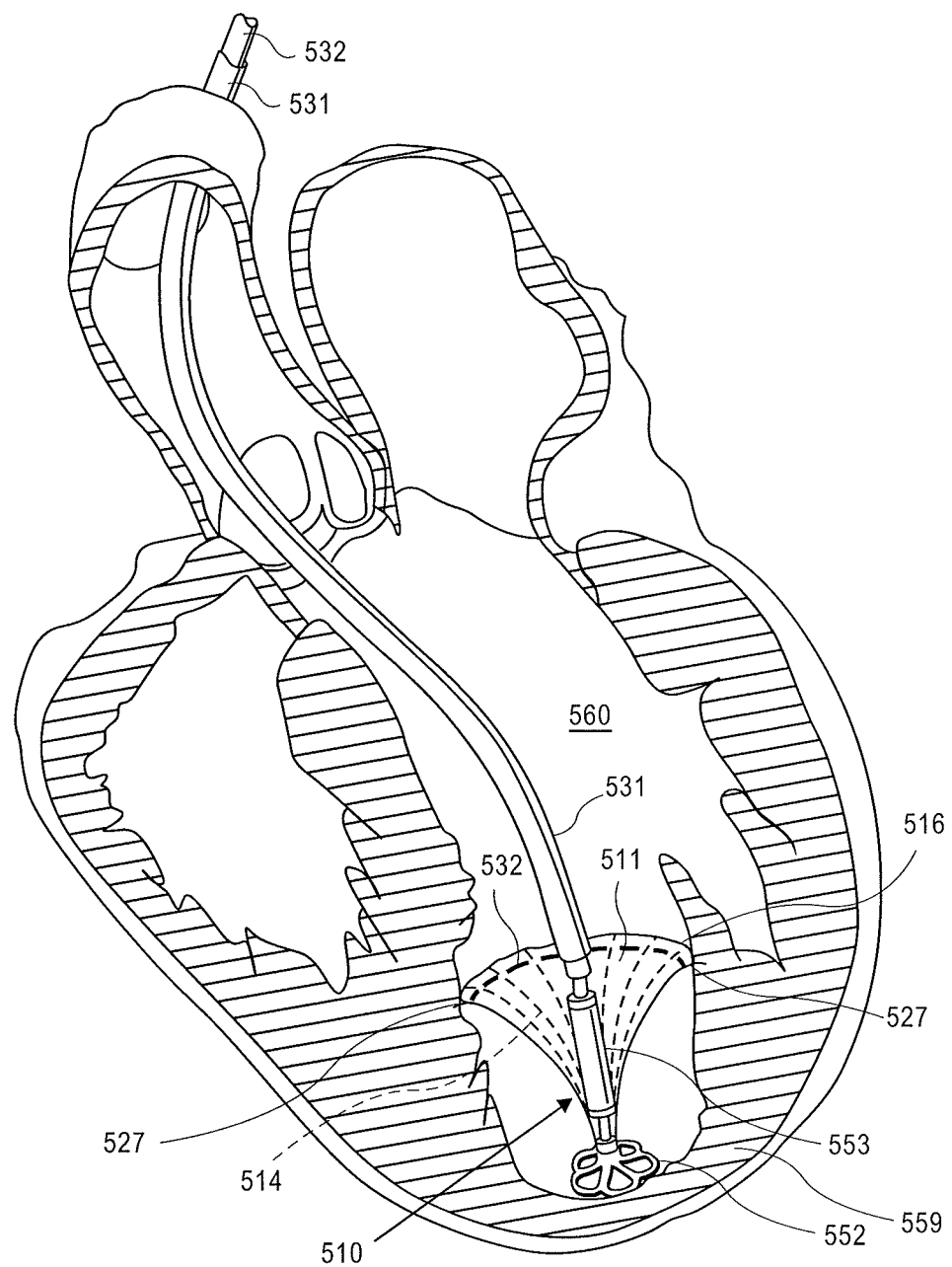

As shown in FIG. 18B-18C, the partitioning component 510 mounted on the screw 550 is urged further out of the inner lumen 533 of the guide catheter 532 until the support component 522 engages the heart wall 559. The guide catheter 531 is withdrawn while the delivery catheter 532 is held in place until the proximal ends 516 of the struts 514 exit the distal end 35 of the guide catheter. As shown in FIG. 18C, the free proximal ends 516 of struts 514 expand outwardly to press the sharp proximal tips 527 of the struts 514 against and preferably into the tissue lining the heart wall 559.

Figure 18D:
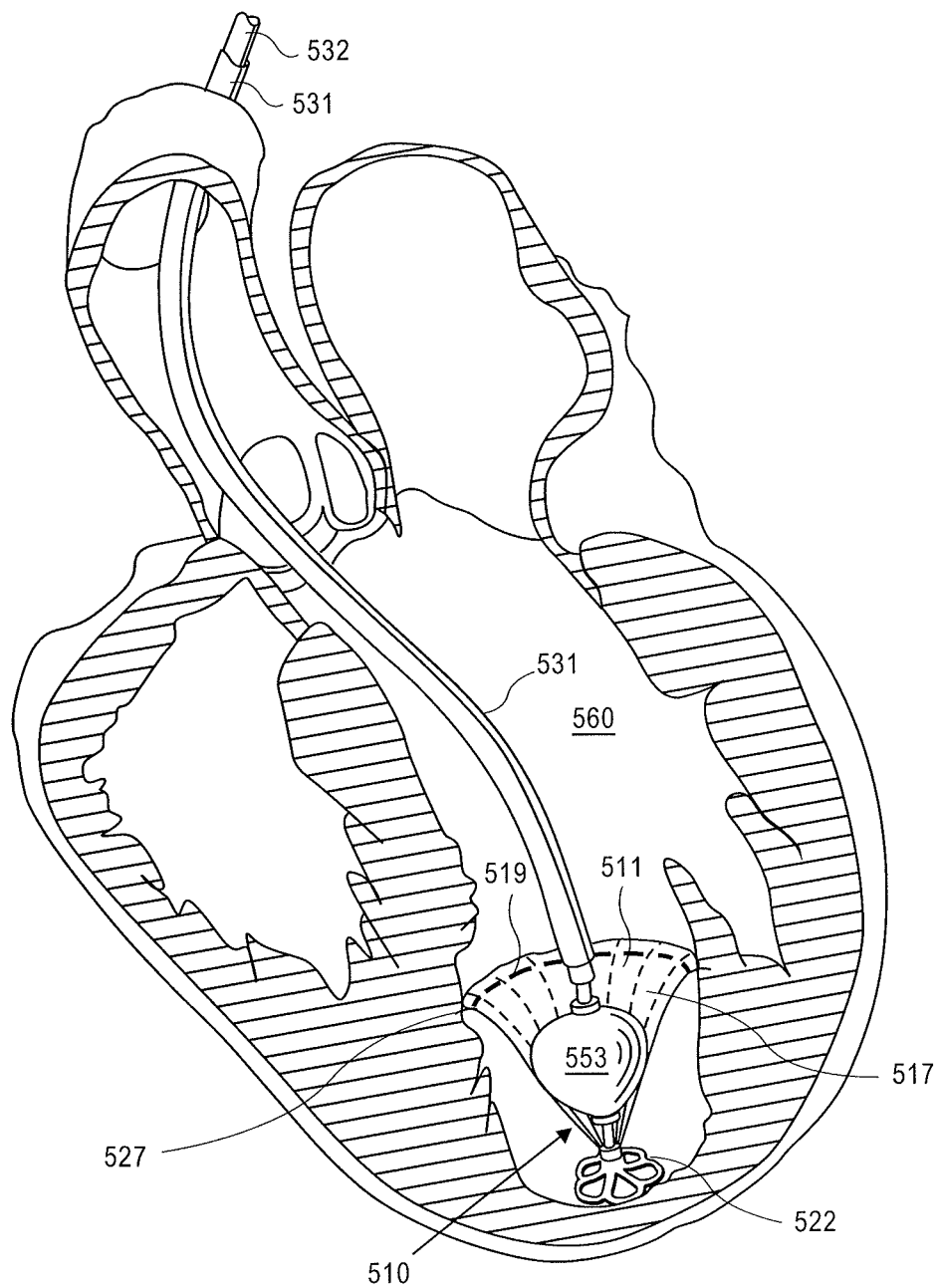

With the partitioning component 510 deployed within the heart chamber 560 and preferably partially secured therein, inflation fluid is introduced through the inflation port 558 in the distal end 551 torque shaft 544 where it is directed into the balloon interior 555 to inflate the balloon 553. The inflated balloon 553 presses against the pressure receiving surface 517 of the membrane 511 of the partitioning component 510 to ensure that the sharp proximal tips 527 are pressed well into the tissue lining the heart wall 559 as shown in FIG. 18D.

With the partitioning device 510 properly positioned within the heart chamber 560, the knob 549 on the torque shaft 544 (as shown in FIG. 15) is rotated counter-clockwise to disengage the helical coil screw 550 of the delivery catheter 532 from the stem 523 secured within hub 512. The counter-clockwise rotation of the torque shaft 544 rotates the helical coil screw 550 which rides on the screw thread inside the stem 523 secured within the hub 512. Once the helical coil screw 550 disengages the screw thread inside the stem 523, the delivery system 530, including the guide catheter 531 and the delivery catheter 532, may then be removed from the patient.

The proximal end 534 of the guide catheter 531 is provided with a flush port 536 to inject fluids such as therapeutic, diagnostic or other fluids through the inner lumen 533 during the procedure. Similarly, the proximal injection port 539 of adapter 538 is in communication with passageways 542 if the delivery catheter 532 for essentially the same purpose.

Figure 18E:
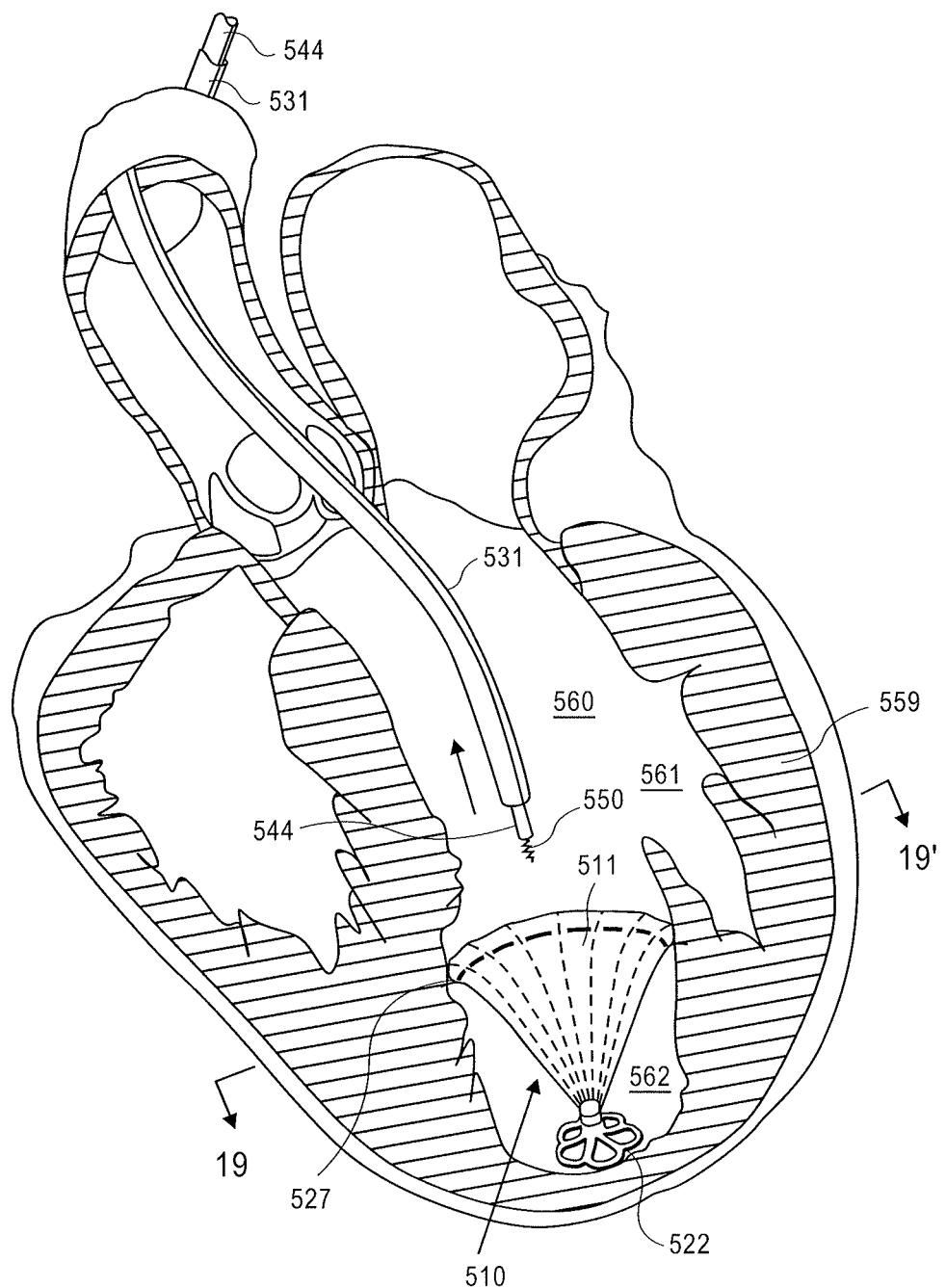

The deployment of the partitioning component 510 in the patient's heart chamber 560 as shown in FIG. 18E divides the chamber into a main productive or operational portion 561 and a secondary, essentially non-productive portion 562. The operational portion 561 is smaller than the original heart chamber 560 and provides for an improved ejection fraction and an improvement in blood flow. Over time, the non-productive portion 562 fills first with thrombus and subsequently with cellular growth. Bio-resorbable fillers such as polylactic acid, polyglycolic acid, polycaprolactone and copolymers and blends may be employed to initially fill the non-productive portion 562. Fillers may be suitably supplied in a suitable solvent such as dimethylsulfoxide (DMSO). Other materials which accelerate tissue growth or thrombus may be deployed in the non-productive portion 562 as well as non-reactive fillers.

Figure 19:
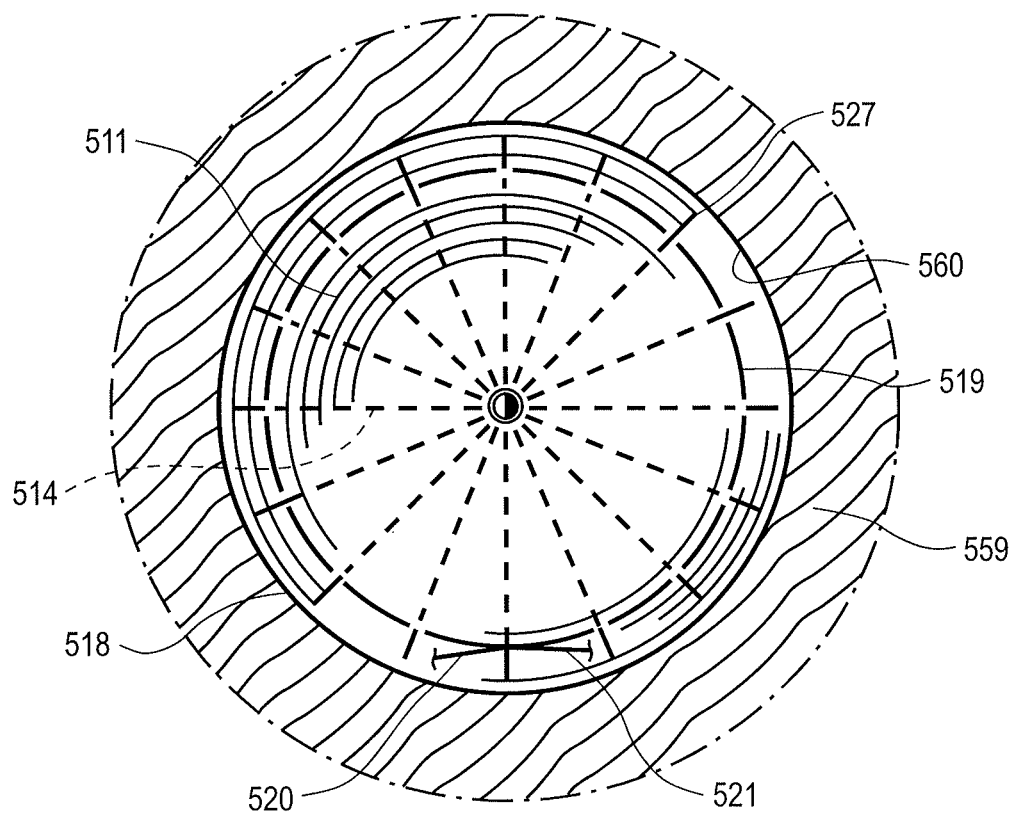
FIG. 19 is a schematic plan view of the deployed device shown in FIG. 18E within a patient's heart chamber.

FIG. 19 is a top view of the deployed partitioning device shown in FIG. 18E schematically illustrating the sealed periphery of the membrane 511 against the ventricular wall.

Once the device is deployed, as shown in FIGS. 18E and 19, the device may be removed and/or repositioned. For example, in the implant variation shown in FIGS. 8 and 9, pulling the strand 519 may disengage the anchors or tip element 527 at the ends of the struts 514 from the heart wall. For example, the applicator 530 may be re-engaged with the implant (e.g., the hub region). An element on the applicator may engage the strand so that it can be pulled to collapse the implant. In some variations, one or more ends of the strand remain connected to the applicator during the insertion procedure, so that even when initially disengaged from the applicator, the strand is connected to the applicator until the position is confirmed.

Examples of applicators including members for grasping and/or manipulating a strand are described in greater detail below.

FIGS. 20A-20C illustrate the collapse and retrieval of an implant (partitioning device 510) by pulling on the ends 520 and 521 of an expansive strand 519 which extends around the periphery of the membrane 511. Typically, the partitioning device 510 may be secured to the delivery catheter 532, but the delivery catheter is not shown in this example to simplify the drawings. In FIG. 20A the partitioning device 510 is shown in a partially collapsed configuration. In FIG. 20B the partially collapsed partitioning device 510 is shown being withdrawn into the flared distal end 563 of retrieval catheter 564. FIG. 20C illustrates the completely collapsed partitioning device 510 pulled further into the retrieval catheter 564. The partitioning device 510 may be withdrawn by pulling the device through the inner lumen 565 of the retrieval catheter 564. Optionally, the partitioning device 510 and applicator (e.g., retrieval catheter) may be withdrawn from the patient together.

In this variation the applicator includes a flanged distal end on the catheter, so that the implant may more readily be inserted into the distal end of the applicator. This flanged distal end is optional, and is not necessarily present.

In general, the implantation, removal and/or repositioning of the implants described herein may be performed under direct or indirect visualization. For example, any of the procedures or methods described herein may be performed under fluoroscopy. To assist in properly locating the device during advancement and placement thereof into a patient's heart chamber, parts, e.g. the distal extremity, of one or more of the struts 14 and/or the hub 12 may be provided with markers at desirable locations that provide enhanced visualization by eye, by ultrasound, by X-ray, or other imaging or visualization means. Radiopaque markers may be made with, for example, stainless steel, platinum, gold, iridium, tantalum, tungsten, silver, rhodium, nickel, bismuth, other radiopaque metals, alloys and oxides of these metals.

Figure 21:
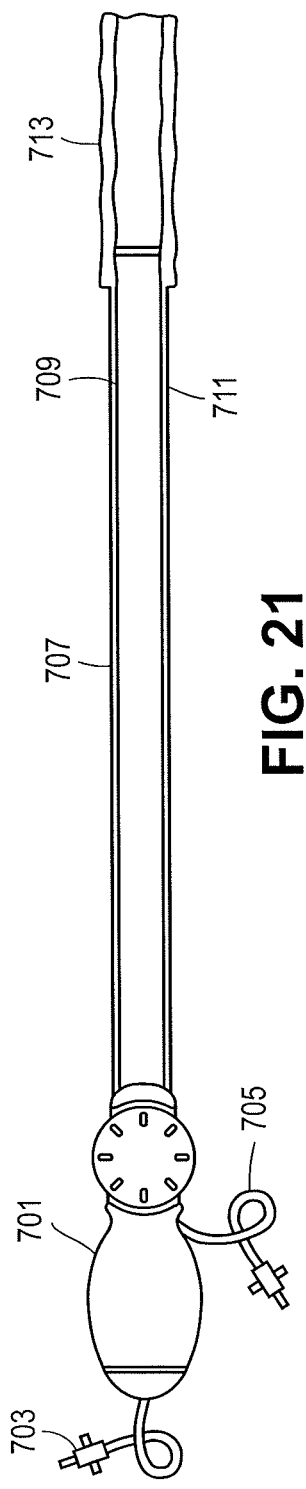
FIG. 21 is a schematic view of another variation of an inserter configured to apply and remove and/or reposition an implant.

FIG. 21 shows another variation of an applicator configured to apply and retrieve and/or reposition a cardiac implant. In some variations, an applicator such as the one illustrated in FIG. 21 is included as part of a system including an implant. In FIG. 21, the applicator includes a control handle 701 having a plurality of controls for controlling engaging and disengaging from an implant, as well as a flush port 703 and a balloon inflating port 705. In this variation, the applicator also includes an elongate shaft 707 comprising an inner shaft 709 and an outer shaft 711. The distal end of the applicator includes an everting balloon or inflatable sleeve 713 that is inflatable by applying fluid (e.g., air, liquid, etc.) through the inflation port 705. Inflating the everting balloon may cause it to extend, as illustrated in FIGS. 22A-22F. In addition to the features illustrated in FIG. 21, other elements such as an implant stabilizing shaft and or a strand-grasping hook (not visible in FIG. 21) may also be included within the inner shaft, and controlled proximally, e.g., using the handle. For example, the applicator may include a deployment member, as described above. The implant stabilizing shaft may be configured as a deployment member.

Figures 22A, 22B, 22C:
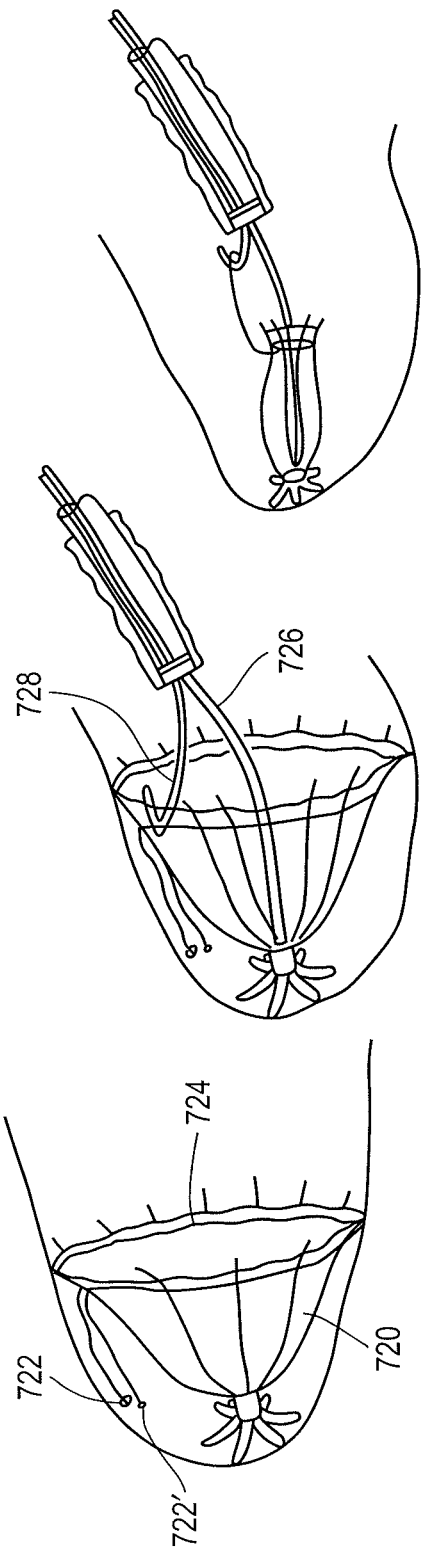
FIG. 22A-22F illustrate retrieval of a cardiac implant as (partitioning device) using the applicator of FIG. 21.
Figure 22F:
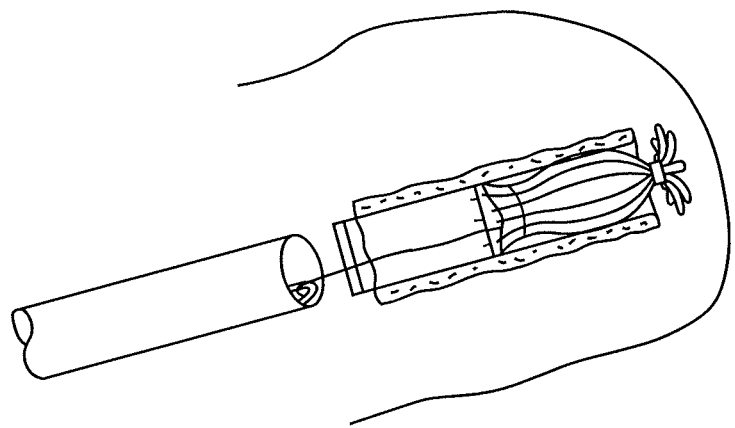
Figure 22E:
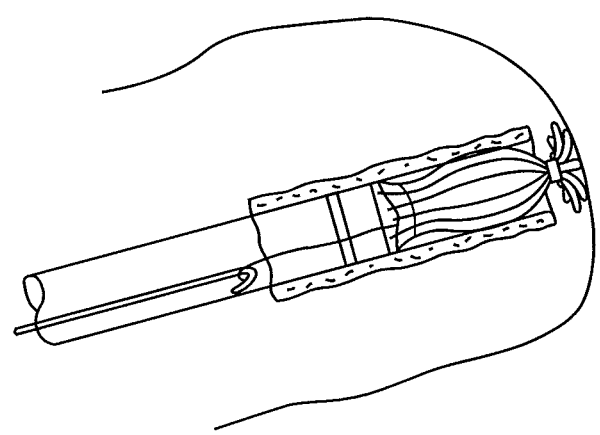
Figure 22D:
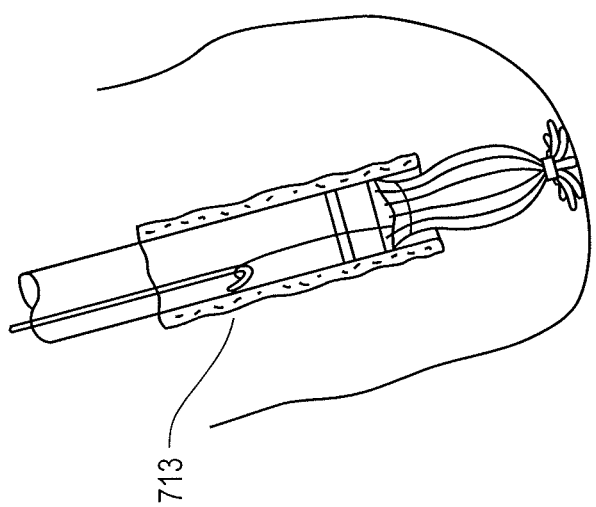

FIGS. 22A-22F illustrate operation of an applicator such as that shown in FIG. 21 to remove an implant (partitioning implant 720). FIG. 22A illustrates a cardiac implant 720 that has been deployed into a patient's heart, as shown. The implant 720 includes a strand, suture 724 that extends around the perimeter of the implant and has two ends 722, 722' which are knotted or otherwise prevented from pulling past the membrane surrounding the device. The strand 724 is threaded around the inner diameter of the implant.

In FIG. 22B, the applicator shown in FIG. 21 has been inserted into the heart so that the distal end of the applicator is positioned across from the deployed implant. The elongate catheter, including the inflatable distal portion 713 is positioned across from the implant so that an implant stabilizing shaft 726 may be extended from the distal end of the applicator to engage the implant. As previously described, the implant stabilizing shaft 726 (e.g., a deployment member) may engage with the implant at the hub or any other appropriate region (e.g., the foot, etc.). A strand hook 728 may also be extended from the distal end of the applicator as shown in FIG. 22B, so that it can extend from the applicator and engage at least a portion of the strand. In some variations, the strand hook is a grasper, jaw, or other strand-capturing element. As shown in FIG. 22C, the strand can then be drawn proximally by withdrawing the strand hook 728 proximally into the applicator while holding the device in position. Drawing the strand proximally while keeping the device distally positioned will constrict the strand and collapse the struts of the implant. In some variations, the method of collapsing the implant may include a step of pushing the implant distally (away from the applicator) to disengage the ends of the struts from the heart wall. As described in more detail below, the implant (e.g., the foot region) may also be configured to collapse or shorten to facilitate disengaging of the struts from the heart wall.

After collapse of the implant, as shown in FIG. 22C, the applicator may be extended over the implant. In one variation, illustrated in FIGS. 22D-22E, the inflatable everting balloon or cuff 713 is inflated so that it extends and advances over the implant. In some variations, the cuff on the distal end of the applicator is not inflatable, but is otherwise extendable from the distal end to cover the device. For example, the distal end may include a toroidal region that can be "rolled" over the collapsed implant so that the implant is secured within the central lumen of the toroidal region. Once the implant has been secured within the applicator, it may be removed, along with the applicator, from the patient, or repositioned and deployed again.

FIG. 23A illustrates another variation of an applicator which may be used to apply and remove and/or reposition an implant. In FIG. 23A, the applicator includes a handle region 801 having one or more controls. In the variation shown in FIG. 23A the handle includes a control, shown as a knob 803 for extending an capture umbrella (described below), and a control for operating a suture hook (suture hook knob 805). The applicator also includes an elongate catheter region 807, and suture capture hook 822 as well as an implant capture umbrella 810.

FIG. 23B illustrates a cross-sectional view through the catheter region of the applicator shown in FIG. 23A along line A-A'. As shown in FIG. 23B, the applicator include an implant capture umbrella lumen 830 and a suture capture hook lumen 831. In some variations only a single lumen is used to house both the suture capture hook and the implant capture lumen. In some variations an implant stabilizing shaft is also included, similar to that described above in FIGS. 21 and 22A-F. For example, an implant stabilizing shaft (not shown in FIGS. 23A-24F) may be positioned concentrically within the shaft connected to the implant capture umbrella. The implant stabilizing shaft may be operated independently of the implant capture umbrella 810.

Figure 24F:
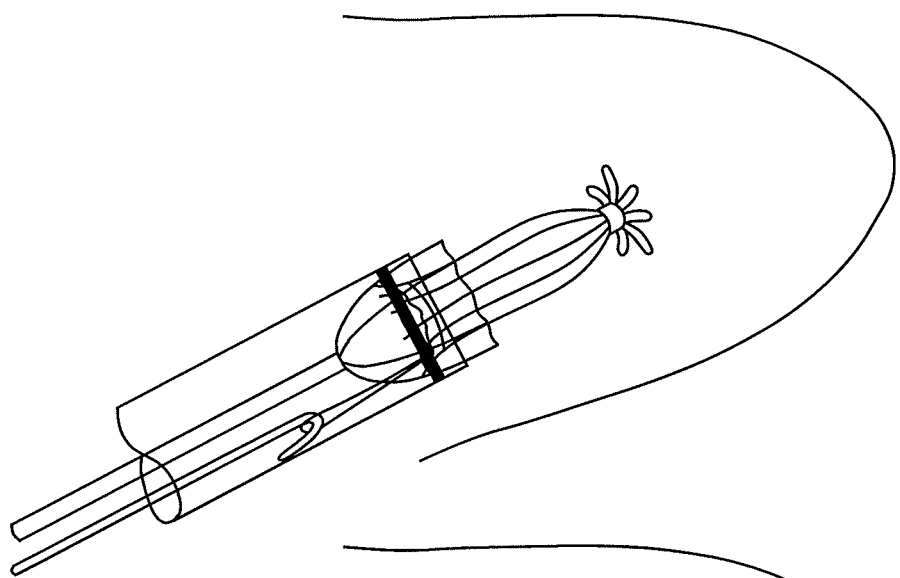
Figure 24E:
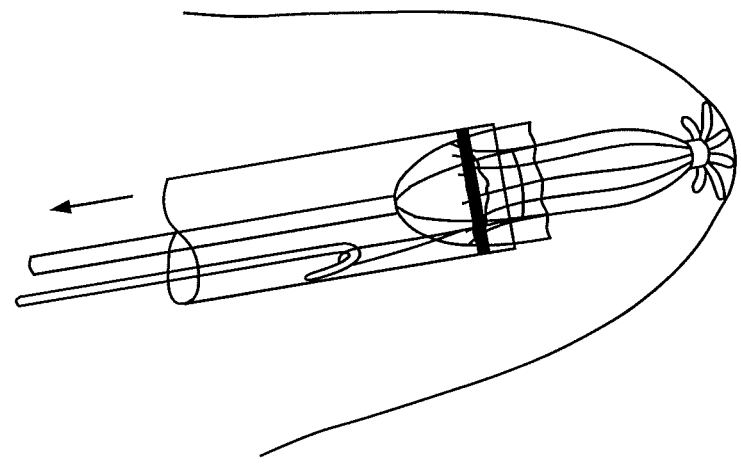
Figure 24D:
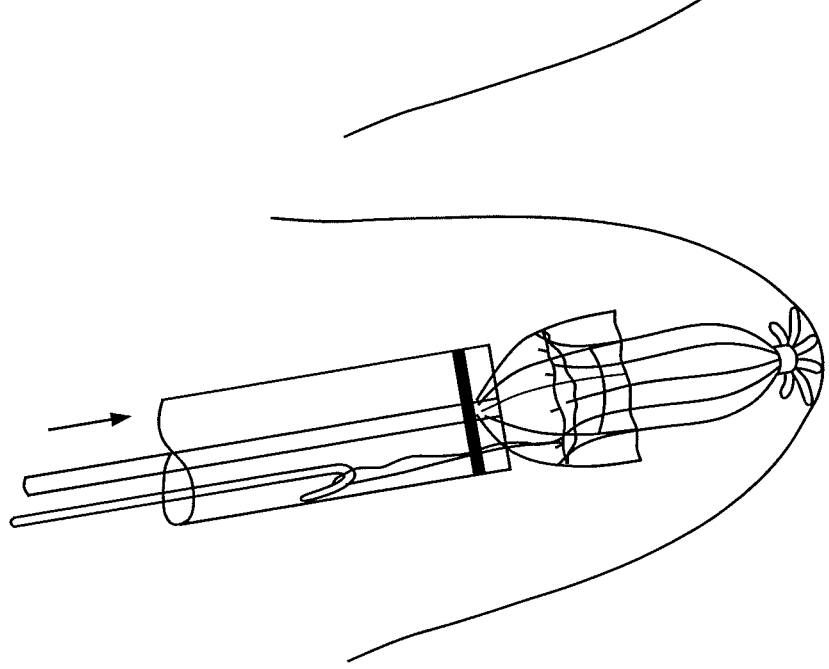

FIGS. 24A-24F illustrate operation of an applicator as shown in FIG. 23A to remove an implant that has been deployed in a patient's heart. FIG. 24A shows an implant, similar to the implant shown and described for FIG. 22A, is shown implanted into the left ventricle 850 of a patient's heart. The implant 720 also includes a suture or strand 724, having two ends that have been jointed together or knotted 722. The implant may be removed from the deployed position in the heart as illustrated in FIGS. 24B-24. The stand capture hook 822 is extended distally from the applicator to capture or otherwise engage the strand 724 on the implant. In some variations an implant stabilization shaft 726 is also extended from the distal end of the applicator so that it engages the implant, as shown for FIG. 22B, above. After capture of the strand, the stand capture hook 822 is drawn proximally back using the applicator. For example, the applicator handle may be manipulated to draw the strand proximally, e.g., by operating the strand hook knob 805. This results in collapsing the implant, as illustrated in FIG. 24C. Thereafter, the implant capture umbrella 810 of the applicator is extended distally out of the catheter of the applicator. As shown in FIG. 24D, when the implant capture umbrella is extended from the applicator, it expands as it leaves the implant catheter region. For example, the implant capture umbrella may be formed of struts of Nitinol or other materials that are biased outwards. A membrane or netting may be present between the struts. In some variations, the umbrella does not include a membrane, but comprises only struts. The struts may be coated (e.g., with a polymeric material) to prevent damage to the tissue and/or the implant.

The implant capture umbrella may be extended over the collapsed device 720, as shown in FIG. 24D. The implant 720 may then be drawn into the applicator by retracting the capture umbrella 810 (and an implant stabilization shaft, if included) into the catheter region of the applicator, as shown in FIG. 24E. In some variations, the implant is only partially withdrawn into the applicator. FIG. 24F illustrates removal of the applicator and implant from the patient.

Although many of the applicator devices described herein are configured for both insertion and removal of an implant, it should be understood that an applicator can be configured as an implant removal device alone. For example, an implant removal device may otherwise resemble the applicators described above (including FIG. 23A), but may not be configured to release the implant in the patient's heart after it has been captured and removed. In some variations an implant removal device resembles the applicator of FIG. 23A, and does not include an implant stabilization shaft that is configured to release the implant.

Figure 25A:
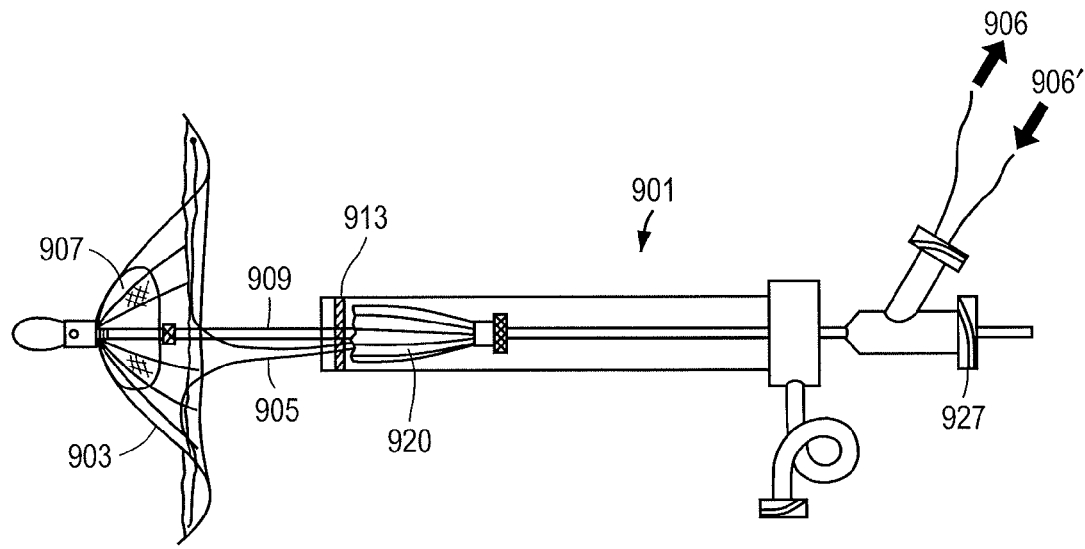
FIGS. 25A and 25B show another variation of a system including an applicator and an implant in which the implant is secured to the applicator and released from the applicator, respectively.
Figure 25B:
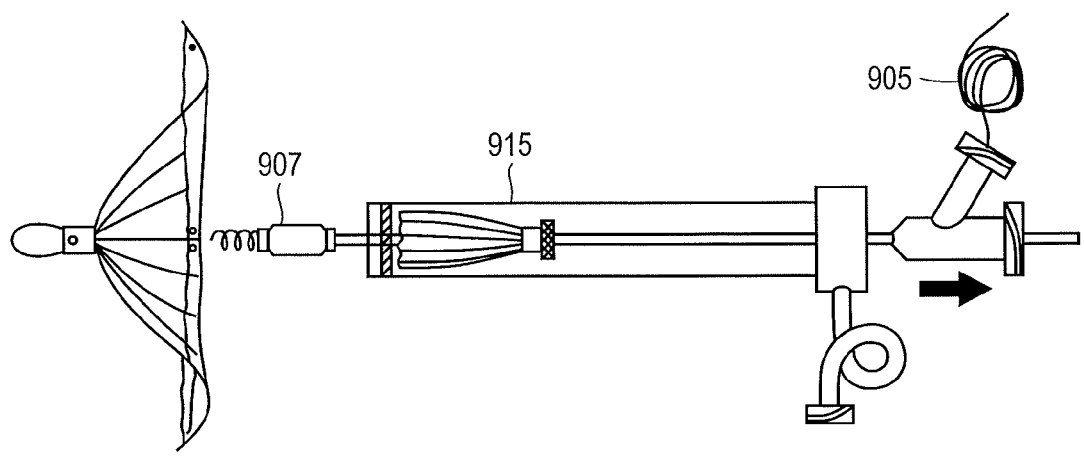

In some variations, the applicator is configured so that the end or ends of the collapse or expansive strand extend proximally in the applicator and can be removed (e.g., withdrawn) from the implant or the applicator after it has been finally positioned. For example, FIG. 25A illustrates one variation of a system including an applicator 901 and an implant 903, in which the implant 903 includes a collapse strand 905 that extends around the perimeter of the implant and can collapse the struts of the implant if tensioned. The ends of the collapse strand 905 extend proximally into the applicator and extend from a port (e.g., on the handle at the proximal end of the applicator) 906, 906'. The applicator variation shown also includes an implant stabilization shaft (catheter) 909 which includes a balloon 907 for helping expand the implant once positioned, and an implant capture umbrella 920, within an outer cannula or guide catheter 915 of the applicator, similar to the applicator shown in FIG. 23A. In this example, the distal region of the applicator also includes a radiopaque marker 913 to aid in visualization. A balloon inflation port 927 is also present on the proximal end of the device. FIG. 25B illustrates the system of FIG. 25A in which the implant 903 has been detached from the applicator 901. In FIG. 25B the collapse strand 905 has been removed from the device. Presumably the device has been positioned in an acceptable position, and further adjustment is unnecessary. Until the strand is removed, the implant may be continuously collapsed and repositioned by pulling on the collapse strand 905, and using the implant capture umbrella 920 as previously described.

Figure 26A:
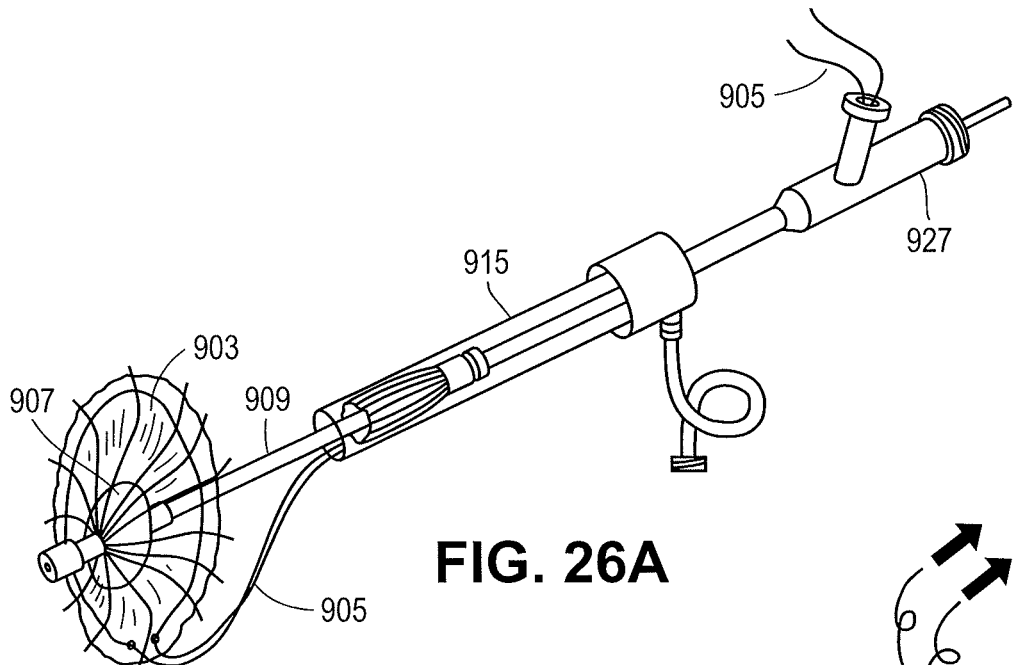
FIG. 26A shows another variation of an applicator configured to deliver and reposition and/or remove an implant.
Figure 26B:
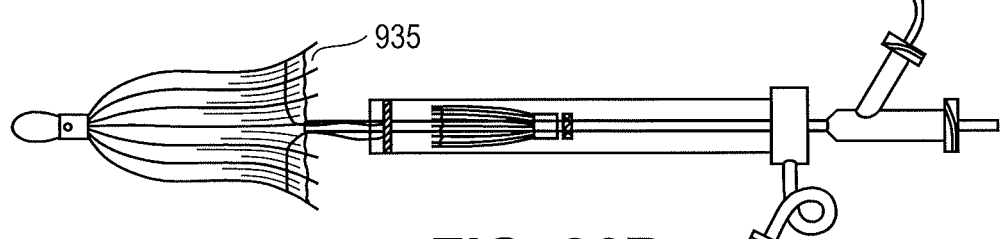
FIGS. 26B-26D illustrate operation of the applicator of FIG. 26A.
Figure 26C:
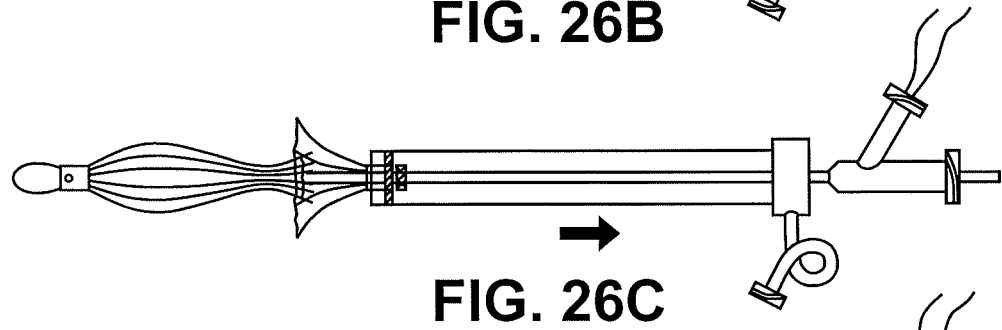
Figure 26D:
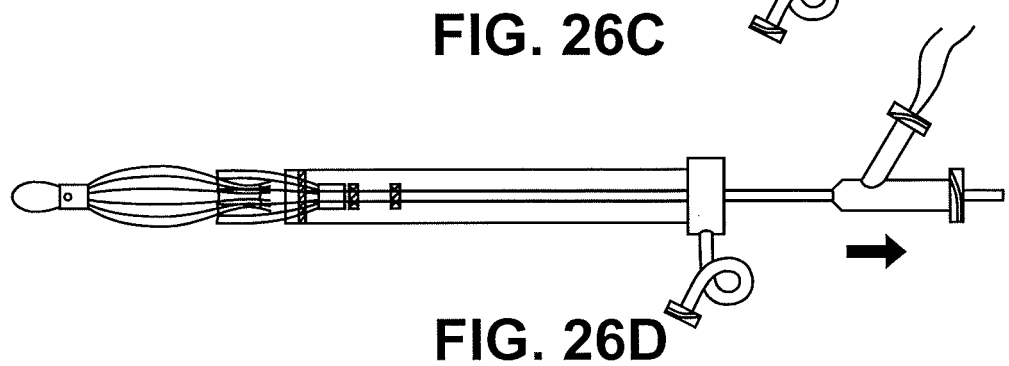

For example, FIGS. 26A-26D illustrate operation of the system of FIG. 25A. FIG. 26A shows a perspective view of the system of FIG. 25A, including an implant 903 that is attached to the distal end of an applicator 901. The very distal end of the implant includes a soft tip of foot 930. The implant may be inserted into the subject's heart (e.g., the left ventricle) as previously described. Once in position, it may be expanded as shown in FIG. 26A. The position or orientation of the implant may be confirmed or checked using visualization such as fluoroscopy. FIGS. 26B-26D illustrate retrieval of the implant after initially deploying it, but before removal of the collapse strand 905.

The implant 903 shown in FIGS. 25A-26D may be retrieved by pulling the free ends of the collapse wire 905 to collapse the implant, as shown in FIG. 26B. In this example, the passive anchors 935 can thus be disengaged from the heart wall. After at least partially collapsing the implant, the guide catheter 915 may be withdrawn to expose and expand the implant capture umbrella 920, as shown in FIG. 26C. In some variations, as described for FIG. 24C, above, the implant capture wire may be extended distally. Drawing the implant proximally and then pushing the guide catheter forward distally, as shown in FIG. 26D, will then capture the implant within the implant capture umbrella as it closes around the collapsed implant.

As mentioned briefly above, in some variations, the implant device includes a collapse element, such as the collapse strand described above, or a collapse sleeve. FIGS. 27A-27E illustrate operation of a system including an implant having a collapse sleeve and an applicator configured to operate the collapse sleeve.

Figure 27A:
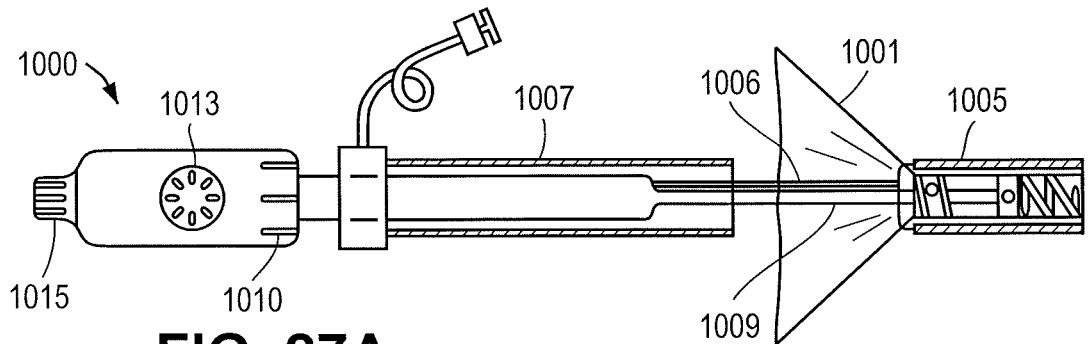
FIGS. 27A-27E illustrate the operation of a system including an implant having a collapse sleeve.
Figure 27B:
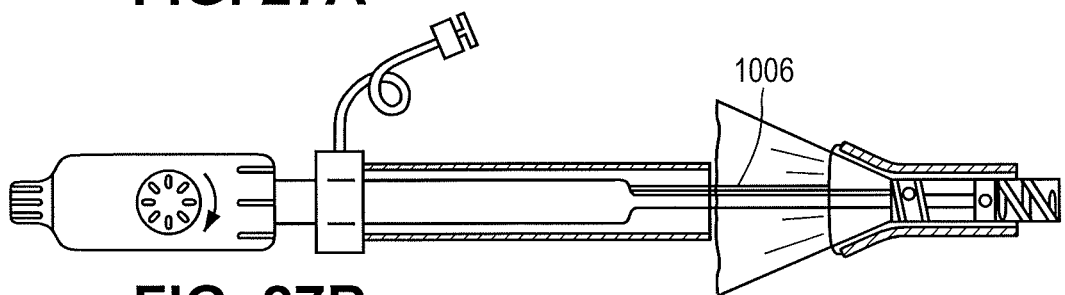
Figure 27C:
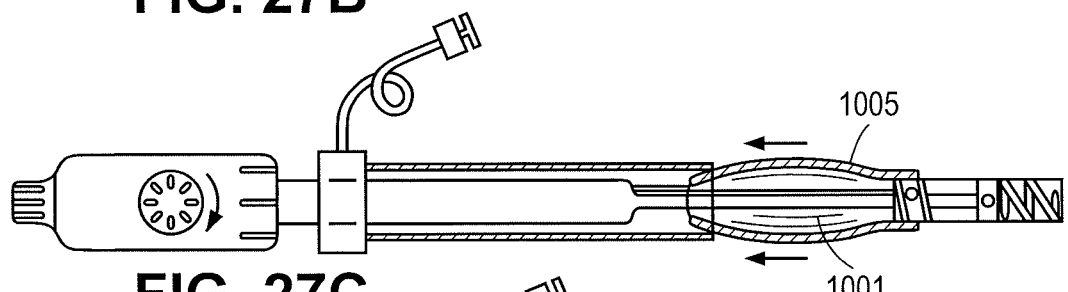
Figure 27D:
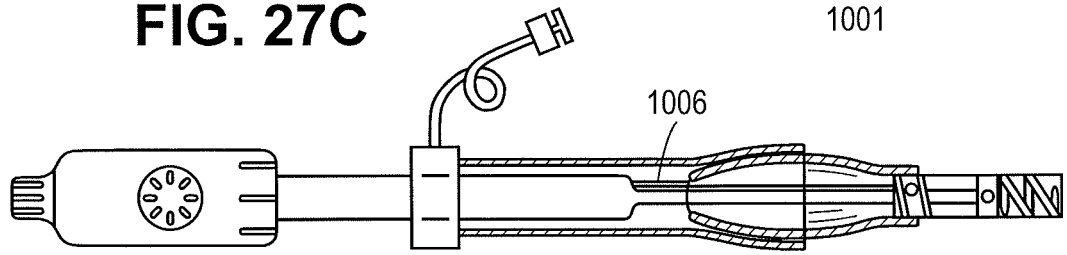
Figure 27E:
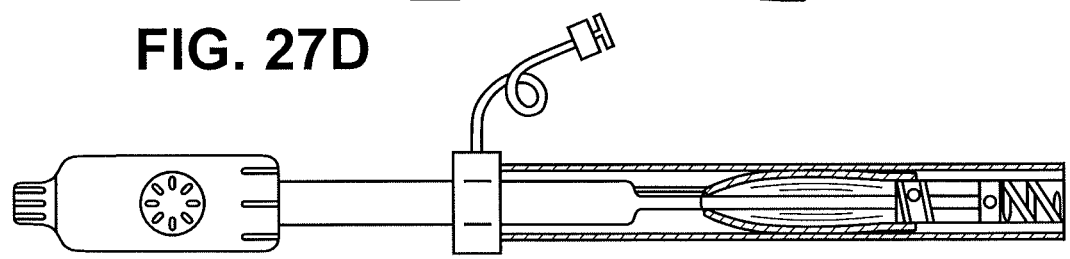

In FIG. 27A, the implant 1001 is shown in an expanded state. For simplicity sake, the struts are not shown. The implant includes a collapse sleeve 1005 that is positioned distally (e.g., over the stem of the implant) when the implant struts and membrane are deployed, as shown in FIG. 27A. In this example, the implant is coupled to an applicator 1000, that includes a handle region having a collapse knob 1013, an active anchor knob 1015, and a detachment knob 1010. The applicator also includes a guide catheter 1007, within which an extendable/retractable collapse sleeve pullwire 1006 and an implant stabilization shaft 1009 reside. FIGS. 27B-27E illustrate use of the applicator to collapse the implant 1005. For example, in FIG. 27B, the collapse knob (or other appropriate control) on the handle may be operated to draw the collapse sleeve 1005 proximally. For example, turning the collapse knob may cause the pull wire to draw the collapse sleeve 1005 over the implant membrane/struts, collapsing it, as illustrate in FIG. 27C. After the implant is collapsed, it may be pulled inside the guide catheter and removed from the patient, or repositioned and redeployed (e.g., by extending the implant from the guide catheter and pushing on the collapse sleeve guidewire to expand the membrane/struts). The collapse sleeve pullwire may be a wire, a rod, a tube, etc., and may be used for pulling and/or pushing the collapse sleeve.

Figure 28A:
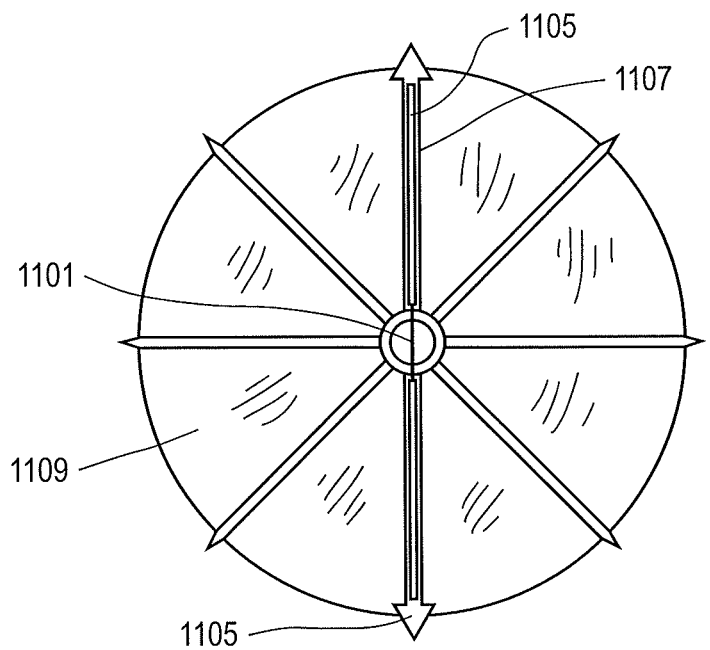
FIGS. 28A and 28B show front and side views, respectively, of an implant having a collapse sleeve, similar to the implant shown in FIGS. 27A-27E.
Figure 28B:
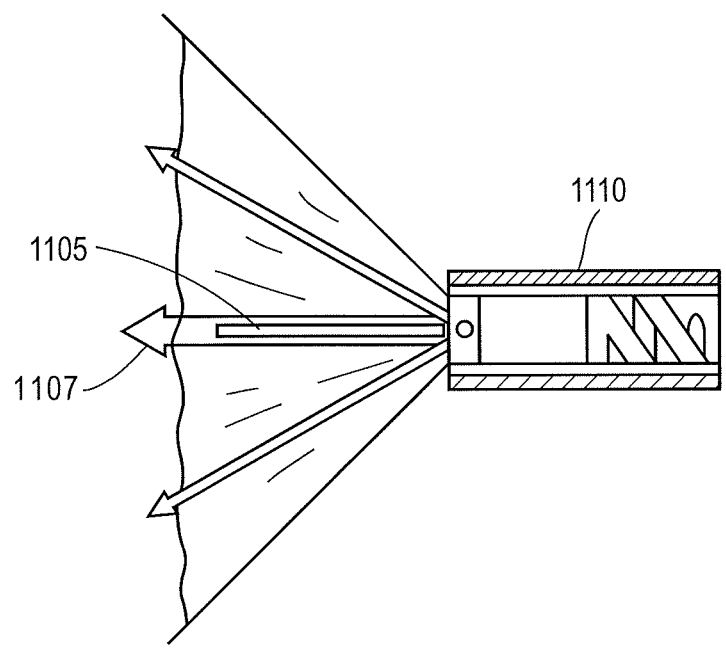

The collapse sleeve may be coupled with the collapse sleeve pullwire (or other collapse sleeve control on the applicator), using a configuration such as that illustrated in FIGS. 28A and 28B. FIG. 28A shows a front view of an expanded implant including a centrally-located attachment mechanism 1101 for the collapse sleeve. This attachment mechanism can be a cross-bar or wire that extends across the central opening and connects to one or more points on the inner surface of the sleeve. In this example, both the hub region of the implant and the collapsible struts/membrane region include a track or slot along which this cross-bar or wire can move to allow the collapse sleeve to be moved proximally or distally. For example, two opposite struts 1107 shown in FIG. 28A include a slot or track 1105 along which the cross-bar or wire connected to the collapse sleeve may move. The applicator may include a shaft or wire that engages this attachment mechanism and pulls it proximally or pushes it distally. FIG. 28B shows a side view of the implant shown in FIG. 28A, including the collapse sleeve 1110.

Figure 29A:
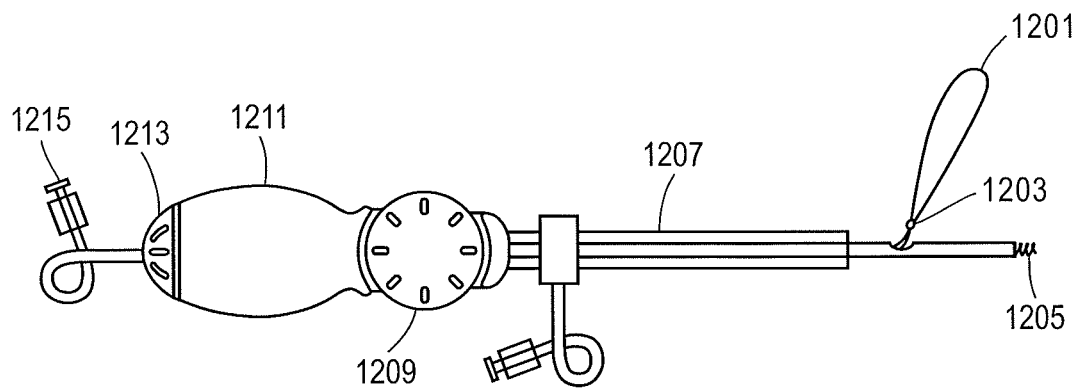
FIG. 29A shows an applicator including a retrieval element configured as a lariat.
Figure 29B:
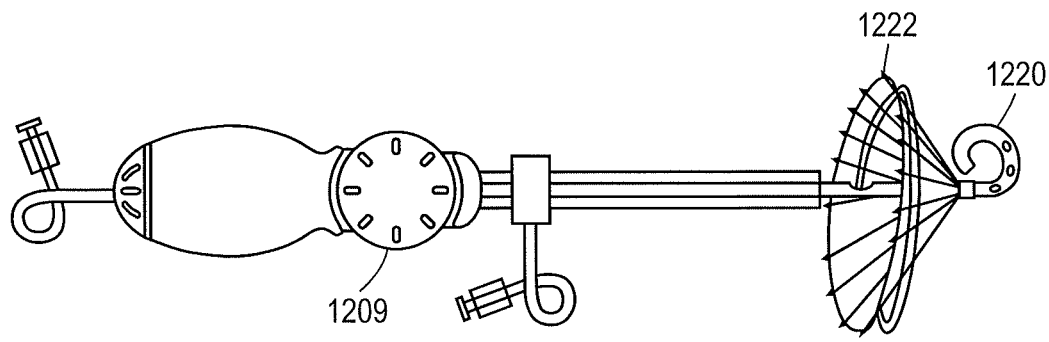
FIGS. 29B-29E illustrate operation of the applicator of FIG. 29A and an implant.

Another variation of an implant delivery system is shown in FIGS. 29A-29E. FIG. 29A shows an applicator including a collapse line or lasso 1201 extending from a side port on an implant stabilizing shaft passing through a guide catheter 1207 on the device. The distal end of the implant stabilizing shaft includes a detachment screw 1205 that may be activated to detach an implant from the device. In this example, the collapse line may be drawn proximally (e.g., towards the handle of the applicator 1211) by manipulating a control on the handle such as a collapse line control knob 1209. The handle may also include one or more controls for detaching the implant 1213, or the like. In some variations the collapse line is connected to an implant prior to deployment of the implant, and may be released from the implant after it has been finally positioned. In other variations, the collapse line is not integral to the implant, but may be connected around the implant after it has been released.

Figure 29C:
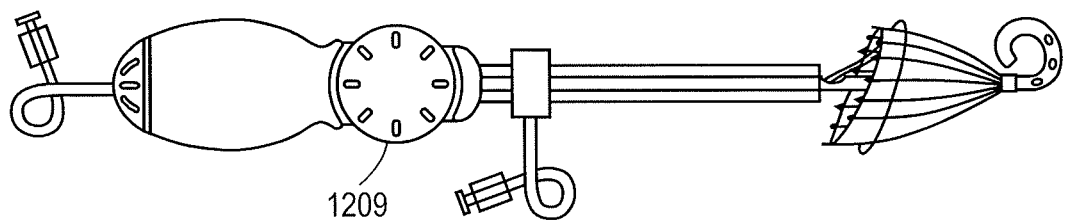
Figure 29D:
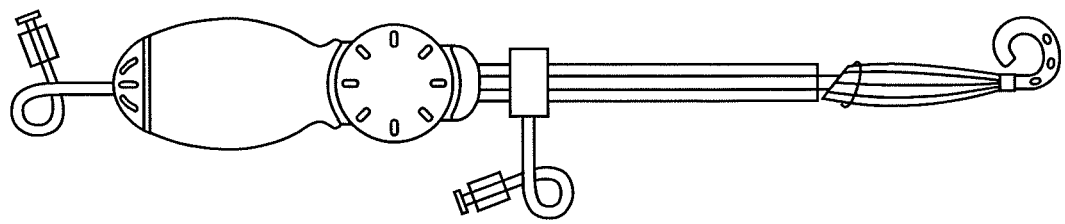
Figure 29E:
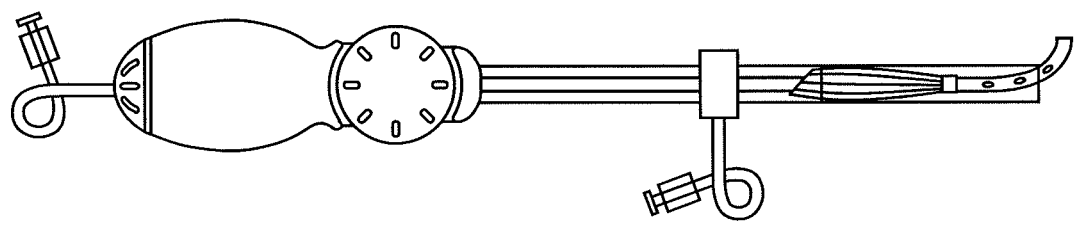
Figure 30A:
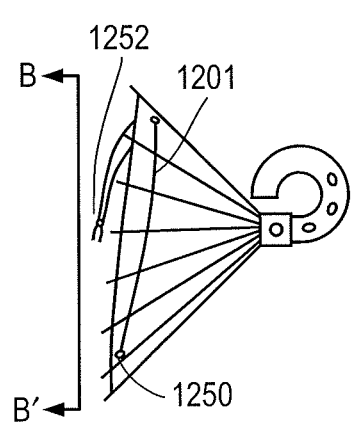
FIGS. 30A and 30B show front and side views, respectively, of an implant that may be used with the applicator shown in FIG. 29A and illustrated in FIGS. 29B-29E.
Figure 30B:
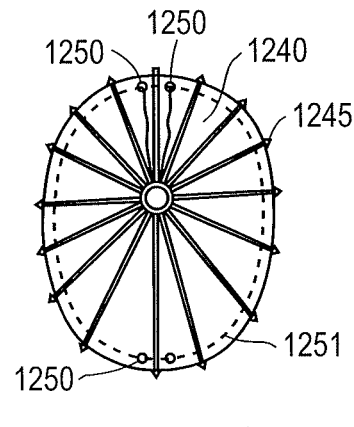

FIGS. 29B-29E illustrate operation of the implant delivery system including the applicator and implant. For example, in FIG. 28B, the deployed implant is still attached to the applicator, but it is desired to collapse and reposition (or remove) the implant. In this variation the implant includes an implant stem, configured as an atraumatic foot 1220 extending from an expanded implant umbrella region 1222. In FIG. 29C the collapse line or lasso 1201 is contracted to collapse the implant until it is sufficiently collapsed to fit into the guide catheter 1207, as shown in FIG. 29D. Once it has collapsed sufficiently, the guide catheter may be moved distally to enclose the implant, as shown in FIG. 29E. FIGS. 30A and 30B illustrate side and front views, respectively, of an implant which may be used with the applicator shown in FIG. 29A-29E. The implant is shown connected to a collapse line 1201 (or strand) that passes through two or more skives 1250 on the membrane 1240. The collapse line 1201 includes a push knot 1252. The implant also includes multiple struts 1245.

FIGS. 35A-35E illustrate another variation of a system for applying and removing a partitioning device (implant) that includes an applicator having a collapse line. For example, FIG. 35A shows a system including an applicator 1700 having a delivery cannula, and an implant 1701 including expandable struts with passive anchors at their ends. The system shown in FIG. 35A is in the undeployed state, and the distal end of the implant (including an atraumatic foot region extending distally). It can be deployed by pushing it from the delivery catheter region so that the struts can expand, as shown in FIG. 35B. In this example, a strand or lariat 1705 is pre-positioned around the device, and passes into a lariat guide tube 1707 that is within the delivery catheter. As the device is deployed, the lariat expands around it, and the lariat guide tube 1707 remains connected. If the position is correct, the lariat (string) may be withdrawn by pulling it from one end to remove it from around the device (not shown), and withdrawing both the lariat and the lariat guide tube with the applicator 1700. FIGS. 35C-35E illustrate one method of repositioning or removing the implant by pulling on one or both ends of the lariat and collapsing the implant (e.g., collapsing the expanded struts, as shown in FIG. 35C), until it can be either repositioned, as shown in FIG. 35D, or withdrawn into the delivery catheter and removed, as shown in FIG. 35E.

Figure 31A:
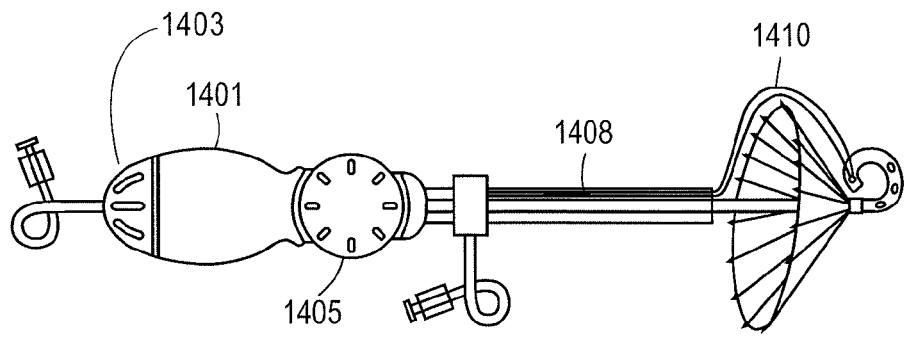
FIG. 31A shows another variation of a system including an applicator and an implant.
Figure 31B:
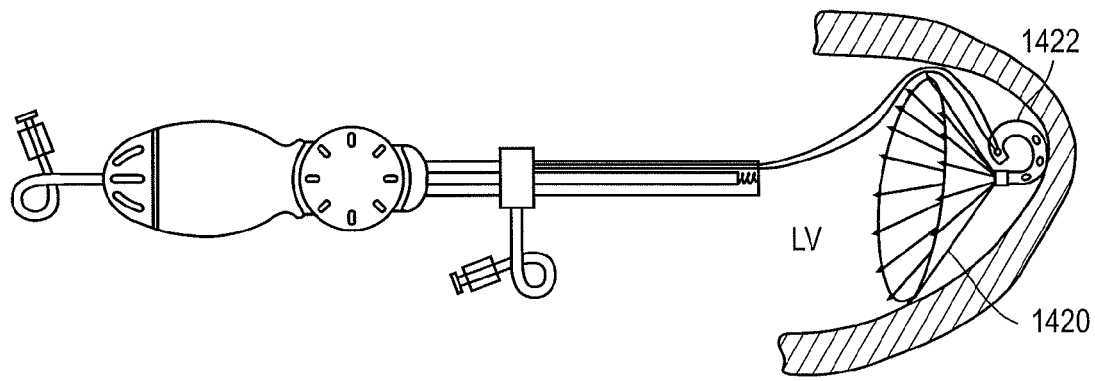
FIGS. 31B-31D illustrate retrieval of an implant using the system shown in FIG. 31A.
Figure 31C:
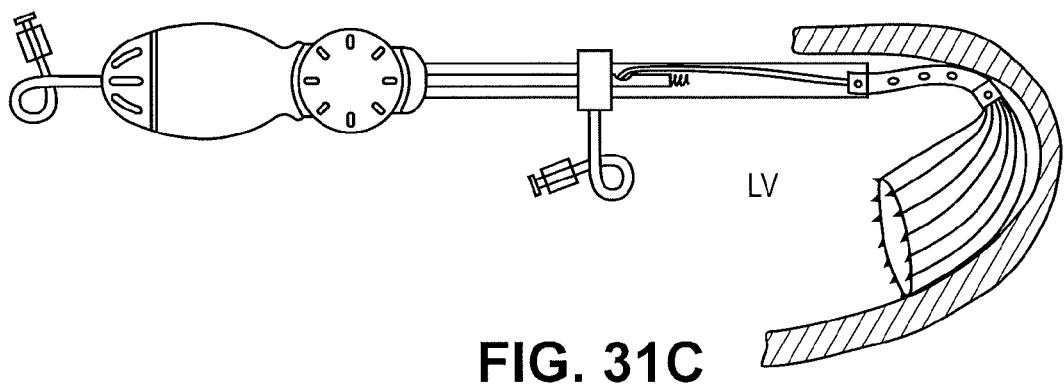
Figure 31D:
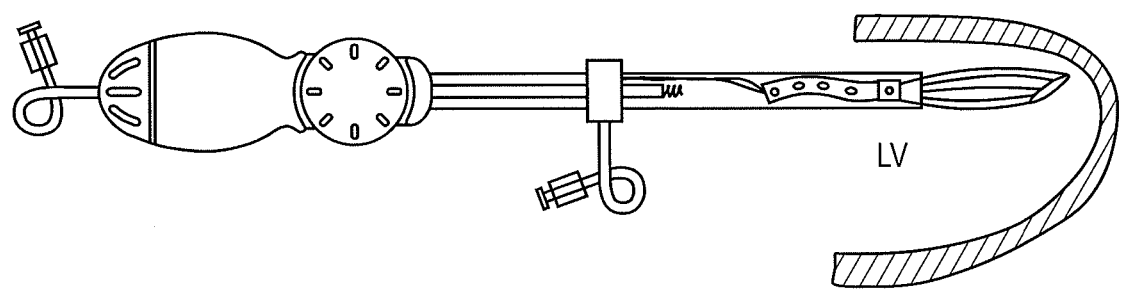

In some variations the implant is retrieved into the applicator after inverting the implant so that the membrane and/or struts may be collapsed as the implant is drawn into a catheter region of the applicator. One variation of this method and a system including this method is shown in FIGS. 31A-31D. For example, in FIG. 31A, the applicator includes a handle region 1401 having one or more controls 1403, 1405, an elongate catheter region 1408 including a guide catheter, and an implant stabilization shaft and a retrieval line 1410 that connects to the distal end (e.g., the foot region 1422) of the implant. FIGS. 31B-31D illustrate removal of a deployed implant using this applicator. Pulling on the retrieval line 1410 after deployment will disengage the implant 1420 from the walls of the left ventricle, as shown in FIG. 31C and invert the implant within the left ventricle (lv) as it is drawn towards the guide catheter in the applicator. In this example, the retrieval line 1410 is attached to a flexible foot region 1422. Withdrawing the inverted implant into the applicator collapses the implant, as shown in FIG. 31D.

Figures 33D, 33E:
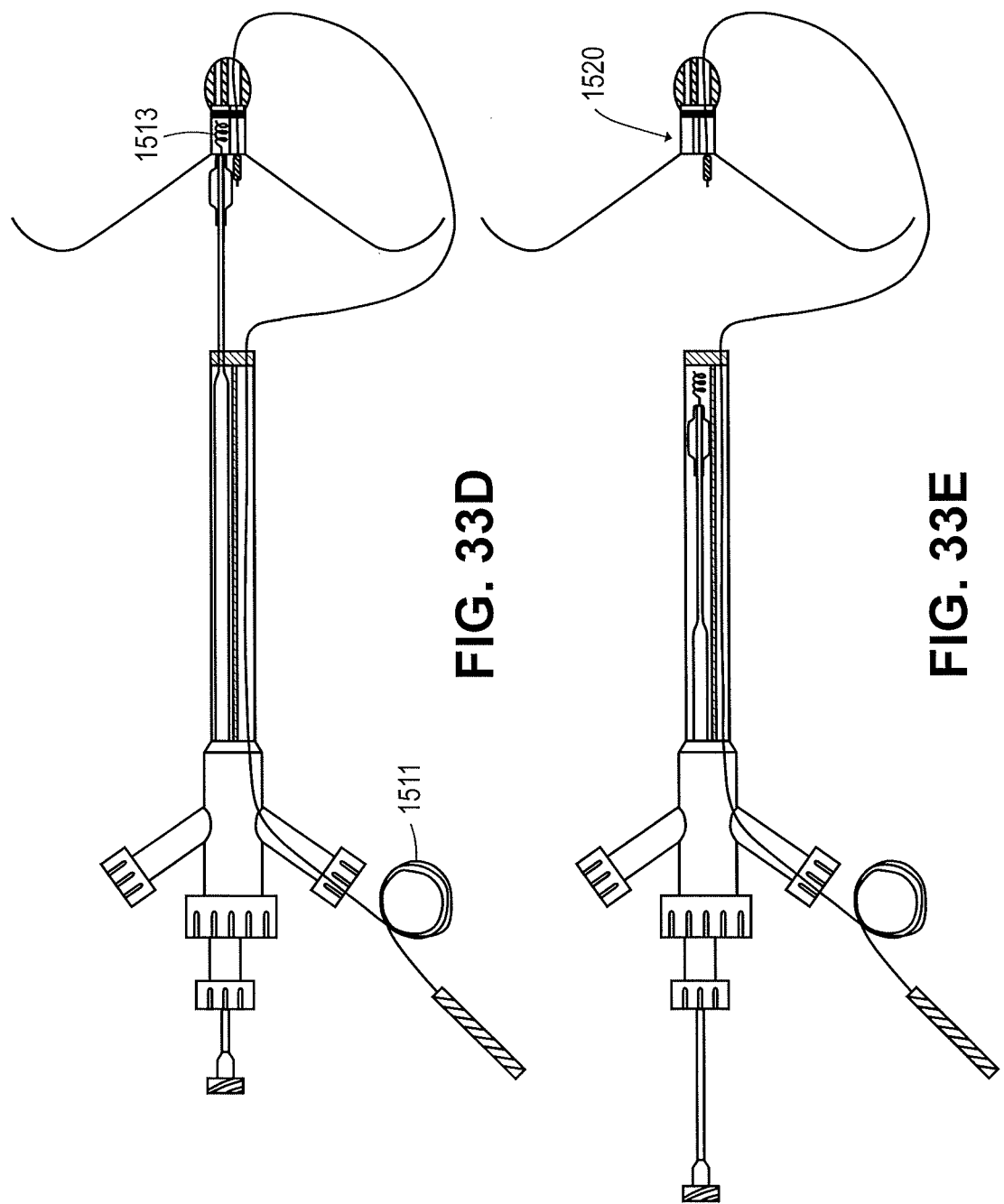

FIGS. 32A and 32B illustrate another variation of an applicator 1500 configured to remove an implant by inverting the implant, and FIGS. 33A-33H illustrate the operation of the applicator 1500. In FIG. 32A, the system includes a handle region 1501 (control region) having a balloon inflation port 1503, an implant release port 1505, and an implant capture port 1507. The proximal control/handle region is connected to an elongate insertion cannula. An implant stabilization shaft 1509 configured to releasably secure to an implant and an implant capture wire 1511 extend through the cannula, and are axially movable therein. Thus, the cannula may include one or more internal axial lumen through which these structures may move. The implant stabilization shaft may include a balloon 1515 or other deployment-aiding structure, and/or a screw 1513 that can be used to detach/reattach the implant. FIG. 33B shows the device of claim 33A in partial cross-section, so that the implant stabilization shaft 1509 and implant capture wire 1511 are visible. The proximal end of the implant stabilization shaft 1509 is shown withdrawn so that the implant stabilization shaft is completely within the cannula.

FIGS. 33A-33H illustrate operation of this system. In FIG. 33A, the applicator 1500 of FIGS. 32A and 32B is shown in partial cross-section with an implant 1520 pre-loaded on the distal end. The implant capture wire 1511 in this variation is pre-loaded through the implant, so that it extend from the implant release port, through the implant, and out of the implant capture port. For convenience, FIG. 33A shows the implant in an expanded (deployed) configuration, although it may also be contracted in a delivery configuration in which the struts and any membrane between them is collapsed and retracted at least partially into the delivery catheter.

FIG. 33B shows a cross-section through the distal region of the implant, showing a passageway through which the implant capture wire may pass. This passageway may be sized so that a retainer 1530 on the end of the implant capture wire cannot pass through the implant, so that it can be retrieved by pulling on the wire, as illustrated below. If the implant it positioned and deployed as desired, the implant capture wire may be completely withdrawn through the implant. For example, the retainer 1530 on the end of the implant capture wire may be removed or disengaged.

After deploying the device into a heart, e.g., into the left ventricle of the heart, the device may be withdrawn. For example, to remove the implant from the heart, one end of the implant capture wire 1511 may be withdrawn down the device, as illustrated in FIG. 33C. In this example, the implant capture wire is drawn proximally by pulling on the end of the implant capture wire extending from the implant capture port 1507. The opposite end of the implant capture wire is attached to a retainer 1530. The retainer is sized (or otherwise configured) so that it cannot pass through the implant hub 1533, as shown in FIG. 33D.

FIG. 33E shows the implant stabilization shaft disengaged from the implant 1520. With the implant stabilization shaft attached, the implant may partially withdrawn from the wall of the heart, to allow it space to move (e.g., within the ventricle) so that it has adequate room to be flipped, as illustrated in FIG. 33F. For example, pulling on the implant capture wire 1511 extending from the implant capture port 1507 will draw the foot (tip) of the implant to be drawn towards the applicator (the distal end of the cannula). In the example shown in FIG. 33F, the distal end of the catheter is marked with a radiopaque marker 1550, so that the position of the applicator can be observed. FIGS. 33G and 33H illustrate the steps of collapsing the implant into, by continuing to secure the implant at the distal end of the applicator (e.g., pulling on the implant capture wire 1511) while sliding a guide catheter, sheath, or collapsing catheter 1539 over the flipped implant. The guide catheter (or sheath, or collapsing catheter) 1539 moves axially over the delivery catheter 1561 to extend distally beyond the end of the guide catheter, and the distal end of the both may include a radiopaque marker 1550. Once collapsed, the implant and applicator may be removed from the patient.

In any of the variations described herein the implant may be removed after it has been at least partially secured or even anchored to the patient's heart wall. For example, an implant may include passive anchors at the ends of the ribs (struts), which may be pointed or sharp, and configured to partially penetrate the heart wall. Removal or re-positioning of the implant may therefore be simplified by disengaging the implant from the heart wall. In some variations a portion of the implant is axially shortenable (e.g., collapsible, compressible, etc.) after it has been deployed so that it can be disengaged. For example, the hub and/or foot region of the implant may be collapsible, as illustrated in FIGS. 34A-34D. In some variations the shortenable region is a telescoping region. In some variations the shortenable region includes a spring or other biasing element that holds the region is an extended (unshortened) position until it is allowed to compress or otherwise activated. Thus, the shortenable region may be activated by applying force to shorten it. In some variations, the shortenable region is lockable so that it cannot be shortened until the lock is disengaged. A lock may include a pin, a catch, or the like. The lock may be mechanically, electrically or magnetically activated.

FIG. 34A shows an implant having an elongated hub region 1601 that includes a collapse region 1601. The hub region 1601 of FIG. 34A is shown in more detail in FIG. 34B. In this variation, the collapsible region includes hinged arms. The hub region in this example may be foreshortened by pulling proximally on a string (or strings) 1605 attached distally to the collapse region 1601. This is illustrated in FIG. 34C, and in greater detail in FIG. 34D. In this example, the string passes from the proximal end of the implant (and may pass through or into an applicator), loops around a hole in the implant, and then back out proximally. After the device position is finalized, the string 1605 may be removed by withdrawing one end of the string while allowing the other end to be pulled through the implant and out again, as illustrated in FIGS. 34E and 34F.

In other variations, the foreshortening of the implant does not require a string, but may be activated by merely applying pressure or force to the device.

Figure 36A:
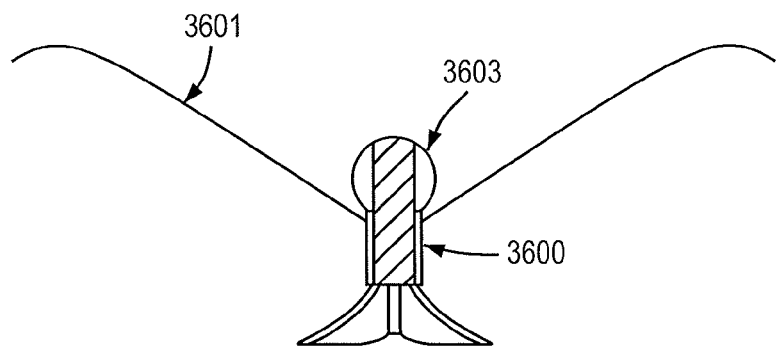
FIG. 36A shows a cross-section of another variation of an implant.
Figure 36B:
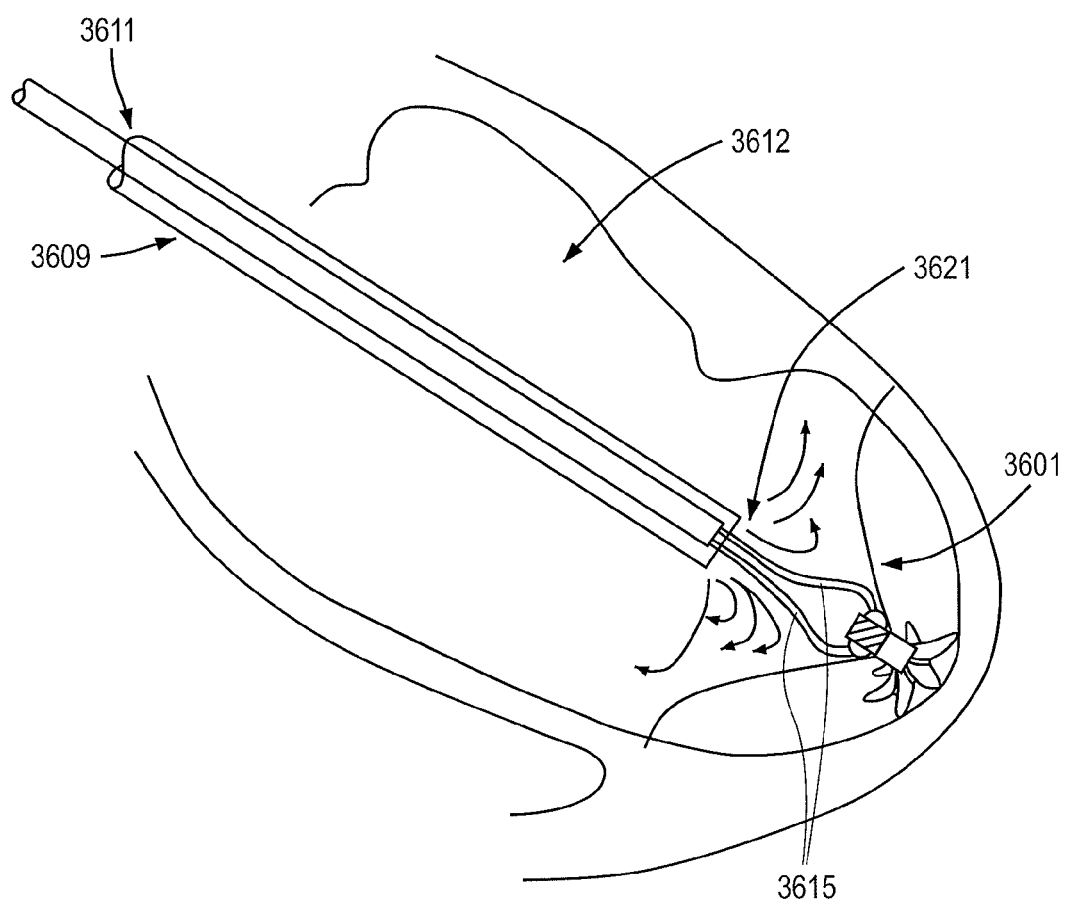
FIGS. 36B-36C illustrate a method of removing an implant such as the one shown in FIG. 36A, in which temperature is changed to induce collapse of an implant so that it can be withdrawn.
Figure 36C:
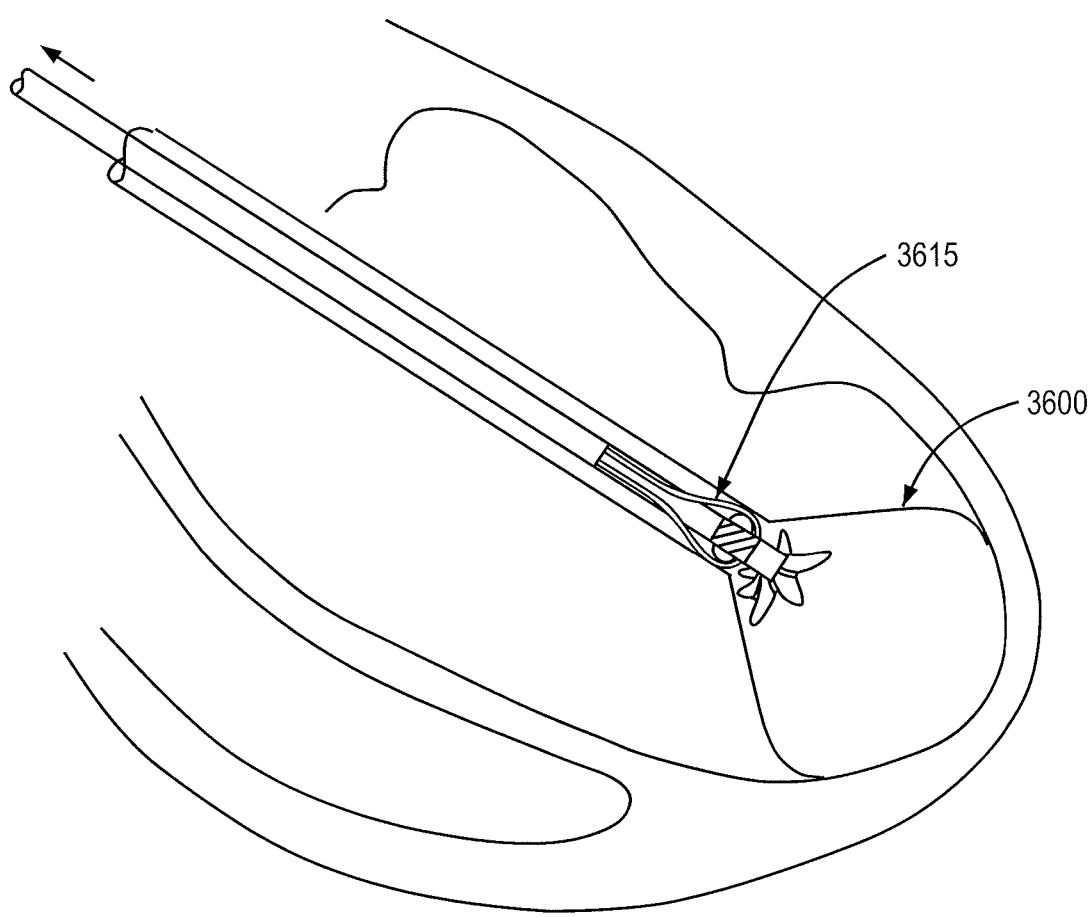

In addition to the devices and methods for collapsing an implant described above, other methods may also be applied, either separately or in combination with the methods described above. For example, the implant may be collapsed by changing the temperature of the implant. This method is particularly effective when the implant is made (at least partially) of a shape memory material, such as Nitinol. FIG. 36A shows a cross-section through one variation of an implant 3600 in which the device includes a frame (e.g., having struts 3601), and a centrally (and proximally) located tip 3603 that may be grasped by an applicator, as illustrated in FIGS. 36B and 36C, described below. The frame (e.g., struts 3601) may be formed in part from a shape-memory material that may transition between an expanded (Austentite) configuration into a collapsed (Martensite) configuration when exposed to cold.

FIGS. 36B and 36C illustrate this transition. In FIG. 36B the device 3600 has been inserted in to left ventricle 3612. An applicator 3609 including a pair of grabbing jaws 3615 (although any coupling means for securing the implant to the applicator may be used, including those described above) is brought near the implant, and the jaws 3615 may be secured to the tip 3603 of the implant. The applicator also includes a channel for applying chilled fluid 3621. For example, cooled saline (e.g., between 0 and 10 degrees C.) may be applied from the channel 3621 to change the Nitinol of the implant from the austenite phase (expanded) to the martensite phase (collapsed). This is illustrated in FIG. 36C. The implant 3600 is shown in a collapsed configuration, disengaged from the wall. The implant is also shown being drawn into the applicator (which may include a catheter into which the implant may be withdrawn. In this example, the central region of the applicator, including the grasping jaws 3615 can be withdrawn into the outer cannula of the applicator.

To the extent not otherwise described herein, the various components of the implants, applicators, and delivery systems including any of them may be formed of conventional materials and in a conventional manner as will be appreciated by those skilled in the art.

While particular forms of the invention have been illustrated and described herein, it will be apparent that various modifications and improvements can be made to the invention. Moreover, individual features of embodiments of the invention may be shown in some drawings and not in others, but those skilled in the art will recognize that individual features of one embodiment of the invention can be combined with any or all the features of another embodiment. Accordingly, it is not intended that the invention be limited to the specific embodiments illustrated. It is intended that this invention to be defined by the scope of the appended claims as broadly as the prior art will permit.

What is claimed is:

1. A method for removing or repositioning an implant in a heart chamber, the implant including a plurality of self-expanding struts and a strand extending transversely across the struts, the method comprising:
   providing an applicator comprising an elongate body having a proximal end, a distal end, and a strand capture element extendable from the distal end;
   inserting the distal end of the applicator into the heart chamber;
   extending the strand capture element from the distal end of the applicator;
   engaging the strand with the strand capture element;
   tensioning the strand with the strand capture element to collapse the self-expanding struts of the implant; and
   withdrawing at least a portion of the collapsed self-expanding struts of the implant into the distal end of the applicator.

2. The method of claim 1, wherein the applicator further comprises an implant stabilizing shaft extendable from the distal end of the applicator.

3. The method of claim 2, further comprising:
   extending the implant stabilizing shaft from the distal end of the applicator; and
   engaging the implant with the implant stabilizing shaft.

4. The method of claim 1, wherein the applicator further comprises a control at the proximal end of the elongate body that is configured to manipulate the strand capture element.

5. The method of claim 1, wherein the strand capture element is a hook.

6. The method of claim 1, wherein the strand capture element is a grasper.

7. The method of claim 1, wherein the strand capture element is a jaw.

8. The method of claim 1, wherein the strand is tensioned with the strand capture element by withdrawing the strand capture element proximally into the applicator.

9. The method of claim 1, further comprising pushing the implant distally to disengage the implant from a wall of the heart chamber.

10. The method of claim 1, wherein the applicator further comprises an implant capture umbrella extendable from the distal end of the applicator.

11. The method of claim 10, further comprising extending the implant capture element distally out of the applicator and over at least a portion of the collapsed self-expanding struts of the implant.

12. The method of claim 1, wherein the applicator further comprises an inflatable everting cuff located on the distal end of the applicator.

13. The method of claim 12, further comprising inflating the inflatable everting cuff until the inflatable everting cuff extends over at least a portion of the collapsed self-expanding struts of the implant.

14. A method for removing or repositioning an implant in a heart chamber, the implant including a plurality of self-expanding struts and a strand extending transversely across the struts, the method comprising:
   inserting an applicator into the heart chamber, the applicator comprising an elongate body having a proximal end, a distal end, a lumen extending therethrough, an implant capture umbrella extendable from the distal end of the applicator, and at least one end of the strand of the implant extending proximally into the lumen of the applicator;
   pulling the at least one end of the strand to collapse the self-expanding struts of the implant;
   extending the implant capture element distally out of the applicator and over at least a portion of the collapsed self-expanding struts of the implant; and
   withdrawing at least a portion of the collapsed self-expanding struts of the implant into the distal end of the applicator.

15. The method of claim 14, wherein the applicator further comprises an implant stabilizing shaft extendable from the distal end of the applicator.

16. The method of claim 15, further comprising:
   extending the implant stabilizing shaft from the distal end of the applicator; and
   engaging the implant with the implant stabilizing shaft.

17. The method of claim 14, wherein the applicator further comprises an inflatable everting cuff located on the distal end of the applicator.

18. The method of claim 17, further comprising inflating the inflatable everting cuff until the inflatable everting cuff extends over at least a portion of the collapsed self-expanding struts of the implant.

19. A method for removing or repositioning an implant in a heart chamber, the implant including a plurality of self-expanding struts and a strand extending transversely across the struts, the method comprising:
   providing an applicator comprising an elongate body having a proximal end, a distal end, and a strand capture element extendable from the distal end;
   inserting the distal end of the applicator into the heart chamber;
   extending the strand capture element from the distal end of the applicator;
   engaging the strand with the strand capture element; and
   tensioning the strand with the strand capture element to collapse the self-expanding struts of the implant.

20. The method of claim 19, further comprising repositioning the implant.

21. The method of claim 20, further comprising releasing the strand from the strand capture element to expand the self-expanding struts of the implant.

* * * * *